(12) United States Patent
Scholler et al.

(10) Patent No.: US 7,795,411 B2
(45) Date of Patent: Sep. 14, 2010

(54) VECTORS FOR EXPRESSING IN VIVO BIOTINYLATED RECOMBINANT PROTEINS

(75) Inventors: Nathalie Scholler, Seattle, WA (US); Barbara Garvik, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 237 days.

(21) Appl. No.: 11/669,811

(22) Filed: Jan. 31, 2007

(65) Prior Publication Data

US 2008/0085539 A1 Apr. 10, 2008

Related U.S. Application Data

(60) Provisional application No. 60/850,183, filed on Oct. 5, 2006.

(51) Int. Cl.
C07H 21/04 (2006.01)
C12P 21/06 (2006.01)
C12P 9/00 (2006.01)
(52) U.S. Cl. ..................... 536/23.4; 435/69.1; 435/183
(58) Field of Classification Search ....................... None
See application file for complete search history.

(56) References Cited

U.S. PATENT DOCUMENTS

| 5,252,466 | A | * | 10/1993 | Cronan, Jr. ................. | 435/69.7 |
| 5,316,923 | A | | 5/1994 | Christiansen | |
| 6,190,883 | B1 | * | 2/2001 | Srivastava et al. .......... | 435/69.1 |
| 6,300,065 | B1 | | 10/2001 | Kieke | |
| 6,358,733 | B1 | | 3/2002 | Motwani | |
| 6,423,538 | B1 | | 7/2002 | Wittrup | |
| 6,699,658 | B1 | | 3/2004 | Wittrup | |

FOREIGN PATENT DOCUMENTS

| DE | WO2004076670 | * | 9/2004 |
| WO | 0023579 | A1 | 4/2000 |
| WO | 2005040395 | A1 | 5/2005 |
| WO | 2006099141 | A2 | 9/2006 |

OTHER PUBLICATIONS

Bowers et al., Protein transport from the late Golgi to the vacuole in the yeast *Saccharomyces cerevisiae*., Biochimica et Biophysica Acta, 2005, vol. 1744, pp. 438-454.*
Tatsumi et al., Construction of Biotinylated Firefly Luciferases Using Biotin Acceptor Peptides, Analytical Biochemistry, 1996, vol. 243, pp. 176-180.*
Parrott et al., Metabolic Biotinylation of Secrete and Cell Surface Proteins from Mammalian Cells., Biochemical and Biophysical Research communication, 2001, vol. 281, pp. 993-1000.*
Wilcox et al., Mutation of a Tyrosine Localization signal in the Cytosolic tail of yeast Kex2 Protease Disrupts Golgi Retention and Results in Default Transport to the Vacuole., Molecular Biology of the Cell, 3, 1353-1371.*
Barat, B., and A.M. Wu, "Metabolic Biotinylation of Recombinant Antibody by Biotin Ligase Retained in the Endoplasmic Reticulum," Biomolecular Engineering (24):283-291, 2007.
Bergan, L., et al., "Development and In Vitro Validation of Anti-Mesothelin Biobodies That Prevent CA125/Mesothelin-Dependent Cell Attachment," Cancer Letters (255):263-274, 2007.
De Boer, E., et al., "Efficient Biotinylation and Single-Step Purification of Tagged Transcription Factors in Mammalian Cells and Transgenic Mice," PNAS 100(13):7480-7485, Jun. 24, 2003.
Scholler, N., and B. Garvik, "Biobodies: Generation and Validation," Journal of Immunology 176(Suppl. S):S12 (Abstract 41.12), Apr. 2006.
Scholler, N., et al., "Method for Generation of In Vivo Biotinylated Recombinant Antibodies by Yeast Mating," Journal of Immunological Methods (317):132-143, 2006.
Swennen, D., et al., "Secretion of Active Anti-Ras Single-Chain Fv Antibody by the Yeasts *Yarrowia Lipolytica* and *Kluyveromyces Lactis*," Microbiology (141):41:50, 2002.
Van Werven F.J., and H.T.M. Timmers, "The Use of Biotin Taggin in *Saccharomyces cerevisiae* Improves the Sensitivity of Chromatin Immunoprecipitation," Nucleic Acids Research 34(4):e33, Feb. 2006, 7 pages.
Barker, D.F., and A.M. Campbell, "Genetic and Biochemical Characterization of the *birA* Gene and Its Product: Evidence for a Direct Role of Biotin Holoenzyme Synthetase in Repression of the Biotin Operon in *Escherichia coli*," Journal of Molecular Biology 146:469-492, 1981.
Barker, D.F., and A.M. Campbell, "The *birA* Gene of *Escherichia coli* Encodes a Biotin Holoenzyme Synthetase," Journal of Molecular Biology 146:451-467, 1981.
Bayer, E.A., and M. Wilchek, "Protein Biotinylation," Methods in Enzymology 184:138-160, 1990.
Chubet, R.G., and B.L. Brizzard, "Vectors for Expression and Secretion of FLAG Epitope-Tagged Proteins in Mammalian Cells," BioTechniques 20(1):136-141, 1996.
Cloutier, S.M., et al., "Streptabody, a High Avidity Molecule Made by Tetramerization of In Vivo Biotinylated, Phage Display-Selected Scfv Fragments on Streptavidin," Molecular Immunology 37:1067-1077, 2000.
Cronan, Jr., J.E., "Biotination of Proteins In Vivo," Journal of Biological Chemistry 265(18):10327-10333, 1990.
Etzioni, R., et al., "The Case for Early Detection," Nature Reviews 3:1-10, 2003.
Feldhaus, M.J., et al., "Flow-Cytometric Isolation of Human Antibodies From a Nonimmune *Saccharomyces cerevisiae* Surface Display Library," Nature Biotechnology 21:163-170, 2003.

(Continued)

*Primary Examiner*—David J Steadman
*Assistant Examiner*—Alexander D Kim
(74) *Attorney, Agent, or Firm*—Christensen O'Connor Johnson Kindness PLLC

(57) ABSTRACT

The present invention provides compositions and methods for generating in vivo biotinylated, secreted recombinant polypeptides comprising recombinantly co-expressing in a yeast cell (a) a secreted recombinant polypeptide comprising a biotin accepting site; and (b) a biotin ligase fused to the golgi localization domain so that the biotin ligase is localized to the golgi of the yeast cell where it acts on the biotin-accepting site of the secreted polypeptide as it transits the secretory system.

15 Claims, 14 Drawing Sheets

OTHER PUBLICATIONS

Fredriksson, S., et al., "Protein Detection Using Proximity-Dependent DNA Ligation Assays," *Nature Biotechnology* 20:473-477, 2002.

Fuller, R.S., et al., "Intracellular Targeting and Structural Conservation of a Prohormone-Processing Endoprotease," *Science* 246:482-486, 1989.

Gao, W.-M., et al., "Distinctive Serum Protein Profiles Involving Abundant Proteins in Lung Cancer Patients Based Upon Antibody Microarray Analysis," *BMC Cancer* 5:110, 2005, also available at http://www.biomedcentral.com/1471-2407/5/110.

Gorelik, E., et al., "Multiplexed Immunobead-Based Cytokine Profiling for Early Detection of Ovarian Cancer," *Cancer Epidemiology, Biomarkers & Prevention* 14(4):981-987, 2005.

Howard, P.K., et al., "Nucleotide Sequence of the *birA* Gene Encoding the Biotin Operon Repressor and Biotin Holoenzyme Synthetase Functions of *Escherichia coli*," *Gene* 35:321-331, 1985.

Kipriyanov, S.M., et al., "Affinity Enhancement of a Recombinant Antibody: Formation of Complexes With Multiple Valency by a Single-Chain Fv Fragment-Core Streptavidin Fusion," *Protein Engineering* 9(2):203-211, 1996.

Prince, H.E., "Biomarkers for Diagnosing and Monitoring Autoimmune Diseases," *Biomarkers* 10(Supplement 1):S44-S49, 2005.

Samols, D., et al., "Evolutionary Conservation Among Biotin Enzymes," *Journal of Biological Chemistry* 263(14):6461-6464, 1988.

Santala, V., and U. Lamminmäki, "Production of Biotinylated Single-Chain Antibody Fragment in the Cytoplasm of *Escherichia coli*," *Journal of Immunological Methods* 284:165-175, 2004.

Saviranta, P., et al., "In Vitro Enzymatic Biotinylation of Recombinant Fab Fragments Through a Peptide Acceptor Tail," *Bioconjugate Chemistry* 9:725-735, 1998.

Schatz, P.J., "Use of Peptide Libraries to Map the Substrate Specificity of a Peptide-Modifying Enzyme: A 13 Residue Consensus Peptide Specifies Biotinylation in *Escherichia coli*," *Bio/Technology* 11:1138-1142, 1993.

Scholler, N., et al., "Bead-Based ELISA for Validation of Ovarian Cancer Early Detection Markers," *Clinical Cancer Research* 12(7):2117-2124, 2006.

Scholler, N., et al., "Development of a CA125-Mesothelin Cell Adhesion Assay as a Screening Tool for Biologics Discovery," *Cancer Letters* 247(1):130-136, 2007.

Scholler, N., et al., "Soluble Member(s) of the Mesothelin/Megakaryocyte Potentiating Factor Family Are Detectable in Sera From Patients With Ovarian Carcinoma," *Proc. Natl. Acad. Sci. USA* 96:11531-11536, 1999.

Schummer, M., et al., "Comparative Hybridization of an Array of 21 500 Ovarian cDNAs for the Discovery of Genes Overexpressed in Ovarian Carcinomas," *Gene* 238:375-385, 1999.

Sibler, A.-P., et al., "In Vivo Biotinylated Recombinant Antibodies: High Efficiency of Labelling and Application to the Cloning of Active Anti-Human IgG1 Fab Fragments," *Journal of Immunological Methods* 224:129-140, 1999.

Smith, P.A., et al., "A Plasmid Expression System for Quantitative In Vivo Biotinylation of Thioredoxin Fusion Proteins in *Escherichia coli*," *Nucleic Acids Research* 26(6):1414-1420, 1998.

Sumiyama, K., et al., "Adaptive Evolution of the IgA Hinge Region in Primates," *Molecular Biology Evolution* 19(7):1093-1099, 2002.

Utz, P.J., "Protein Arrays for Studying Blood Cells and Their Secreted Products," *Immunological Reviews* 204:264-282, 2005.

Wang, X., et al., "Enhancement of scFv Fragment Reactivity With Target Antigens in Binding Assays Following Mixing With Anti-Tag Monoclonal Antibodies," *Journal of Immunological Methods* 294:23-35, 2004.

Warren, D.J., et al., "Use of an In Vivo Biotinylated Single-Chain Antibody as Capture Reagent in an Immunometric Assay to Decrease the Incidence of Interference From Heterophilic Antibodies," *Clinical Chemistry* 51(5):830-838, 2005.

Weaver-Feldhaus, J.M., et al., "Directed Evolution for the Development of Conformation-Specific Affinity Reagents Using Yeast Display," *Protein Engineering, Design & Selection* 18(11):527-536, 2005.

Wilcox, C.A., et al., "Mutation of a Tyrosine Localization Signal in the Cytosolic Tail of Yeast Kex2 Protease Disrupts Golgi Retention and Results in Default Transport to the Vacuole," *Molecular Biology of the Cell* 3:1353-1371, 1992.

"Yeast Display scFv Antibody Library User's Manual," Pacific Northwest National Laboratory, Richland, Washington 99352, pp. 1-44 <http://www.sysbio.org/dataresources/usermanual031113>, [retrieved Mar. 27, 2007].

Beckett, D., et al., "A Minimal Peptide Substrate in Biotin Holoenzyme Synthetase-Catalyzed Biotinylation," Protein Science 8(4):921-929, Apr. 1999.

Ladd, J., et al., "DNA-Directed Protein Immobilization on Mixed Self-Assembled Monolayers via a Streptavidin Bridge," Langmuir 20(19):8090-8095, Sep. 2004.

* cited by examiner

Method for Generating In Vivo Biotinylated Secreted Recombinant Polypeptides with Affinity for a Target Polypeptide

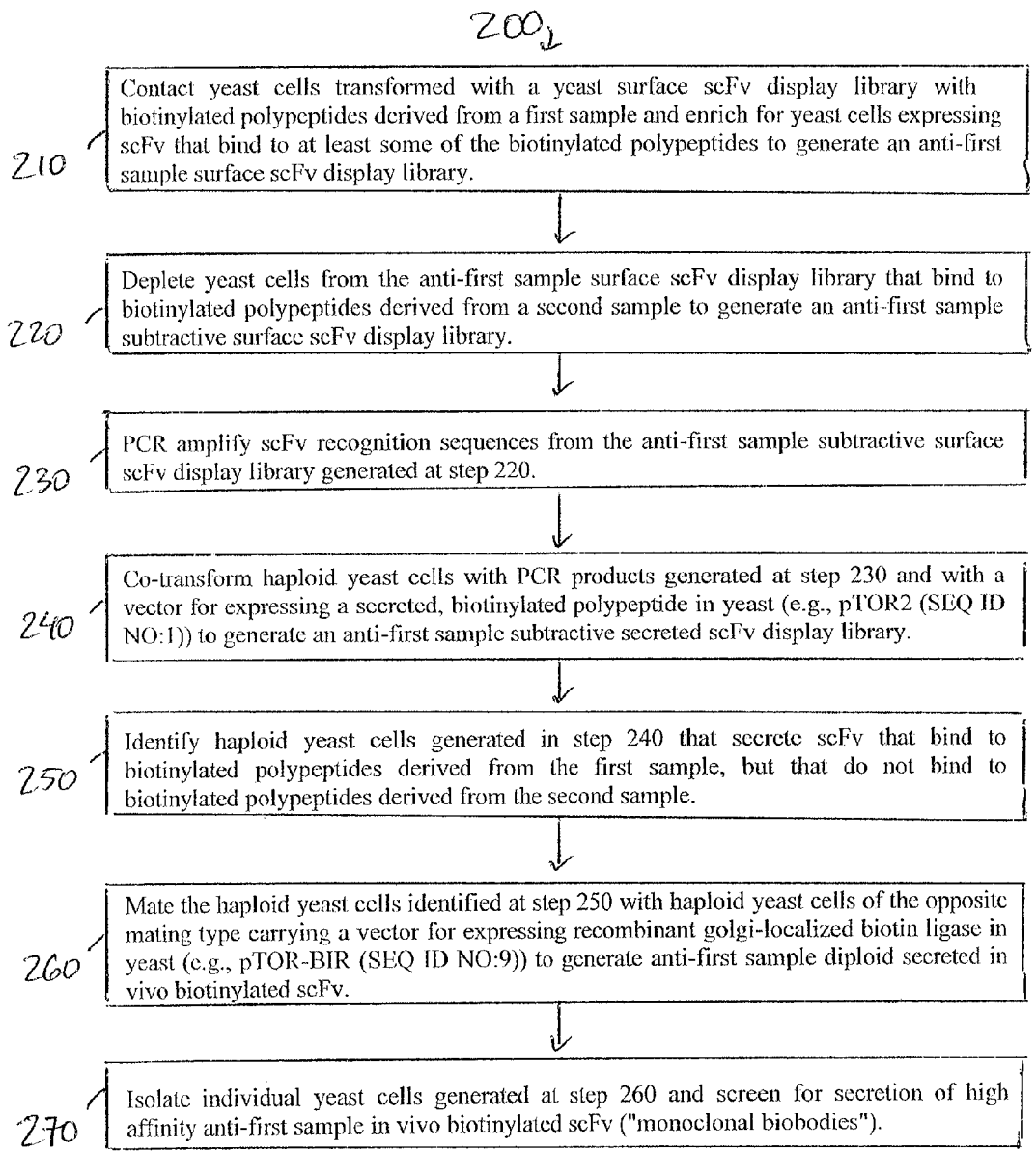

FIGURE 2B

Method for Generating In Vivo Biotinylated Secreted Recombinant Polypeptides with Affinity for Differentially Expressed Polypeptides

200

210 — Contact yeast cells transformed with a yeast surface scFv display library with biotinylated polypeptides derived from a first sample and enrich for yeast cells expressing scFv that bind to at least some of the biotinylated polypeptides to generate an anti-first sample surface scFv display library.

220 — Deplete yeast cells from the anti-first sample surface scFv display library that bind to biotinylated polypeptides derived from a second sample to generate an anti-first sample subtractive surface scFv display library.

230 — PCR amplify scFv recognition sequences from the anti-first sample subtractive surface scFv display library generated at step 220.

240 — Co-transform haploid yeast cells with PCR products generated at step 230 and with a vector for expressing a secreted, biotinylated polypeptide in yeast (e.g., pTOR2 (SEQ ID NO:1)) to generate an anti-first sample subtractive secreted scFv display library.

250 — Identify haploid yeast cells generated in step 240 that secrete scFv that bind to biotinylated polypeptides derived from the first sample, but that do not bind to biotinylated polypeptides derived from the second sample.

260 — Mate the haploid yeast cells identified at step 250 with haploid yeast cells of the opposite mating type carrying a vector for expressing recombinant golgi-localized biotin ligase in yeast (e.g., pTOR-BIR (SEQ ID NO:9)) to generate anti-first sample diploid secreted in vivo biotinylated scFv.

270 — Isolate individual yeast cells generated at step 260 and screen for secretion of high affinity anti-first sample in vivo biotinylated scFv ("monoclonal biobodies").

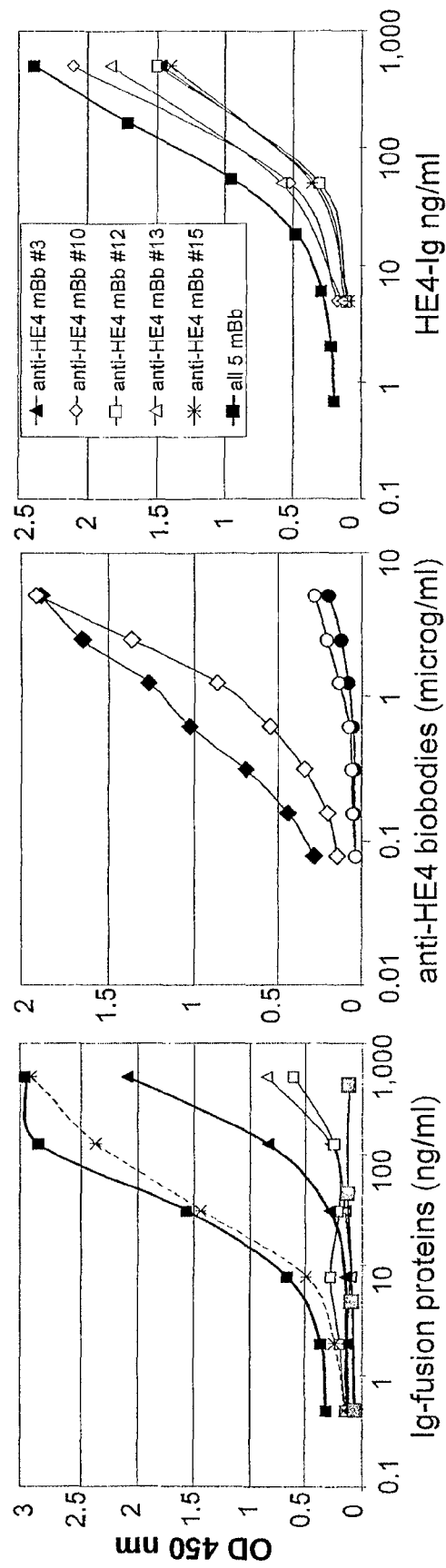

VECTORS FOR EXPRESSING IN VIVO BIOTINYLATED RECOMBINANT PROTEINS

CROSS-REFERENCE TO RELATED APPLICATION

This application claims the benefit of U.S. Provisional Application No. 60/850,183, filed Oct. 5, 2006, which is hereby incorporated herein by reference in its entirety.

STATEMENT OF GOVERNMENT LICENSE RIGHTS

Research leading to the present invention was supported, at least in part, under National Institutes of Health Grant Number P50 CA83636.07 and National Science Foundation Grant Number CTS-0528605. The Government may have certain rights in the invention.

FIELD OF THE INVENTION

This invention relates to compositions and methods for generating in vivo biotinylated, secreted recombinant polypeptides such as antibodies, or fragments thereof, from yeast cells.

BACKGROUND

Although large numbers of candidate biomarkers for malignant (Etzioni, et al., *Nat. Rev. Cancer* 3:243-52 (2003)), autoimmune (Prince, H. E., *Biomarkers* 10(Suppl. 1):44-9 (2005)), infectious (Zhang, et al., *Science* 298:995-1000 (2002)), neurological (Carrette, et al., *Proteomics* 3:1486-94 (2003)), metabolic (Roelofsen, et al., *J. Cell Biochem.* 93:732-40 (2004); Schwegler, et al., *Hepatology* 41:634-42 (2005)), and cardiovascular (Kittleson and Hare, *Cardiovasc. Med.* 15:130-8 (2005)) diseases have been generated using various high-throughput platforms (Omenn, et al., *Proteomics* 5:3226-45 (2005); Ping, et al., *Proteomics* 5:3506-19 (2005)), the production of high affinity antibodies necessary for biomarker validation remains slow and costly.

For example, CA125 is the most extensively studied biomarker for possible use in the early detection of ovarian carcinoma (Kenemans, P., et al., *Eur. J. Obstet. Gynecol. Reprod. Biol.* 49(1-2):115-24 (1993); Tamakoshi, K., et al., *Gynecol. Obstet. Invest.* 39(2):125-9 (1995); Dorum, A., et al., *Eur. J. Cancer* 32A(10):1645-51 (1996); Eagle, K., et al., *Oncologist* 2(5):324-329 (1997); Fures, R., et al., *Coll. Anthropol.* 23(1):189-94 (1999); and Jacobs, I. J., et al., *Mol. Cell Proteomics* 3(4):355-66 (2004)). CA125 is a mucin-like protein of high molecular mass, estimated from 200 to 20,000 kDa, although smaller subunits have been reported (O'Brien, T. J., et al., *Int. J. Biol. Markers* 13(4):188-195 (1998); Yin, B. W., et al., *J. Biol Chem* 276(29):27371-5 (2001)). CA125 cell surface expression is upregulated when cells undergo metaplastic differentiation into a Mullerian-type epithelium (Feeley, K. M., et al., *Histopathology* 38(2):87-95 (2001)). Although CA125 is conserved in mammals (Nouwen, E. J., et al., *Differentiation* 45(3):192-8 (1990); McDonnel, A. C., et al., *Reproduction* 126(5):615-20 (2003); Duraisamy, S., et al., *Gene* (2006)), there is no available antibody against mouse CA125 which impairs ovarian cancer studies in vivo.

New methods such as high-throughput screening by flow sorting of recombinant antibodies (scFv) displayed by yeast (Feldhaus et al., *Nat. Biotechnol.* 21:163-70 (2003)) can accelerate the identification of antigen specific scFv. However, yeast display scFv need to be converted into soluble and labeled recombinant antibodies for further use in immunoassays.

Biotinylation is a robust labeling method that modifies the lysine residues of target proteins and is routinely achieved in vitro with chemical agents (Bayer and Wilchek, *Methods Enzymol.* 184:138-60 (1990)). The extraordinarily high affinity binding of biotin to streptavidin (dissociation equilibrium constant or $K_d=10^{-15}M$) (Green and Melamed, *Biochem. J.* 100:614-21 (1966)) and extremely slow dissociation rate have been used widely in biochemistry and molecular biology. However, chemical biotinylation is not specific and thus can inactivate lysine residues critical for protein function and conformation (Smith, et al., *Nuc. Acids Res.* 26:1414-20 (1998)). In contrast, in vivo biotinylation is a rare and highly specific post-translational modification (Cronan, J. E., *J. Biol. Chem.* 265:10327-33 (1990)) mediated by endogenous biotin ligases. Specific biotinylation of proteins and recombinant antibodies has been obtained in *E. coli* in vivo (Kipriyanov, et al., *Protein Eng.* 9:203-11 (1996); Sibler, et al., *J. Immunol. Methods* 224:129-40 (1999); Santala and Lamminmaki, *J. Immunol. Methods* 284:165-75 (2004); Warren, et al., *Clin. Chem.* 51:830-8 (2005)) and in vitro with purified biotin ligase (Saviranta, et al., *Biocong. Chem.* 9:725-35 (1998); Cloutier, et al., *Mol. Immunol.* 37:1067-77 (2000)). However, current in vivo biotinylation protocols can only label one protein at a time through lengthy molecular engineering that is not compatible with high-throughput approaches.

SUMMARY

In one aspect, the present invention provides a vector for expressing a secreted biotinylated polypeptide in yeast, the vector comprising (i) an insertion site for inserting a nucleic acid sequence encoding a polypeptide to be expressed, (ii) a yeast secretory leader sequence located adjacent the 5' end of the insertion site, (iii) a nucleic acid sequence encoding a biotin acceptor site for golgi-localized biotin ligase fused to the 3' end or to the 5' end of the insertion site, and (iv) nucleic acid sequences allowing for autonomous replication and selection in yeast and bacteria. In some embodiments, the vector further comprises a nucleic acid sequence encoding a linker fused in frame between the insertion site and the biotin acceptor site that allows flexibility between the biotin accepting site and the inserted polypeptide. In some embodiments, the linker is a human IgA1 hinge.

In another aspect, the present invention provides a vector for expressing recombinant golgi-localized biotin ligase in yeast, the vector comprising (i) a nucleic acid sequence encoding a biotin ligase, (ii) a nucleic acid sequence comprising at least one golgi localization domain operationally linked to the nucleic acid sequence encoding the biotin ligase, and (iii) nucleic acid sequences allowing for autonomous replication and selection in yeast and bacteria. In some embodiments, the biotin ligase is the *E. coli* biotin ligase BirA.

In another aspect, the present invention provides a kit for expressing a secreted, biotinylated polypeptide in yeast, the kit comprising: (1) a first vector for expressing a secreted polypeptide comprising a biotin acceptor site, the first vector comprising: (i) an insertion site for inserting a nucleic acid sequence encoding a polypeptide to be expressed; (ii) a yeast secretory leader sequence located adjacent the 5' end of the insertion site; (iii) a nucleic acid sequence encoding a biotin acceptor site for a golgi-localized biotin ligase fused to the 3' end or the 5' end of the insertion site; and (iv) nucleic acid sequences allowing for autonomous replication and selection in yeast and bacteria; and (2) a second vector for expressing the golgi-localized biotin ligase in yeast, the second vector comprising: (i) a nucleic acid sequence encoding the biotin ligase; (ii) a nucleic acid sequence comprising at least one golgi-localization domain operationally linked to the nucleic acid sequence encoding the biotin ligase; and (iii) nucleic acid sequences allowing for autonomous replication and selection in yeast. In some embodiments of the kit, the first vector further comprises a nucleic acid sequence encoding a linker fused in frame between the insertion site and the biotin acceptor site that allows flexibility between the biotin accepting site and the inserted polypeptide. In some embodiments, the linker is a human IgA1 hinge.

In another aspect, the present invention provides a method for generating in vivo biotinylated, secreted recombinant polypeptides. The method comprises recombinantly co-expressing in a yeast cell (a) a secreted recombinant polypeptide comprising a biotin accepting site; and (b) a biotin ligase, wherein the secreted recombinant polypeptide and the biotin ligase are localized to the golgi of the yeast cell.

In another aspect, the present invention provides a method for generating in vivo biotinylated, secreted recombinant polypeptides with affinity to a target polypeptide. The method comprises: (1) contacting yeast cells expressing a surface display recombinant polypeptide library with a target protein and enriching for yeast cells expressing recognition sequences that bind to the target polypeptide to generate an anti-target yeast display sublibrary; (2) isolating nucleic acid sequences encoding the recognition sequences from the anti-target yeast display sublibrary and introducing said nucleic acid sequences and a first vector for expressing a secreted biotinylated polypeptide into yeast cells, wherein the first vector comprises: (i) an insertion site for inserting the nucleic acid sequences encoding the recognition sequences; (ii) a yeast secretory leader sequence located adjacent the 5' end of the insertion site; and (iii) a nucleic acid sequence coding for a biotin acceptor site for a golgi-localized biotin ligase fused to the 3' or 5' end of the insertion site; (3) identifying clone(s) or a population of yeast cells from the yeast cells generated in accordance with step (2) that secrete polypeptides comprising recognition sequences that bind to the target polypeptide; and (4) expressing in the yeast cells identified in step (3) a golgi-localized biotin ligase. In some embodiments, the first vector further comprises a nucleic acid sequence encoding a linker fused in frame between the insertion site and the biotin acceptor site that allows flexibility between the biotin accepting site and the inserted polypeptide. In some embodiments, the linker is a human IgA1 hinge. In some embodiments, the target polypeptide comprises a biomarker for ovarian cancer. In further embodiments, the recognition sequences comprise antibodies, or antigen binding fragments thereof.

In another aspect, the present invention provides a method of generating in vivo biotinylated, secreted recombinant polypeptides with affinity to at least one biomarker that is differentially expressed in a first sample as compared to a second sample. The method comprises: (1) contacting yeast cells expressing a surface recombinant polypeptide display library with biomarkers derived from a first sample and enriching for yeast cells expressing recognition sequences that bind to at least a portion of the biomarkers derived from the first sample to generate an anti-first sample yeast surface recombinant polypeptide display sublibrary; (2) depleting yeast cells from the anti-first sample yeast surface recombinant polypeptide display sublibrary generated in accordance with step (1) that bind to biomarkers derived from a second sample; (3) isolating nucleic acid sequences encoding the recombinant sequences from the anti-first sample yeast surface recombinant polypeptide display sublibrary generated in accordance with step (2) and introducing said nucleic acid sequences and a first vector for expressing a secreted biotinylated polypeptide into yeast cells, wherein the first vector comprises: (i) an insertion site for inserting the isolated nucleic acid sequence encoding the recombinant polypeptide to be expressed; (ii) a yeast secretory leader sequence located adjacent the 5' end of the insertion site; and (iii) a nucleic acid sequence coding for a biotin acceptor site for a golgi-localized biotin ligase fused to the 3' or 5' end of the insertion site; (4) identifying a population of yeast cells generated in accordance with step (3) that secrete recombinant polypeptides that bind to biomarkers derived from the first sample, but that do not bind to biomarkers derived from the second sample; and (5) expressing in the population of yeast cells identified in step (3) a golgi-localized biotin ligase.

Finally, in another aspect, the present invention provides an antibody or an antigen binding fragment thereof specifically recognizing and binding an epitope of human mesothelin polypeptide, wherein said antibody or antigen binding fragment thereof specifically recognizes at least part of an epitope recognized by a reference scFv comprising a variable region of the heavy chain which is at least 90% identical to SEQ ID NO:37 or SEQ ID NO:38, such as at least 95% identical or at least 99% identical. In some embodiments, the antibody or antigen binding fragment thereof is capable of inhibiting CA125/mesothelin-dependent cell attachment.

The compositions, kits and methods of the invention are useful, for example, for producing yeast secreted, in vivo biotinylated recombinant proteins, such as antibodies, or antigen binding fragments thereof. The resulting biotinylated proteins can be tetramerized in the presence of streptavidin and thus made conformationally stable with high affinity to a binding target. The methods of the invention also facilitate the time and cost efficient generation of large amounts of recombinant proteins or antibodies that may be captured onto streptavidin surfaces, such as plastic plates, protein or antibody arrays, or magnetic or fluorescent beads, thereby eliminating the need for purification from yeast supernatant and chemical biotinylation.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2B is a flow diagram illustrating a method for generating in vivo biotinylated, secreted recombinant polypeptides with affinity for differentially expressed polypeptides, as described in Example 6;

FIG. 4A graphically presents results from an ELISA assay demonstrating that monomeric anti-HE4 biobodies affinity increased after preincubation with streptavidin, as described in Example 3;

FIG. 4B graphically presents results from an ELISA assay demonstrating that the affinity of anti-HE4 monoclonal biobodies increased when they were preincubated with streptavidin together, suggesting a cooperative effect, as described in Example 2;

FIG. 4C graphically presents results from an ELISA assay demonstrating that anti-HE4 monoclonal biobodies used separately or together can complement anti-HE4 mAb to detect HE4-Ig in a sandwich ELISA assay, as described in Example 2;

EXPLANATION OF ABBREVIATIONS USED HEREIN

Figures 1A, 1B:
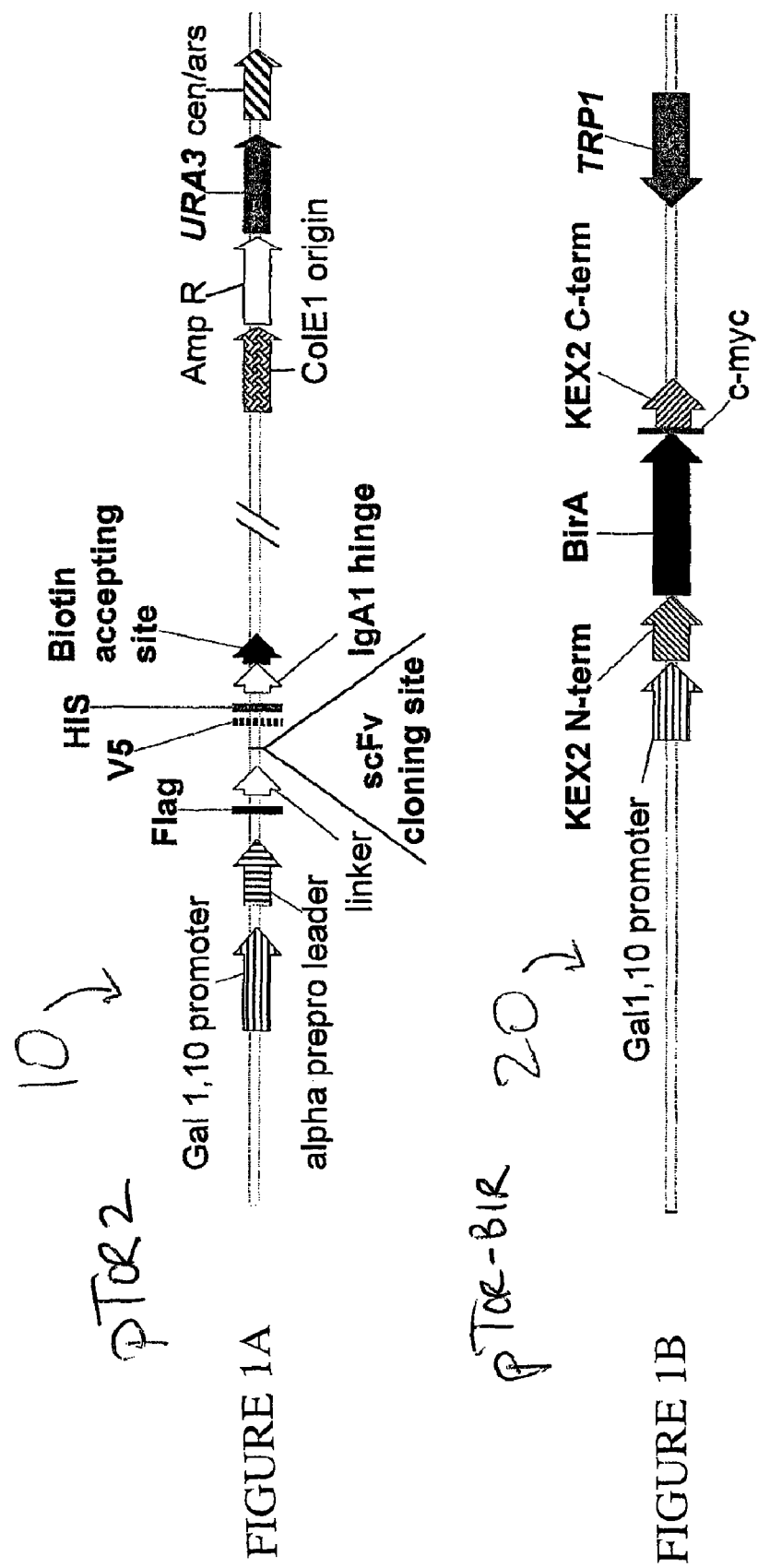
FIG. 1A illustrates the pTOR2 vector (SEQ ID NO:1), an embodiment of a vector for expressing a secreted biotinylated polypeptide in yeast, as described in Example 1.
FIG. 1B illustrates the pTOR-BIR vector (SEQ ID NO:9), an embodiment of a vector for expressing recombinant golgi-localized biotin ligase in yeast, as described in Example 1.

ScFv: single chain Fragment variable; YD: yeast-display; mAb: monoclonal antibodies; Bb: biobodies; mBb: monoclonal biobodies; pBb: polyclonal biobodies; BCCP: biotin acceptor site; BirA: *E. coli* biotin ligase; Ig: immunoglobulin; ON: overnight; RT: room temperature; BSA: bovine serum albumin; PBS: phosphate buffered saline; PBST: PBS supplemented with 0.05% Tween; PCE: PBS supplemented with BSA 0.5% and EDTA 10 mM; PS: penicillin/streptomycin; SA-PE: phytoerythrin-labeled streptavidin; SA-HRP: horseradish peroxidase-labeled streptavidin.

DETAILED DESCRIPTION

Unless specifically defined herein, all terms used herein have the same meaning as they would to one skilled in the art of the present invention. Practitioners are particularly directed to Sambrook, et al., *Molecular Cloning: A Laboratory Manual*, 3d ed., Cold Spring Harbor Press, Plainsview, N.Y. (2000), for definitions and terms of the art.

The following definitions are provided in order to provide clarity with respect to the terms as they are used in the specification and claims to describe the present invention.

As used herein, the term "gene" refers to a nucleic acid (e.g., DNA or RNA) sequence that comprises coding sequences necessary for the production of an RNA and/or a polypeptide, or its precursor as well as noncoding sequences (untranslated regions) surrounding the 5' and 3' ends of the coding sequences. The term "gene" encompasses both cDNA and genomic forms of a gene. A functional polypeptide can be encoded by a full length coding sequence or by any portion of the coding sequence as long as the desired activity or functional properties (e.g., enzymatic activity, ligand binding, signal transduction, antigenic presentation) of the polypeptide are retained. The sequences which are located 5' of the coding region and which are present on the mRNA are referred to as 5' untranslated sequences ("5'UTR"). The sequences which are located 3' or downstream of the coding region and which are present on the mRNA are referred to as 3' untranslated sequences, or ("3'UTR").

As used herein, the term "polypeptide" or "protein" are used interchangeably to refer to polymers of amino acids of any length. A polypeptide or amino acid sequence "derived from" a designated protein refers to the origin of the polypeptide.

As used herein, the term "biomarker" refers to any biological molecule including, but not limited to, polypeptides, proteins, glycoproteins, lipids, lipopolysaccharides, fatty acids, carbohydrates, sugars, endogenous enzymes, such as kinases, cell membrane structures, cytoplasmic molecules, including any post-translational modification of the biological molecule. In accordance with some embodiments of the invention, a biomarker is found in an increased amount in a first sample, (e.g., cell, tissue, body fluid) as compared to a control sample, which may suggest the presence of a disease or condition in the source of the first sample.

As used herein, the term "operatively linked" refers to a juxtaposition wherein the components so described are in a relationship permitting them to function in their intended manner. For example, a promoter sequence is operatively linked to a coding sequence if the promoter sequence promotes transcription of the coding sequence.

As used herein, the term "biobody" refers to a secreted, in vivo biotinylated recombinant polypeptide.

As used herein, the term "antibody" encompasses antibodies and antibody fragments thereof, derived from any antibody-producing mammal (e.g., mouse, rat, rabbit, camelid and primate including human), that specifically bind to a polypeptide target of interest, or portions thereof.

As used herein, the term "antigen binding fragment" refers to the antigen binding or variable region from or related to a full-length antibody. Illustrative examples of antibody fragments include Fab, Fab', F(ab)$_2$, F(ab')$_2$ and Fv fragments, scFv fragments, diabodies, nanobodies, linear antibodies, single-chain antibody molecules and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, the term "epitope tag" refers to a contiguous sequence of amino acids specifically bound by an antibody when fused to another protein.

As used herein, the term "vector" is a nucleic acid molecule, preferably self-replicating, which transfers and/or replicates an inserted nucleic acid molecule into and/or between host cells.

As used herein, the term "nucleic acid sequences allowing for autonomous replication" refers to a polynucleotide comprising an origin of replication (generally referred to as an ori sequence) which allows for replication of the polynucleotide in the appropriate host cell.

As used herein, the term "nucleic acid sequences allowing for selection" refers to polynucleotides encoding any protein that provides a phenotypic marker, for example, a protein that is necessary for cell growth, or resistance to a toxin, or a protein providing a surface antigen for which specific antibodies/ligands are available. Non-limiting examples include amino acid biosynthetic genes (e.g., yeast LEU2, HIS3, LYS2, or TRP1), the URA3 gene, or reporter genes that encode proteins detectable by a suitable assay.

As used herein, the term "affinity maturation" refers to a cycle of mutation and selection to produce antibodies, or antigen binding fragments thereof, which bind their targets more tightly.

As used herein, the term "percent identity" or "percent identical", refers to the percentage of amino acid residues in a polypeptide sequence that are identical with the amino acid sequence of a specified molecule (such as the amino acid sequence of SEQ ID NO:37), after aligning the sequences to achieve the maximum percent identify. For example, the Vector NTI Advance™ 9.0 may be used for sequence alignment.

The present invention provides a cost- and time-effective method to generate yeast-secreted, in vivo biotinylated recombinant proteins (also referred to as "biobodies"). In one embodiment, the method utilizes a vector system that targets BirA anchorage to the yeast secretory compartment using localization signals from the yeast KEX2 protease. KEX2 protease modifies the yeast mating pheromone alpha-factor (MF alpha L) as it is secreted (Wilcox, et al., *Mol. Biol. Cell* 3:1353-71 (1992)). In one embodiment the yeast-secreted proteins in the vector system are under the control of the leader region of MF alpha L precursor ("alpha prepro leader") and also contain a biotin accepting site (BCCP) so that the BirA is targeted to the region of the yeast secretory compartment where it acts on BCCP-fused proteins during their secretion.

This technology is illustrated by producing secreted, in vivo biotinylated recombinant antibodies ("biobodies"), directed against the ovarian cancer marker HE4 (Schummer, et al., *Gene* 238:375-85 (1999)), as described in Examples 2-3, and is further illustrated by producing biobodies directed against mesothelin (Chang, K., et al., *Proc. Natl. Acad. Sci USA* 93(1):136-40 (1996)) that bind to both membrane-bound and soluble mesothelins and block CA125/mesothelin-dependent cell attachment, as described in more detail in Examples 4-5. The anti-HE4 biobodies were validated by ELISA assays, flow cytometry analysis and western blot. It was also determined by Surface Plasmon Resonance (SPR) sensor that the dissociation equilibrium constant of the anti-HE4 biobodies was $5.1 \times 10^{-9}$ M prior to any maturation and/or purification.

In accordance with the foregoing, in one aspect, the present invention provides a vector for expressing a secreted biotinylated polypeptide in yeast. The vector in accordance with this aspect of the invention comprises (i) an insertion site for inserting a nucleic acid sequence encoding a polypeptide to be expressed, (ii) a yeast secretory leader sequence located adjacent the 5' end of the insertion site, (iii) a nucleic acid sequence encoding a biotin acceptor site for golgi-localized biotin ligase fused to the 3' end of the IgA1 linker, (iv) the insertion site fused to the 5' end of the IgA1 linker, and (v) nucleic acid sequences allowing for autonomous replication and selection in yeast and bacteria.

FIG. 1A illustrates an exemplary embodiment of a vector 10 for expressing a secreted biotinylated polypeptide in accordance with this aspect of the invention. The vector 10 includes an insertion site for the insertion of a nucleic acid sequence encoding any recombinant polypeptide of interest, such as, for example, an antibody or antigen binding fragments thereof, such as "single-chain Fv" or "scFv". For example, once scFv are identified that bind to a target of interest in a screening assay using a yeast display scFv library, the scFv may be converted into soluble and labeled recombinant antibodies for further use in immunoassays using the vectors and methods of the invention.

The nucleic acid sequence encoding a polypeptide of interest may be inserted into the insertion site of the vector 10 using any suitable method. In some embodiments, the insertion site is flanked by one or more restriction enzyme sites for insertion of a coding sequence encoding a polypeptide of interest using standard cloning methods. In some embodiments, the vector 10 includes gap repair sequences immediately adjacent the 5' and 3' of the insertion site, and the nucleic acid sequence encoding the polypeptide of interest is cloned into the insertion site using the endogenous homologous recombination system present in yeast, known as "Gap-repair," as described in Orr-Weaver, et al., *Proc. Natl. Acad. Sci. USA* 80:4417 (1983). In brief, Gap repair is an endogenous homologous recombination system in *S. cerevisiae* that allows gene insertion in plasmids at exact sites by utilizing as little as 30 base pair regions of homology between the gene of interest and its target site (the vector 10). Thus, by co-transforming the yeast with a linearized vector 10 (e.g., pTOR2; SEQ ID NO:1) containing a selectable marker and an autonomously replicating sequence along with a PCR product that spans the gap in the vector, in vivo homologous recombination between the vector 10 and the PCR product (e.g., a cDNA insert) results in a circular plasmid containing the cDNA fused to a biotin accepting sequence that can efficiently propagate, without the necessity of in vitro ligation. In addition, gap repair makes it possible to efficiently insert multiple PCR products into a vector such as the vector 10, thus to convert in a time- and cost-effective manner cDNA pools of recognition sequences into yeast-secreted recombinant antibodies, creating a reagent similar to a polyclonal antibody but from which non-specific binders can be removed as described herein.

In the embodiment of the vector 10 shown in FIG. 1A, a promoter sequence, such as GAL1, capable of directing expression of nucleic acids in yeast is operatively linked to 5' end of the insertion site. The GAL1 promoter is a tightly regulated promoter that does not allow any detectable polypeptide expression in the absence of galactose.

The vector 10 also includes a yeast secretory leader sequence located adjacent the 5' end of the insertion site. Any secretory leader sequence may be used that directs the recombinant polypeptide into the yeast secretory compartment. In the embodiment of the vector 10 shown in FIG. 1A, the yeast secretory leader comprises the alpha prepro leader sequence (bp 512-766 of SEQ ID NO:1). Zsebo, et al., *J. Biol Chem* 5:5858-65 (1986)).

The vector 10 includes a nucleic acid sequence encoding a biotin acceptor site for a golgi-localized biotin ligase that is fused to the 3' end of the insertion site. The biotin acceptor site is capable of becoming biotinylated in vivo in the presence of a biotin holoenzyme synthetase. In vivo biotinylation is a highly specific post-translational modification mediated by endogenous biotin ligases (Cronan, J. E., et al., *J. Biol. Chem.* 265:10327-33 (1990)). In one embodiment of the vector 10, the biotin ligase acceptor site is a target for the *E. coli* biotin carboxyl carrier protein (BCCP), a subunit of acetyl-CoA carboxylase (Samols, et al., *J. Biol Chem.* 263:6461-4 (1988)). The gene product of BirA (Barker and Campbell, *J. Mol. Biol.* 146:451-67 (1981)), the biotin holoenzyme synthetase (BirA) (SEQ ID NO:10), catalyzes biotin activation by covalently joining biotin with ATP to form biotin-5'-adenylate, with subsequent transfer to the epsilon amino group of a specific BCCP lysine residue (Barker and Campbell, *J. Mol. Biol.* 146:469-92 (1981b)). Because in vivo biotinylation is highly specific for the BCCP lysine, it can be achieved without modification of critical lysine residues belonging to antibody recognition sequences and thus without functional loss of the recognition domains. BirA typically recognizes a large protein domain, but Schatz and colleagues have identified short peptides (Schatz, P. J., *Biotechnology* 11:1138-43 (1993); Beckett, et al., *Protein Sci.* 8:921-9 (1999)) that efficiently mimic BCCP biotin acceptor function. Accordingly, in one embodiment, the vector 10 comprises a biotin ligase acceptor site comprising GLNDIFEAQKEWHE (SEQ ID NO:7), encoded by SEQ ID NO:8.

In some embodiments, the vector 10 further comprises a linker, such as the human IgA1 hinge sequence comprising SEQ ID NO:5, encoded by SEQ ID NO:6, which is positioned in-frame between the insertion site and the biotin acceptor site, as shown in FIG. 1A. The linker is preferably of human origin to avoid an immune response if the secreted polypeptide were to be used as a therapeutic or imaging tool in human subjects. The linker should be very flexible and positioned between the recognition and the biotin accepting site sequences to reduce polypeptide (e.g., scFv) conformational changes due to biotinylation or to binding mediated by biotin/streptavidin interactions. For example, as described in Example 3, the overall affinity of an anti-HE4 scFv subtractive library displayed by yeast, generated as described in Example 2, found to be in the nanomolar range, did not decrease after conversion into soluble in vivo biotinylated recombinant antibodies.

In one embodiment, the present invention provides a linker that is a recombinant polypeptide comprising a human IgA1 hinge (SEQ ID NO:4) fused to a biotin accepting site (SEQ ID NO:7).

As further shown in FIG. 1A, in some embodiments, the vector 10 further comprises one or more epitope tags operationally linked to the insertion site to express a polypeptide fusion with the polypeptide expressed by the vector 10. Suitable epitope tags are well known in the art, and include, for example, FLAG tag (SEQ ID NO:3, encoded by SEQ ID NO:4); V5, and/or HIS tag, shown in FIG. 1A, and included in pTOR2 (SEQ ID NO:1). The one or more epitope tags may be used to selectively enrich and/or deplete yeast cells, in accordance with various embodiments of the methods of the invention described herein.

In one embodiment, the vector 10 comprises pTOR2 (SEQ ID NO:1), shown in FIG. 1A, which may be generated as described in Example 1. pTOR2 (SEQ ID NO:1) includes the GAL promoter (bp 6-260), the alpha prepro leader (bp 512-766), the FLAG epitope tag (encoded by bp 779-799), the V5 epitope tag (encoded by bp 863-904), the HIS epitope tag (encoded by bp 914-931), the human IgA1 hinge (encoded by bp 932-985), and a biotin accepting site (BCCP) (encoded by bp 986-1030).

In another embodiment, the invention provides a vector for expressing recombinant golgi-localized biotin ligase in yeast. The vector in accordance with this aspect of the invention comprises (i) a nucleic acid sequence encoding a biotin ligase; (ii) a nucleic acid sequence comprising at least one golgi-localization domain operationally linked to the nucleic acid sequence encoding the biotin ligase; and (iii) nucleic acid sequences allowing for autonomous replication and selection in yeast.

FIG. 1B illustrates an exemplary embodiment of a vector 20 for expressing recombinant golgi-localized biotin ligase in yeast in accordance with this aspect of the invention. The embodiment of the vector 20 shown in FIG. 1B includes nucleic acid sequences that encode *E. coli* biotin ligase (BirA) (SEQ ID NO:10) (Howard, et al., *Gene* 35:321-31 (1985)) fused to yeast KEX2 N-terminal leader (SEQ ID NO:15) and KEX2 C-terminal leader (SEQ ID NO:18) golgi-localization domains (Fuller, R. S., *Science* 246:482-6 (1989); Wilcox, et al., *Mol. Biol. Cell* 3:1353-71 (1992)), so that BirA can catalyze the biotin transfer to the recognition sequence-fused Biotin accepting site (BCCP) (SEQ ID NO:7) encoded by the vector 10 for expressing a secreted biotinylated polypeptide, shown in FIG. 1A, within the yeast secretory compartment.

KEX2 protease modifies the yeast mating pheromone alpha-factor (MF alpha L) as it is secreted (Wilcox, et al., *Mol. Biol. Cell* 3:1353-71 (1992)), and the N-terminal and C-terminal golgi-targeting sequences have been defined by deletion studies as described in Fuller, R. S., et al., *Science* 246:482-6 (1989); Wilcox, et al., *Mol. Biol. Cell* 3:1353-71 (1992). While the vector 20 illustrated in FIG. 1B includes the golgi-targeting domains of KEX2, it will be understood by those of skill in the art that any yeast golgi-localization domain may be fused to *E. coli* biotin ligase to direct it to the secretory compartment. For example, other golgi-localization domains have been described in yeast, such as alpha 1-3 mannotransferase (Graham, T. R., et al., *Mol. Biol. Cell* 6(7):809-24 (1995); KRE2 (Lussier, M., et al., *J. Cell Biol.* 131 (4):913-27 (1995)); Guanosine diphosphatase (Vowels, J. J., et al., *Mol. Biol. Cell* 9(6):1351-65 (1998)); EMP47 (Schroder, S., et al., *J. Cell Biol.* 131(4):895-912 (1995)); and TAP/p115 (Bacik, I., et al., *J. Immunol.* 152(2):381-7 (1994); Nelson, D., et al., *J. Cell Biol.* 143(2):319-31 (1998)).

In one embodiment, the vector 20 comprises SEQ ID NO:9, identified as (pTOR-BIR) FIG. 1B. As demonstrated in FIG. 5A and FIG. 5B, and described in Example 2, Western blots confirmed that yeast cells carrying the vector 10 comprising a nucleic acid sequence encoding a polypeptide to be expressed, and carrying the vector 20 expressing recombinant golgi-localized biotin ligase are capable of secreting in vivo biotinylated polypeptides.

In another embodiment, the vector 10 may further comprise one or more elements of vector 20, such that a single vector comprises: (i) an insertion site for inserting a nucleic acid sequence encoding a polypeptide to be expressed, (ii) a yeast secretory leader sequence located adjacent the 5' end of the insertion site, (iii) a nucleic acid sequence encoding a biotin acceptor site for golgi-localized biotin ligase fused to the 3' end or 5' end of the insertion site; (iv) a nucleic acid sequence encoding a biotin ligase; (v) a nucleic acid sequence comprising at least one golgi-localization domain operationally linked to the nucleic acid sequence encoding the biotin ligase; and (vi) nucleic acid sequences allowing for autonomous replication and selection in yeast and bacteria.

In another aspect, the present invention provides a kit for expressing a secreted, biotinylated polypeptide in yeast, the kit comprising: (1) a first vector for expressing a secreted polypeptide comprising a biotin acceptor site, the first vector comprising: (i) an insertion site for inserting a nucleic acid sequence encoding a polypeptide to be expressed; (ii) a yeast secretory leader sequence located adjacent the 5' end of the insertion site; (iii) a nucleic acid sequence encoding a biotin acceptor site for a golgi-localized biotin ligase fused to a flexible linker at the 3' or 5' end of the insertion site; and (iv) nucleic acid sequences allowing for autonomous replication and selection in yeast; and (2) a second vector for expressing the golgi-localized biotin ligase in yeast, the second vector comprising: (i) a nucleic acid sequence encoding the biotin ligase; (ii) a nucleic acid sequence comprising at least one golgi-localization domain operationally linked to the nucleic acid sequence encoding the biotin ligase; and (iii) nucleic acid sequences allowing for autonomous replication and selection in yeast and bacteria In another embodiment, the present invention provides a kit for expressing a secreted, biotinylated polypeptide in yeast, the kit comprising a single vector for expressing a secreted polypeptide comprising (i) an insertion site for inserting a nucleic acid sequence encoding a polypeptide to be expressed; (ii) a yeast secretory leader sequence located adjacent the 5' end of the insertion site (iii) a nucleic acid sequence encoding a biotin acceptor site for a golgi-localized biotin ligase fused to a flexible linker at the 3' or 5' end of the insertion site; (iv) a nucleic acid sequence encoding a promoter for the biotin ligase suc has an internal ribosome entry segment (IRES); (v) nucleic acid sequence encoding the biotin ligase; (vi) a nucleic acid sequence comprising at least one golig-localization domain operationally linked to the nucleic acid sequence encoding the biotin ligase; and (vii) nucleic acid sequences allowing for autonomous replication and selection in yeast and bacteria.

Each kit is preferably provided in suitable packaging and may also contain reagents useful for generating a secreted, biotinylated polypeptide in yeast, such as, for example, yeast strains, selective media, control inserts, sequencing primers and PCR amplification primers, dNTPs, high fidelity polymerase and buffer, reagents for yeast DNA extraction, detection reagents, instructions, and the like. In some embodiments, the kit includes yeast cells transformed with one or more vector(s) of the kit.

In another aspect, the present invention provides a method for generating in vivo biotinylated, secreted recombinant polypeptides. The method comprises recombinantly co-expressing in a yeast cell (a) a secreted recombinant polypeptide comprising a biotin accepting site; and (b) a biotin ligase, wherein the secreted recombinant polypeptide and the biotin ligase are localized to the golgi of the yeast cell. The methods of this aspect of the invention may be carried out using the vectors and kits described herein.

In some embodiments, the method in accordance with this aspect of the invention includes the step of (1) introducing into yeast cells a nucleic acid molecule comprising a nucleotide sequence encoding a recombinant polypeptide of interest and a first vector (10) for expressing a secreted biotinylated polypeptide in yeast. The nucleic acid molecules may be introduced into the yeast cells by standard yeast transformation methods. See e.g., Sambrook et al., *Molecular Cloning: A Laboratory Manual,* 3d Ed., Cold Spring Harbor Press, Plainsview, N.Y. (2000). The transforming DNA may or may not be integrated into the genome of the yeast cell. Upon the co-transformation of the linearized vector 10 and the nucleic acid molecule into a yeast cell, the nucleic acid molecule is inserted into the insertion site via gap repair, an endogenous homologous recombination system in *S. cerevisiae.*

Alternatively, conventional cloning methods may be used to insert the nucleic acid molecule encoding the polypeptide of interest into the insertion site using restriction enzymes, or PCR cloning, followed by transformation of the vector 10 containing the nucleic acid sequence in the insertion site into yeast cells.

The supernatants of yeast cells generated in accordance with step (1) are then assayed for the presence of secreted recombinant polypeptides, and clone(s) or a population of yeast expressing the secreted recombinant polypeptides are isolated. The presence of secreted recombinant polypeptides may be determined using any suitable assay that detects the biomarker, either with the use of a specific binding agent, or an agent that detects one or more epitope tags fused to the polypeptide. A variety of techniques are available in the art for protein analysis. These include, but are not limited to, ELISA (enzyme-linked immunosorbent assays), protein or antibody arrays, Western blot analysis, flow cytometry, and the like.

Once a population of yeast cells are identified that secrete the polypeptide of interest, a second vector (20) expressing golgi-localized biotin ligase is introduced into the identified population of yeast cells. The vector 20 may be introduced via transformation, or by mating as described below.

In one embodiment of the method, the yeast cells transformed in step 1 are haploid yeast cells of a first mating type which carry the vector 10 comprising the nucleotide sequence encoding the recombinant polypeptide of interest fused to a biotin acceptor site at the C-terminus, and optionally containing a flexible linker such as an IgA1 hinge fused in frame therebetween. The vector 20 comprising BirA fused to KEX2 golgi-localization domains is carried in haploid yeast cells of the opposite mating type. The vector 20 is introduced via mating of the two yeast and resulting diploid yeast secrete the recombinant biotinylated polypeptides. The fact that yeast mates by cell fusion makes it easy to combine yeast of one mating type encoding golgi-localized BirA (e.g., carrying the vector 20; such as pTOR-BIR; SEQ ID NO:9) with yeast of the opposite mating type carrying the vector 10 with an insert encoding a polypeptide of interest to form diploids able to secrete biobodies.

The selection of transformants and diploid yeast are done using standard protocols with selection markers such as uracil and tryptophan. For example, in some embodiments, the recipient yeast strains are auxotrophic for tryptophan and uracil because they are mutant for the TRP1 or URA3 genes. When transformed with plasmids carrying the wild type versions of these genes, the yeast transformants are able to grow on medium lacking tryptophan or uracil. Similarly, when a strain carrying a TRP-marked plasmid is mated with a strain carrying a URA3- marked plasmid, the resulting diploid is able to grow on medium lacking both tryptophan and uracil.

The yeast cells containing the vector 10 and the vector 20 are then cultured and the in vivo biotinylated, secreted recombinant polypeptide (biobodies) of interest may be isolated either as a pool to generate polyclonal biobodies, or the yeast cells may be individually plated and screened to identify monoclonal biobodies.

The in vivo biotinylated, secreted recombinant polypeptides (biobodies) may be isolated from the supernatant of the yeast cells using a variety of techniques, including standard protocols using nickel columns to purify Histidine-tagged proteins or monovalent avidin columns to purify biotinylated proteins. For example, in one embodiment, biobodies contain a HIS6 tag which allows them to be isolated from medium by binding to nickel-coated resin. The biobodies can also be collected from the yeast culture medium by binding onto antibody-coated beads using antibodies against the biotin or one or more epitope tags. Similarly, the biobodies can be collected on a streptavidin-coated surface. The biobodies may also be isolated using standard protein purification techniques such as liquid chromatrography.

For example, the biobodies may be isolated from yeast supernatant by binding to streptavidin. The biobodies are tetramerized in the presence of streptavidin and thus made conformationally stable with a higher affinity for the target polypeptide. Several groups have demonstrated independently that biotinylated recombinant antibodies tetramerize in presence of streptavidin and that tetramers show both higher affinity constants and lower non-specific binding than monomeric single chains (Muhlrad, et al., *Yeast* 8:79-82 (1992); Saviranta, et al., *Bioconj. Chem.* 9:725-35 (1998); Cloutier, et al., *Mol. Immunol.* 37:1067-77 (2000)).

Any yeast, such as *S. cerevisiae*, or *Pichia pastoris* may be used in accordance with the various embodiments of the invention. See Faber et al., Review: "Methylotrophic yeasts as factories for the production of foreign proteins," *Yeast* 11:1331-1344 (1995). For example, the method of the invention may be practiced using the yeast strain BJ5464 (MAT-alpha, ura3-52, trp1, leu2δ200, his3δ200, pep4::HIS3, prb1.6R, can1, GAL), available from the A.T.C.C., or a protease modified version of this strain, as described in Jones, E. W., *Methods Enzymol* 185:372-86 (1990). Another example of a suitable yeast strain for use in the present invention is BJ5475 (MAT-a, ura3-52, trp1, his3δ200, pep4::HIS3, prbδ1.6, can1, GAL), also available from the A.T.C.C.

The yeast cells may be stored for travel in growth media, or as a pellet at room temperature for storage shorter than 2 weeks, or any other suitable storage method (e.g., lyophilized, a stab in agar medium, or as a glycerol stock) in order to facilitate ease of transport and low cost production of biobodies with minimal facility requirements. Secreted biobodies do not require purification from the yeast culture media, and as demonstrated in Example 3, purified and non-purified biobodies yield the same antigen-specific affinity after immobilization on streptavidin arrays as measured by SPR. See also Scholler, et al. (2006). Similar data have been generated by bead-based assays, see Table 1 and Example 3.

Thus, the methods may be used to generate reagents for use in ELISA, flow cytometry, or bead-based assays or in antibody or protein arrays for a very low cost. Conformationally stable and high affinity recombinant antibodies also permit immunoprecipitations and thus the development of original tools for biomarker discovery.

In another aspect, the present invention provides a method for generating in vivo biotinylated, secreted recombinant polypeptides with affinity to a target polypeptide, otherwise referred to as a "biomarker". The methods according to this aspect of the invention may be carried out using the vectors described herein. For illustrative purposes, the method is described below with reference to the generation of scFv recombinant polypeptides that bind to the HE4 antigen, however, it will be understood by those of skill in the art that any biotinylated, secreted polypeptide with affinity to a biomarker may be generated according to this method.

Figure 2A:
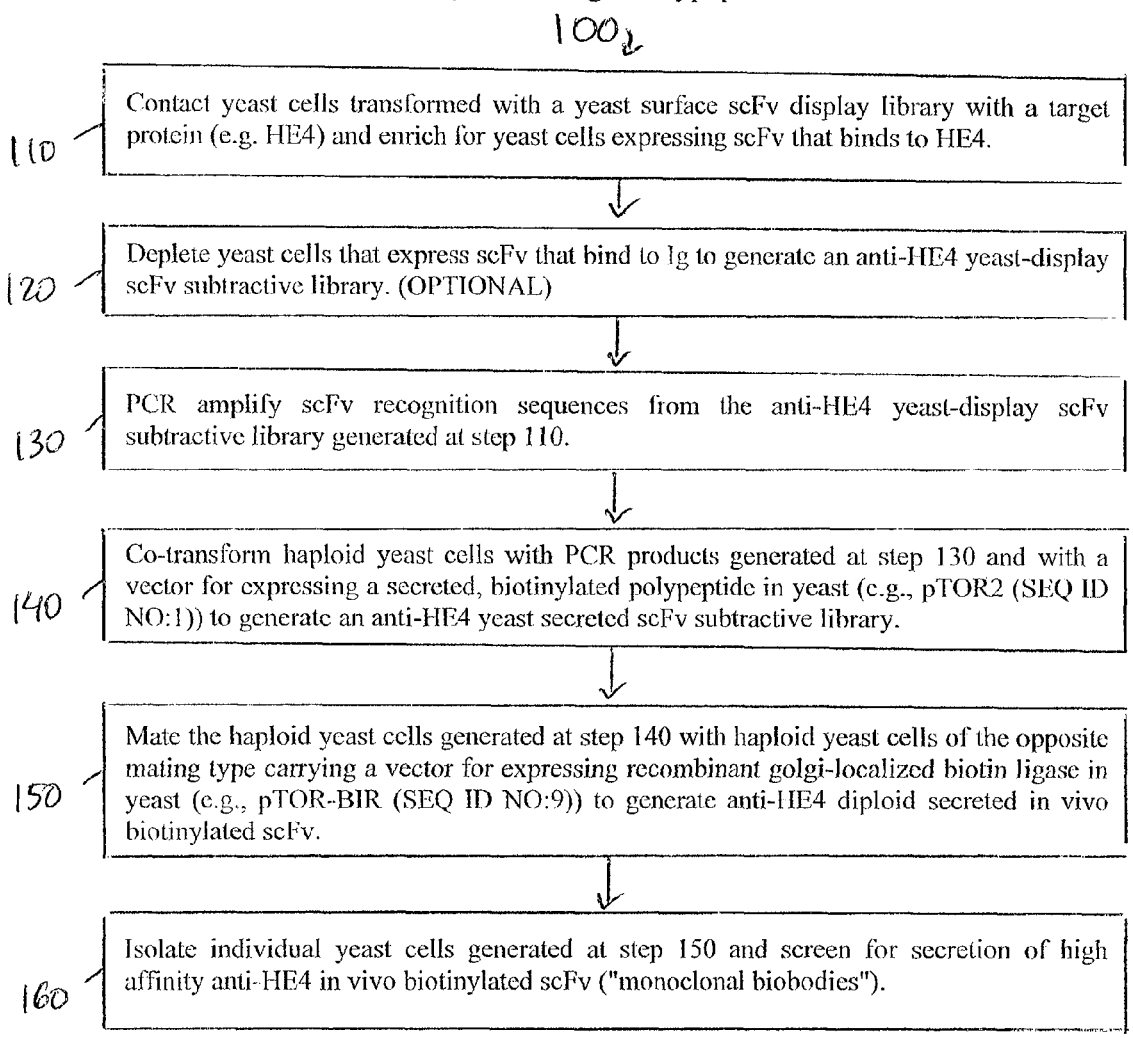
FIG. 2A is a flow diagram illustrating a method for generating in vivo biotinylated, secreted recombinant polypeptides with affinity for a target polypeptide, in accordance with an embodiment of the invention, as described in Example 2.

FIG. 2A is a flow diagram illustrating an embodiment of the method in accordance with this aspect of the invention. The method 100 includes the step 110 of bringing yeast cells transformed with a yeast surface display library into contact with a target biomarker (e.g., a protein) and enriching for yeast cells expressing scFv recognition sequences that bind to the biomarker to generate an anti-target yeast display sublibrary. Any surface display library may be used in accordance with the methods of the invention. Non-limiting examples of surface display libraries suitable for use in various embodiments of the invention include a yeast surface scFv display library, a phage display scFv library (Tan, et al., *J Clin Virol* 38(1):49-56 (2007); Hoogenboom, et al., *Immunotechnology* 4(1):20 (1998)); or a bacterial flagella display peptide library (Westerlund-Wikstrom, et al., *Int J Med Microbiol* 290(3): 223-30 (2000)). The target biomarker may be any biological molecule. In some embodiments the target biomarker is a protein biomarker associated with cancer, such as the HE4 (e.g., as described in Examples 2 and 3), or mesothelin (e.g., as described in Examples 4 and 5 herein).

The cells expressing the recognition sequences are selected based on affinity to the target biomarker using any suitable selection method, such as flow cytometry, and/or magnetic sorting techniques and/or cell panning as described herein to produce a sublibrary enriched for the expression of recognition sequences. Multiple rounds of enrichment may be carried out. Enrichment can be measured as an increasing fraction of cells binding to a biomarker in each round of selection. For example, enrichment may be measured by flow cytometry analysis as the percentage of yeast expressing recognition sequences (e.g., scFv) that bind to the target biomarker. Increasing enrichments using the method are preferred, such as at least 5% of biomarker-binding yeast after 2 magnetic sortings and 2 flow sortings, or at least 50% of biomarker-binding yeast after 2 magnetic sortings and 3 flow sortings.

At 120, the method optionally includes the step of depleting yeast cells that express scFv that bind to a non-target biomarker, such as Ig, in order to generate an anti-HE4 yeast-display subtractive library. The depletion of yeast cells may be carried out using any suitable method, such as magnetic sorting techniques, as described herein, and also via flow sortings and/or cell pannings.

At 130, the method involves isolating nucleic acid sequences encoding the recognition sequences from the anti-target yeast display sublibrary. For example, the nucleic acid sequences may be PCR amplified from the vector 10 using vector specific 5' and 3' flanking primers, as described in Example 2.

At 140, haploid yeast cells are co-transformed with the nucleic acid sequences isolated at 130 and a first vector (10) for expressing a secreted biotinylated polypeptide into yeast cells, as described herein, to generate an anti-target yeast secreted polypeptide library.

At 150, the haploid yeast cells generated at 140 are mated with haploid yeast cells of the opposite mating type carrying a vector 20 expressing recombinant golgi-localized biotin ligase to generate anti-target diploid-secreted in vivo biotinylated polypeptides. The polypeptides generated at 150 may be pooled for use as polyclonal biobodies.

Finally, at 160, individual yeast cells generated at 150 are plated and screened for secretion of high affinity monoclonal anti-target in vivo biotinylated polypeptides (monoclonal biobodies).

In another aspect, the present invention provides a method of generating in vivo biotinylated, secreted recombinant polypeptides with affinity to at least one biomarker. In accordance with this aspect of the invention, with reference to FIG.

2A, at 140, haploid yeast cells are co-transformed with the nucleic acid sequences isolated at 130 and a first vector (10) for expressing a secreted in vivo biotinylated polypeptide into yeast cells, as described herein, to generate an anti-target yeast secreted polypeptide library.

At 150, the anti-target yeast secreted polypeptide library plated at 140 is arrayed in 96-well plates and high-throughput mated in liquid medium, for example, as described in Bergan et al., submitted in 2007.

Finally, at 160, individual yeast cells generated at 150 are plated and screened for secretion of high affinity monoclonal anti-target in vivo biotinylated polypeptide secreted recombinant polypeptides with affinity to at least one biomarker (monoclonal biobodies).

In another aspect, the present invention provides a method of generating in vivo biotinylated, secreted recombinant polypeptides with affinity to at least one biomarker that is differentially expressed in a first sample as compared to a second sample.

FIG. 2B is a flow diagram illustrating an embodiment of the method 200 in accordance with this aspect of the invention. For illustrative purposes, the method 200 is described below with reference to the generation of scFv recombinant polypeptides that bind to a differentially expressed biomarker; however, it will be understood by those of skill in the art that any biotinylated, secreted polypeptide with affinity to a differentially expressed biomarker may be generated according to this method.

The method 200 includes the step 210 of contacting yeast cells transformed with a yeast surface display scFv library with biomarkers (e.g., biotinylated polypeptides) derived from a first sample and enriching for yeast cells expressing scFv that bind to at least some of the biomarkers (biotinylated polypeptides) to generate an anti-first sample surface display scFv library.

The cells expressing the scFv recognition sequences are selected based on affinity to the biomarkers using any suitable selection method, such as flow cytometry, and/or magnetic sorting techniques as described herein to produce a sublibrary enriched for the expression of recognition sequences. Multiple rounds of enrichment may be carried out.

At 220, yeast cells generated at 210 that bind to biomarkers (biotinylated polypeptides) derived from a second sample are depleted to generate an anti-first sample subtractive surface display scFv library. The depletion of yeast cells may be carried out using any suitable method, such as magnetic sorting techniques, as described herein, or flow sorting, or cell pannings. Differential binding to first and second samples may be assessed by flow cytometry analysis. In a preferred embodiment, more than 50% of yeast expressing scFv differentially bind to first biomarker and second biomarker targets before proceeding to 230.

At 230, nucleic acid sequences encoding scFv recognition sequences are isolated (e.g., PCR amplified) from the yeast cells generated at 220.

At 240, haploid yeast cells are co-transformed with the nucleic acid sequences isolated at 230 and a first vector (10) for expressing a secreted biotinylated polypeptide into yeast cells, as described herein, to generate an anti-first sample subtractive yeast secreted scFv library.

At 250, haploid yeast cells generated at 240 are identified that secrete scFv that bind to biomarkers derived from the first sample, but that do not bind to the biomarkers derived from the second sample.

Alternatively, in some embodiments, such as in applications utilizing immunoprecipitation for comparative mass spectrometry analysis, haploid yeast are mated in liquid to obtain a pool of biobodies. In such embodiments, first and second samples are immunoprecipitated by the biobodies generated at 250 and the eluates are compared by mass spectrometry and data analysis programs such as Computational Proteomics Analysis System (CPAS) as described in Rauch, A., et al., *J. Proteom. Res.* 5(1):112-21 (2006).

At 260, the haploid yeast cells generated at 250 are mated with haploid yeast cells of the opposite mating type carrying a vector 20 expressing recombinant golgi-localized biotin ligase to generate anti-first sample subtractive diploid-secreted in vivo biotinylated scFv. The scFv generated at 260 may be pooled for use as polyclonal biobodies.

Finally, at 270, individual yeast cells generated at 260 are plated and screened for secretion of high affinity monoclonal anti-first sample in vivo biotinylated scFv (monoclonal biobodies), and are confirmed to have low or no binding to biomarkers derived from the second sample.

The first and second samples in accordance with this aspect of the invention may differ by any desired parameter. Exemplary parameters include, disease versus normal cell types, or fluids derived from disease versus control subjects such as blood, cerebrospinal fluid, pleural effusion, peritoneal effusion, nipple aspirate, cystic fluid, urine, fece, saliva, or tears, to generate biobodies that bind to differentially expressed disease biomarkers, present on the cell surface, in the cytoplasm, or in fluids. Disease biomarkers include biological molecules having an expression pattern that is correlated to one or more of the diseases including, but limited to, cancers, infectious diseases, parasitic diseases, metabolic diseases, degenerative diseases, congenital diseases, cardiovascular diseases, and other diseases, or poisoning.

The first and second sample in accordance with this aspect of the invention may also differ by other parameters including different cell types, different bacterial strains (as described in Example 6), cells treated with an agent (e.g., a drug) as compared to untreated cells, or samples obtained from different disease stages (e.g., early versus late, or treatment-sensitive versus treatment-resistant). Because this method does not rely on the knowledge of particular differentially expressed disease biomarkers, it may be used to identify novel differentially expressed disease biomarkers which may be further characterized by isolating the biomarkers bound by the biobodies, as further described in Example 6.

The vectors and methods of various aspects of the present invention may be used to generate in vivo biotinylated, secreted antibodies and antigen binding fragments thereof. For example, the vectors and methods of an embodiment of the present invention were carried out to generate in vivo biotinylated, secreted antigen binding fragments that specifically bind both membrane-bound and soluble forms of mesothelin and block CA125/mesothelin-dependent cell attachment, as described in Example 4 and Example 5 herein.

Mesothelin, (Genbank reference number NC_000016, hereby incorporated by reference), is a 40 kDa protein constitutively expressed at the surface of mesothelial cells (peritoneal cardiac and pleural linings) but also by mesotheliomas and ovarian carcinoma cells (Chang, K., et al., *Proc. Natl. Acad. Sci. USA* 93(1):136-40 (1996)). Mesothelin is also found soluble in mesothelioma and ovarian carcinoma patient sera and urines (Scholler, N., et al., *Proc. Natl. Acad. Sci. USA* 96(20):11531-6 (1999); Robinson, B. W., *Lancet* 362(9396): 1612-6 (2003); Hassan, R., *Clin. Cancer Res.* 12(2):447-53 (2006)). CA125, (Genbank reference number NP_078966, hereby incorporated by reference), is a mucin-like protein of high molecular mass, estimated from 200 to 20,000 kDA, although smaller subunits have been reported (O'Brien, T. J., et al., *Int. J. Biol. Markers* 13(4):188-95 (1998); Yin, B. W., et al., *J. Biol. Chem.* 276(29):27371-5 (2001)). CA125 cell surface expression is upregulated when cells undergo metaplastic differentiation into a Müllerian-type epithelium (Feeley, K. M., *Histopathology* 38(2):87-95 (2001)).

The interaction between mesothelin and CA125 proteins is considered to be an important event in the peritoneal implantation of ovarian tumor cells by promoting cell attachment between CA125-expressing tumor cells and the peritoneal lining that constitutively expresses a membrane bound form of mesothelin (Rump, A., et al., *J. Biol. Chem.* 279:9190-9198 (2004); Gubbels, J. A., et al., *Mol. Cancer* 5:50 (2006); Scholler, N., et al., *Cancer Letters* (2006)). Therefore, the in vivo biotinylated, secreted antigen binding fragments that specifically bind both membrane-bound and soluble forms of mesothelin and block CA125/mesothelin-dependent cell attachment may be useful as therapeutic agents that prevent or delay peritoneal metastases.

In accordance with the foregoing, in another aspect, the invention provides an antibody or an antigen binding fragment thereof specifically recognizing and binding an epitope of human mesothelin polypeptide, wherein said antibody or antigen binding fragment thereof specifically recognizes at least part of an epitope recognized by a reference scFv comprising a variable region of the heavy chain which is at least 90% identical, such as at least 95%, or at least 99% identical to SEQ ID NO:34 or SEQ ID NO:37.

Figure 7:
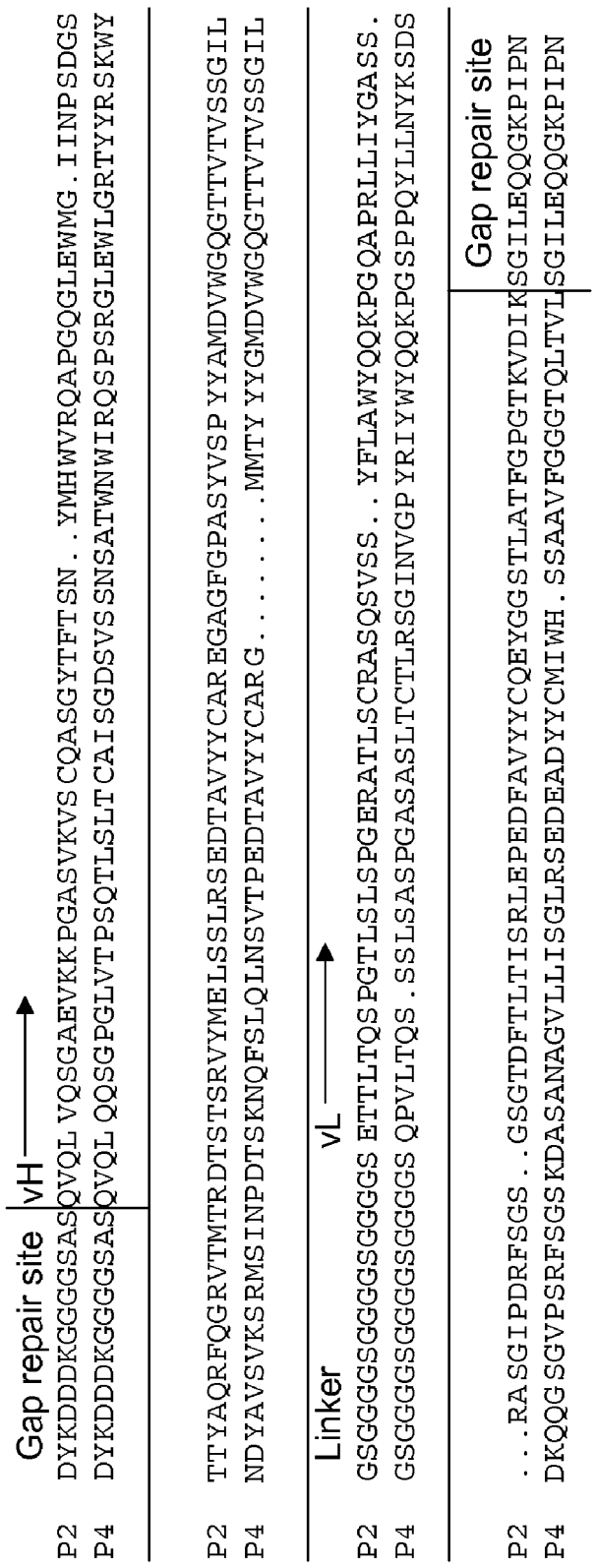
FIG. 7 is a comparison between the consensus sequence of the P2 (SEQ ID NO:33) and P4 (SEQ ID NO:36) scFv groups demonstrating that these were 64% homologous, as described in Example 4.

As described in Example 4 and 5, anti-human mesothelin biobodies were generated using the methods described herein. Three yeast display scFv populations with different binding affinities to mesothelin were identified (P2, P3, and P4), and were seperately sorted by flow cytometry. The consensus sequences of the scFv isolated from the P2 (SEQ ID NO:33) and P4 pool (SEQ ID NO:36) are shown in FIG. 7.

The P2 consensus sequence (SEQ ID NO:33) includes a 5' gap repair site, a variable region of the heavy chain (vH) (SEQ ID NO:34); a linker region, a variable region of the light chain (vL) (SEQ ID NO:35) and a 3' gap repair site.

The P4 consensus sequence (SEQ ID NO:36) includes a 5' gap repair site, a variable region of the heavy chain (vH) (SEQ ID NO:37); a linker region, a variable region of the light chain (vL) (SEQ ID NO:38) and a 3' gap repair site.

The P2, P3 and P4 sorted pools were co-transformed with pTOR2 (SEQ ID NO:1) to obtain yeast able to secret scFv. These yeast were then mated to a yeast strain carrying pTOR-BIR (SEQ ID NO:9) to generate secreted, in vivo biotinylated scFv (biobodies).

As described in Example 5 and shown in FIG. 9, the majority of the secreted in vivo biotinylated scFv biobodies with the consensus sequence of P4 (SEQ ID NO:36) comprising a variable region of the heavy chain (vH) (SEQ ID NO:37); and a variable region of the light chain (vL) (SEQ ID NO:38), significantly interfered with CA125/mesothelin-dependent cell attachment. These results suggest that most scFv P4 biobodies may be used to block or decrease CA125/mesothelin-dependent cell attachment in vivo, and thus could be used as therapeutic agents to prevent or reduce the peritoneal implantation of tumor cells.

The following examples merely illustrate the best mode now contemplated for practicing the invention, but should not be construed to limit the invention.

EXAMPLE 1

This Example describes the generation of a vector system for the production of yeast-secreted, in vivo biotinylated recombinant antibodies, otherwise referred to as "biobodies."

Methods:

Generation of the pTOR2 vector: The pTOR2 vector (SEQ ID NO:1), shown in FIG. 1A, was derived from pNL9 (SEQ ID NO:2) by replacement of the HA tag with a Flag tag, and addition of a human IgA1 linker and of a biotin accepting site. The pTOR2 vector (SEQ ID NO:1) confers uracil-prototrophy (URA3), autonomous replication (cen/ars), and promotes yeast secretion of V5-, flag- and HIS-tagged proteins and, when mated to strain over-expressing golgi-localized biotin ligase, secretion of in vivo biotinylated proteins.

The pTOR2 vector (SEQ ID NO:1) was derived from pNL9 (SEQ ID NO:2) (the kind gift from Pacific Northwest National Laboratory). The following modifications were introduced into the pNL9 vector (SEQ ID NO:2): the HA tag (779-805 bp) was replaced by a Flag tag DYKDDDK (SEQ ID NO:3) (Chubet and Brizzard, *Biotechniques* 20:136-41 (1996)) encoded by gattataaagatgacgataaa (SEQ ID NO:4). The prolinker for human IgA1 hinge PSTPPTPSPST-PPTPSPS (SEQ ID NO:5) (Sumiyama, et al., *Mol. Biol. Evol.* 19:1093-9 (2002)) encoded by ccatcaacaccaccaactccaagtcct-tctactcctcctacaccttcaccatca (SEQ ID NO:6), and the biotin accepting site (BCCP) GLNDIFEAQKEWHE (SEQ ID NO:7) encoded by ggtttgaatgatatttttgaagct-caaaaaattgaatggcatgaawas (SEQ ID NO:8) were cloned in frame distal to the HIS tag (920-937 bp).

Generation of the pTOR-BIR vector: The pTOR-BIR vector (SEQ ID NO:9), shown in FIG. 1B, encodes *E. coli* biotin ligase (BirA) fused to yeast KEX2 N- and C-terminal golgi-localization domains, so that BirA can catalyze the biotin transfer to the recognition sequence-fused BCCP (carried on the pTOR2 vector) within the yeast secretory compartment. pTOR-BIR (SEQ ID NO:9) confers tryptophan-prototrophy (TRP1). Both pTOR2 (SEQ ID NO:1) and pTOR-BIR (SEQ ID NO:9) vectors are under the control of galactose promoter (GAL1,10).

The pTOR-BIR vector (SEQ ID NO:9) was generated as follows:

The *E. coli* biotin ligase sequence (BirA ORF II) (SEQ ID NO:10) (Howard et al., *Gene* 35:321-31 (1985)) was PCR amplified with:

5+BirAHindIII (5'-ctagaagcttgccgccatgaaggataa-caccgtgcc-3') (SEQ ID NO:11) and

3'BirAEcoR1myc (5'-gatgagttttttgttcgaattcttttct-gcactacgcaggg-3') (SEQ ID NO:12) primers from DNA isolated from Top 10' *E. coli* (Invitrogen Corporation, Carlsbad, Calif.) and then ligated into HindII/EcoRI sites of pcDNA3 polylinker (Invitrogen). After sequence verification, BirA was PCR amplified with:

5'BamH1BirA (5'-ctagggatccatgaaggataacaccgtgcc-3') (SEQ ID NO:13) and

3'BirAcmycXho1 (5'-atatctcgagttattacagatcctct-tctgatgagatg-3') (SEQ ID NO:14) primers and ligated into BamH1/XhoI sites of the p414-GAL1 polylinker (the sequence was the kind gift of Martin Funk) between GAL1, 10 promoter and CYC1 terminator (Mumberg, et al., *Nucleic Acids Res* 22:5767-8 (1994)) to create a p414gal1-BirA-cmyc construct.

To redirect BirA into the yeast secretory pathway, KEX2 leader and anchoring domain (Fuller, R. S. and J. Thomer, *Science* 246:482-6 (1989); Wilcox, et al., *Mol. Biol. Cell* 3:1353-71 (1992)) were added to p414gal1-BirA-cmyc at the 5' and 3' ends, respectively, of the BirA coding sequence as follows.

The KEX2 N-terminal leader (SEQ ID NO:15) was PCR-amplified from BY4742 yeast genomic DNA (ATCC, Manassas, Va.) with the following primers:

KEXN forward (5'-catgactagtatgaaagtgag-gaaatatattactttatgcttt-3') (SEQ ID NO:16) and KEXN reverse (5'-attactcgagttatcacgatcgtccggaagatggaggaacatcagg-3') (SEQ ID NO:17) and the PCR fragment was ligated into BAMH1/SpeI sites of p414gal1-BirA-cmyc to create N-KEX2-BIRA c-myc.

The KEX2 C-terminal sequence (SEQ ID NO:18) was amplified from BY4742 DNA with the following primers:

KEXC+cmyc(5'Ctgagaattcgaacaaaaactcatctca-gaagaggatctgtctgagtacgattctactttggacaatg-3') (SEQ ID NO:19) and KEXCrev(5'-attactcgagttatcacgatcgtccg-gaagatggaggaacatcagg-3') (SEQ ID NO:20) primers and was ligated into EcoR1/Xho1 sites of N-KEX2-BIRA c-myc to create pTOR-BIR construct, as shown in FIG. 1B.

All constructs were confirmed by sequencing.

KEX2p is a yeast protease that modifies the mating pheromone of MATalpha yeast as it transits the secretory apparatus; KEX2p is targeted to the golgi apparatus by N-terminal and C-terminal domains. Since scFv secretion is controlled by the alpha pheromone leader sequence of pTOR2, the KEX2 N-and C-terminal localization signals were utilized to target BirA for the secretory compartment. While endogenous yeast biotin ligase and transfected *E. coli* biotin ligase without KEX2 localization domains failed to biotinylate secreted recombinant antibodies, BirA fused to KEX N- and C-domains was able to act on its target site as the biobodies were secreted.

Accordingly, as described in more detail below, the pTOR2 vector (SEQ ID NO:1) and the pTOR-BIR vector (SEQ ID NO:9) have been successfully used in accordance with various embodiments of the methods of the invention to produce in vivo biotinylated, secreted recombinant proteins, such as scFv in yeast.

EXAMPLE 2

This Example demonstrates the use of the vector system to generate biobodies against HE4, a biomarker for ovarian carcinoma.

Rationale: This example describes an embodiment of the method 100, generating biobodies against an exemplary biomarker, HE4. The method 100 is illustrated in FIG. 2A. As shown in FIG. 2A, a HE4-specific yeast-display scFv library was generated by enrichments for HE4-Ig-binding scFv and depletion for Ig-binding scFv (see FIG. 2A, 110, 120). The resulting yeast-display scFv subtractive library was converted into an anti-HE4 yeast-secreted scFv library by homologous recombination in yeast between PCR fragments of scFv recognition sequences and pTOR2 vector (see FIG. 2A, 130, 140). Uracil-prototrophic tryptophan-auxotrophic transformed yeast that secreted anti-HE4 yeast-secreted scFv were then mated with tryptophan-prototrophic uracil-auxotrophic yeast that carried pTOR-BIR (see FIG. 2A, 150). Resulting uracil/tryptophan-prototrophic diploid cells, selected on medium lacking both tryptophan and uracil, secreted in vivo biotinylated scFv (biobodies) of monoclonal (mBb) or polyclonal (pBb) origins (see FIG. 2A, 160).

Methods:

Generation of HE4 vector: HE4, (Genbank reference number NP_542772, hereby incorporated by reference), is a biomarker for ovarian carcinoma (Hellstrom, et al., *Cancer Res.* 63:3695-700 (2003)) was amplified from an ovarian tumor cDNA with HE4 forward (5'-ctagagatctatggccttgc-caacggctcga-3') (SEQ ID NO:21) and HE4 reverse (5'-catgc-cgccggaggatggtccgttcaggctg-3') (SEQ ID NO:22) primers to create a sequence flanked by BglII and SacII sites. HE4 PCR products were ligated into BglII/SacII sites of display vector (Invitrogen) in frame with IgK leader, c-myc and HA tags, and the C-terminal transmembrane anchoring domain of platelet-derived growth factor receptor (PDGFR). As negative controls for anti-HE4 biobody specificity, MPF and Mesothelin were PCR amplified from the clone MGC: 10273 IMAGE:3957372 (ATCC) and transfected into HEK293F cell lines (ATCC) to be expressed at the cell surface or secreted as a fusion protein (Meso-Ig) (Scholler, et al., *J. Immunol. Methods* 317:132-143 (2006)). All constructs were confirmed by sequencing.

Generation of anti-HE4 yeast display scFv subtractive library: A yeast-display scFv library (Feldhaus, et al., *Nat. Biotechnol.* 21:163-70 (2003)) was first enriched for scFv that bound to 100 nM of HE4-Ig as follows:

Five hundred micrograms of HE4-Ig (the kind gift of Dr. Martha-Hayden Ledbetter)(Hellstrom, et al., *Cancer Res.* 63:3695-700 (2003)) were biotinylated with EZ-link sulfo-NHSLC biotin kit (Fisher Biotech, Fair Lawn, N.J.) according to manufacturer instructions. Twosuccessive rounds of scFv enrichment with HE4-Ig by magnetic sorting followed by three roundsof flow sorting with BD FACSAria™ cell sorter (BD Biosciences Immunocytometry Systems,San Jose, Calif.) were performed as described in Yeast Display scFv Antibody Library User'sManual, Pacific Northwest National Laboratory, Richland, Wash., version MF031112. In brief, all incubations were carried in 1 ml ofPBE (Phosphate Buffered Saline (PBS) supplemented with 0.5% bovine serum albumin (BSA)(Sigma-Aldrich)) and 4 mM EDTA (Promega Corporation, Madison Wis.) for 30 min at 4° C.Yeast-display (YD) scFv were grown in synthetic selective medium containing 0.5% CasaminoAcids (Fisher) (SD-CAA), 1% penicillin/streptomycin (PS) (Gibco/Invitrogen Corporation,Carlsbad, Calif.). Because of the presence of *Candida parapsilosis* in the PNNL library, 0.250 microg/ml of ketoconazole (Sigma-Aldrich, St. Louis, Mo.) was added after four rounds ofselection. YD scFv expression was induced in selective medium supplemented with 2%galactose, 2% rafinose and 0.1% dextrose (SGR-CAA) and 1% PS.

To remove the anti-HE4-Ig YD scFv that bound to the Ig domain, YD scFv were incubated with 100 nM of biotinylated Meso-Ig and magnetically depleted.YD scFv were incubated with 50 microL of streptavidin magnetic beads (Miltenyi, Auburn, Calif.) for 10 min at 4° C. and pelleted. After one wash with PBE, YD scFv were loaded on LD depletion column (Miltenyi). The effluent and one 7 ml-rinse containing the non-binding yeast were regrown and induced as described above. After a second round of depletion with Meso-Ig, one last round of magnetic enrichment with 50 nM of biotinylated HE4-Ig was performed to generate an anti-HE4 YD scFv subtractive library.

Flow Cytometry: The flow cytometry analysis was carried out as follows: YD scFv were incubated with 2 micrograms/ml of anti-cmyc mAb (Santa Cruz Biotechnology) and 100 nM of biotinylated HE4-Ig or Meso-Ig followed by Alexa Fluor® 488 F(ab')2 fragment of goat anti-mouse IgG (H+L) (488 anti-mIg) (Invitrogen) diluted 1/200 and phytoerythrin-labeled streptavidin (SA-PE) (BD Pharmingen, San Diego, Calif.) diluted 1/100. All incubations were carried in PBE for 30 min at 4° C. Fluorescent signals were detected with a BD FACScan Cytometer. Wild type and transfected-HEK 293 cells were incubated with 5 micrograms/ml of anti-HA mAb (Roche Applied Science, Indianapolis, Ind.), or 5 micrograms/ml of anti-HE4 mAb 3D8 (Hellstrom, et al., *Cancer Res.* 63:3695-700 (2003)) followed by 488 anti-mIg, or 5 micrograms/ml of biobodies premixed with 1/500 SA-PE for 20 min at 4° C. All incubations were performed with 2-5×10$^5$ cells per ml, in 50 microliters of PBE, for 30 min at 4° C. Cells were washed twice with PBE between incubations.

The entire procedure, including enrichment and depletion, required less than 200 micrograms of both Ig-fusion proteins.

Conversion of yeast-display (YD) scFv into yeast-secreted scFv by homologous recombination: To generate anti-HE4 secreted scFv, scFv recognition sequences of anti-HE4 YD scFv subtractive library were PCR-amplified and cotransformed with Not1/Sfi-cut pTOR2 vector (SEQ ID NO:1) into the yeast strain YVH10 (PNNL) to obtain a scFv library capable of secreting anti-HE4 scFv. A detailed description of the methods follow:

One hundred microliters of anti-HE4 YD scFv subtractive library grown to saturation were patched in a 1 cm² on SD-CAA plate and grown 1 day at 30° C. Yeast DNA was isolated (Hoffman and Winston, Gene 57:267-72 (1987)) and used as a template for PCR amplification with the primers pTOR2 forward (5'-gattataaagatgacgataaaggtggtggtggttctgcta-3') (SEQ ID NO:23) and pNL9 reverse (5'-gggttagggataggcttac-cctgttgttctagaattccg-3') (SEQ ID NO:24). The resulting 800 bp PCR products were gel-purified on a Qiaquick gel extraction column according to the manufacturer instructions (Qiagen, Valencia, Calif.). Ten microliters of gel-purified PCR products were cotransformed with 1 microgram of Not1/Sfi1 cut pTOR2 vector (SEQ ID NO:1) into the yeast strain BJ5464 (ATCC), also known as YVH10 (PNNL). Transformants arising by homologous recombination were selected on SD-CAA plates supplemented with 0.008% tryptophan (Sigma-Aldrich) (SD-CAA+TRP). Two hundred to two thousand colonies were recovered per transformation.

To evaluate the ability of KEX2 domains to target BirA expression to the yeast-secretory compartment, pTOR2-scFv yeast transformants were mated with yeast carrying pTOR-BIR (SEQ ID NO:9). As controls, the pTOR2-scFv yeast transformants were also mated with yeast carrying 414-GAL1 vector only or p414gal1-BirA-cmyc ligase that encodes biotin ligase without KEX2 domains. Resulting diploid supernatants were characterized by Western blot and ELISA as follows:

Western Blot Analysis: Samples were separated by electrophoresis on a 4-12% NuPAGE Bis Tris gel (Invitrogen) using SDS running buffer (Invitrogen). Gels were blotted to a PVDF membrane (Invitrogen) in transfer buffer (Invitrogen) with an X-cell II blot module (Invitrogen). Membranes were blocked 1 hour at room temperature in PBS supplemented with 0.05% Tween (PBST) and 3% BSA for one hour at room temperature (RT) with agitation; incubations were performed in diluent buffer (PBST supplemented with 0.5% BSA) for 30 min at RT with agitation; washes were carried out in PBST 3 times for 5 min at RT with agitation. Reduced samples were diluted 1:1 with 10 microliters of SDS loading buffer (Invitrogen) supplemented with 5% mercaptoethanol (Sigma-Aldrich) and boiled 5 min; native samples were diluted 1:1 in native running buffer (Invitrogen) and loaded without boiling. Signals were detected with SuperSignal West Pico Chemiluminescent Substrate (Pierce) according to standard procedure and exposed to Kodak X-OMAT AR films (Fisher/Kodak). In some experiments, signals were stripped with WesternRestore™ Western Blot Stripping Buffer (Pierce).

ScFv were detected with HRP-conjugated anti-V5 mAb (Serotec, Raleigh N.C.). Biobodies were detected with HPR-conjugated streptavidin (BD PharMingen, San Diego, Calif.). When used to probe 10 cm² membranes, 5 micrograms of biobodies were premixed with 1 microliter of SA-HRP for 20 min in 250 microliters of PBS on ice and then added to 10 ml of diluent buffer. HE4-Ig and Meso-Ig were detected with biobodies or with HRP-conjugated F(ab')2 Fragment Goat Anti-Human IgG (H+L) polyclonal antibody (HRP-anti-hIg) (Jackson Immunoresearch Laboratory, Inc., West Grove, Pa.). All secondary reagents were diluted ten thousand fold in diluent buffer.

ELISA Analysis: ELISA assays were performed in Nunc Amino™ or Streptavidin Immobilizer™ plates (Nunc, Rochester, N.Y.) with gentle agitation at RT. Amino plates were coated with fusion proteins diluted in bicarbonate buffer (carbonate-bicarbonate buffer capsules, Sigma-Aldrich) for one hour. PBST-prewashed streptavidin plates were coated with diploid supernatants or Ni-purified biobodies diluted in PBST for one hour. Other incubations and washes were carried in PBST for 30 min with rotation at RT. In accordance with the manufacturer's recommendations, no blocking steps were necessary with these plates since all incubations are carried in PBST. Samples were run in duplicates. Colorimetric signals were revealed with TMB One Solution (Promega), stopped with sulfuric acid (Acros, N.J.), and read at 450 nm on a Spectra Max 250 (Molecular Devices, Sunnyvale, Calif.). Ig-fusion proteins were detected with 5 micrograms/ml of HRP anti hIg, or with 5 micrograms/ml of anti-HE4 mAb (3D8 or 2H5) (Hellstrom, et al., Cancer Res. 63:3695-700 (2003)) followed by 1/1000 HRP rabbit anti-mouse IgG (HRP anti mIg, Serotec) or with 5 micrograms/ml of biobodies followed by 1/1000 anti-V5 or SAHRP, or with 5 micrograms/ml or less (as indicated) of biobodies premixed for 20 min with 1/1000 of anti-V5 or SA-HRP in PBS at 4° C.

Conversion of yeast-secreted scFv into in vivo biotinylated recombinant antibodies by yeast mating: pTOR-BIR (SEQ ID NO:9) was transformed into BJ5475 MATa ura3-52 trp1 his3 delta 200 pep4::HIS3 prb1 delta 1.6R can1 GAL (the kind gift of Elizabeth Jones). Transformants were selected on SD+CAA+0.002% uracil (Sigma-Aldrich) (SD-CAA+URA). Cells containing pTOR-BIR (SEQ ID NO:9) were spread at high density on SD-CAA+URA and grown at 30° C. overnight (ON). pTOR2-scFv transformants (MATalpha trp-) and the lawn of pTORBIR containing cells (MATa ura-) were replica plated to a YEPD plate (rich medium), allowed to mate for 8 to 16 hours, then replica plated to a SD+CAA plate lacking uracil and tryptophan to select diploids. Selected diploid patches were replicated two more times to SD+CAA to eliminate unmated haploids. Diploid pool and diploid clones secreted in vivo biotinylated recombinant antibodies, or biobodies, as further described below.

Production and Ni-purification of biobodies: Diploid cells were grown in 100 ml of SD-CAA medium to saturation and induced 3 days in 100 ml of YEPGR. The cultures were centrifuged 5 min at 3000 rpm to pellet the cells. Supernatants were desalted and concentrated with Vivaspin concentrators (VivaScience AG, Hanover, Germany). After adjusting to 0.3 M sodium chloride (Sigma-Aldrich), and to pH 7-8 with sodium phosphate ($Na_2HPO_4$), supernatants were incubated with HIS-Select-Nickel Affinity Gel (Sigma-Aldrich) according to manufacturer instructions. Biobodies were eluted by competition with imidazole (Fisher) into a volume of less than 1 ml and dialyzed against 1000 volume of PBS at 4° C. ON in a Tube-O-Dialyzer (Upstate Cell Signaling Solutions, Charlottesville, Va.). Protein concentrations were evaluated by Nanoorange Protein Quantization Kit (Invitrogen) and were routinely of 50 to 200 micrograms/ml, corresponding to a yield of 0.5 to 2 mg/L.

Results:

Flow cytometry analysis was carried out with yeast-display scFv during and after differential sorting. Yeast-display scFv were labeled after five enrichments with 100 nM of HE4-Ig, or after 5 enrichments followed by two rounds of depletion with 100 nM of Meso-Ig and one enrichment with 50 nM of HE4-Ig. To assess scFv expression, samples were incubated with anti-cmyc mAb. To assess antigen specificity, samples were incubated with biotinylated HE4-Ig or biotinylated Meso-Ig. All samples were labeled with SA-PE and 488 anti-mIg. Results obtained, as described below, were representative of two independent experiments.

As described above, a yeast-display scFv library was first enriched for scFv binding to 100 nM of HE4-Ig. After five enrichments, half of YD scFv bound to HE-4Ig, but a third of these also bound to the control protein Meso-Ig. This was expected since HE4-Ig and Meso-Ig share a 696 bp-immunoglobulin sequence. To eliminate the Ig-binding scFv from the anti-HE4-Ig sublibrary, two rounds of magnetic depletion with Meso-Ig and one last enrichment with HE4-Ig were conducted as described above. The resulting anti-HE4 yeast-display scFv subtractive library contained more than 95% scFv that bound only to HE4-Ig.

Figure 3B:
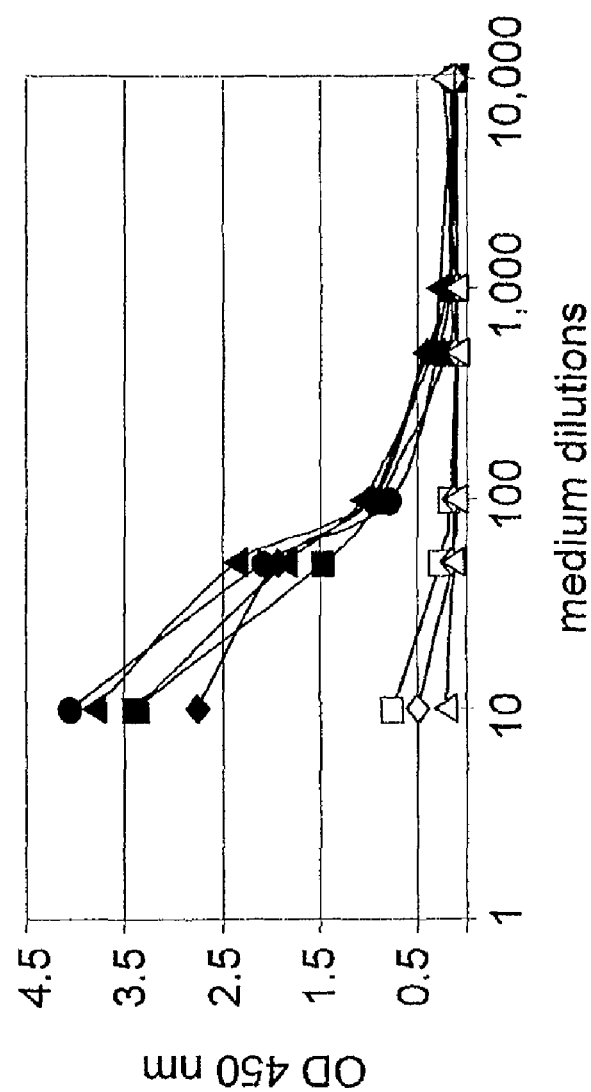
FIG. 3B graphically presents results from an ELISA assay demonstrating that mating of haploid yeast carrying scFv fused to BCCP (expressed from the pTOR2 vector; SEQ ID NO:1) and haploid yeast carrying BirA fused to golgi-targeted KEX2 domains (expressed from pTOR-BIR vector; SEQ ID NO:9), generates diploids that secrete in vivo biotinylated scFv, as described in Example 2.
Figure 3A:
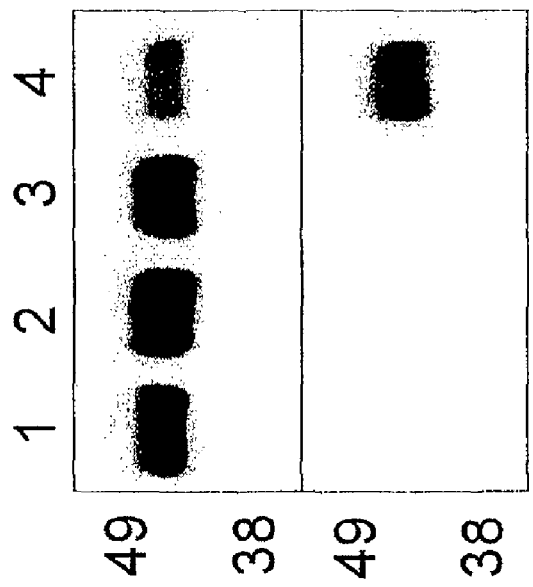
FIG. 3A shows the results of a Western blot analysis of diploid supernatants, demonstrating the presence of in vivo biotinylated scFv, as described in Example 2.

FIG. 3A shows a Western blot analysis of diploid supernatants, demonstrating the presence of in vivo biotinylated scFv. Supernatants from pTOR2-scFv haploid (lane 1), pTOR2-scFv/p414-GAL1 diploid (lane 2), pTOR2-scFv/p414gal1-BirA-cmyc diploid (lane 3) and pTOR-scFv/pTOR-BIR diploid (lane 4) were probed with HRP-conjugated and anti-V5 mAb (upper panel), stripped and reprobed with SA-HRP (lower panel). As shown in FIG. 3A, all supernatants isolated from diploid cells contained a V5-tagged protein of ~42 kDA, consistent with the scFv size (see FIG. 3A, upper panel). However, streptavidin-HRP could only detect the 42 kDa protein in pTOR2-scFv/pTOR-BIR diploid supernatant (see FIG. 3A, lower panel, lane 4), which indicates that golgi-targeting KEX2 domains are necessary and sufficient for proper localization and function of the *E. coli* biotin ligase in the yeast secretory pathway.

FIG. 3B shows the results from supernatants from several diploids immobilized on streptavidin-coated wells and probed with HRP anti-V5 mAB. Supernatants from pTOR2-scFv haploid (white squares), pTOR2-scFv/p414-GAL1 diploid (white triangles) and 5 independent pTOR2-scFv/pTOR-BIR diploids (black symbols) were incubated in streptavidin-coated wells and detected with HRP anti-V5 mAb. Yeast medium was used as back-ground control (white diamonds). As shown in FIG. 3B, only the pTOR2-scFv/pTOR-BIR diploid supernatants bound to streptavidin plates (see FIG. 3B, black symbols).

These results confirm that the V5-tagged protein was identical to the biotinlabeled protein and is indeed a scFv, and demonstrate that mating of haploid yeast carrying scFv fused to BCCP (pTOR2 vector) and yeast carrying BirA fused to golgi-targeting KEX2 domains (pTOR-BIR) is necessary and sufficient to generate diploids that secrete in vivo biotinylated scFv, otherwise referred to as biobodies.

EXAMPLE 3

This Example demonstrates the functional validation of the anti-HE4 biobodies generated as described in EXAMPLE 2.

Methods:

ELISA analysis: An anti-HE4 biobody corresponding to a pool of in vivo biotinylated scFv were compared to anti-HE4 mAb 3D8 for its ability to detect plastic immobilized HE4-Ig or Meso-Ig by ELISA assay (as described in more detail in Example 2).

Results of ELISA Analysis: FIGS. 4A-C shows the results of the anti-HE4 biobody validation by ELISA assays. All results shown in FIGS. 4A-C are representative of two independent experiments; standard deviations were less than 10%. FIG. 4A shows the results of serial dilutions of HE4-Ig that were immobilized on amino wells and incubated with anti-HE4 pBb followed by HRP anti-V5 mAb (white triangles) or SA-HRP (white squares). Alternatively, as further shown in FIG. 4A, immobilized HE4-Ig was incubated with anti-HE4 pBb premixed with HRP anti-V5 mAb (black triangles) or SA-HRP (black squares). As positive control, immobilized HE4-Ig was detected with anti-HE4 mAb (3D8) followed by HRP anti-mIg (stars on dotted line). As negative control, serial dilutions of Meso-Ig were immobilized and incubated with anti-HE4 pBb premixed with SA-HRP (gray squares). As shown in FIG. 4A, monomeric anti-HE4 pBb incubated in HE4-Ig-coated wells and detected with HRP-conjugated anti-V5 mAb (HRP-V5 mAb, white triangles) or streptavidin (SA-HRP, white squares) generated poor colorimetric signals. However, colorimetric signals were significantly enhanced when anti-HE4 pBb was premixed with HRP anti-V5 mAb (black triangles) and, remarkably, when premixed with SA-HRP (black squares) the detection range of anti-HE4 pBb for HE4-Ig was similar to 3D8 mAb (stars on dotted line). Anti-HE4 pBb premixed with SA-HRP did not detect plastic immobilized Meso-Ig (gray squares), demonstrating the specificity of anti-HE4 biobody.

FIG. 4B shows the results of serial dilutions of five anti-HE4 mBb that were preincubated with SA-HRP together (black symbols) or separately (white symbols) before detection of 250 ng of plastic-immobilized HE4-Ig (diamonds) or Meso-Ig (circles). In FIG. 4B, the detection ranges of five anti-HE4 mBb (mBb#3; 10; 12; 13 and 15) for 250 ng of immobilized HE4-Ig (diamonds) or Meso-Ig (circles) were compared after being premixed with SA-HRP individually (white symbols) or together (black symbols). The five biobodies shown in FIG. 4B were incubated separately or together with streptavidin and then mixed together to perform the experiment. As shown in FIG. 4B, sensitivity increased when mBb were premixed together with SA-HRP (black diamonds) to compare with mBb premixed separately (white diamonds) when biobodies were used in limiting quantities (less than 2.5 µg/ml). This suggests that the high affinity of anti-HE4 pBb/streptavidin complexes could be due in part to a cooperative effect between the diverse biotinylated scFv species included in pBb.

FIG. 4C shows the results of five mBb that were coated separately or together (as indicated) as capture antibody in a sandwich ELISA assay on a streptavidin-coated plate, and then incubated with serial dilutions of HE4-Ig. Captured HE4-Ig was detected with anti-HE4 mAb (2H5) followed by HRP anti mIg. As shown in FIG. 4C, anti-HE4 mBb used separately or together can complement anti-HE4 mAb to detect nanograms of HE4-Ig in a sandwich ELISA assay setting.

Flow Cytometry Analysis: Biobodies premixed with phytoerythrin-conjugated streptavidin (SA-PE) were used for cell detection in flow cytometry analysis (as described in Example 2).

Results of Flow Cytometry Analysis: The HEK-293F cell line was stably transfected with HE4-HA tagged or, as a negative control, MPF-HA tagged cell-surface protein. As expected, both transfected cell lines expressed equal amounts of HA-tags as detected with anti-HA mAb, but anti-HE4 mAb 3D8 and anti-HE4 pBb specifically bound to HE4-transfected cells (data not shown), while HEK 293F cells were only labeled with anti-HA mAb. As negative controls, cells were incubated with 488 anti-mIg only, or SA-PE only. Results described are representative of two independent experiments.

Figure 5A:
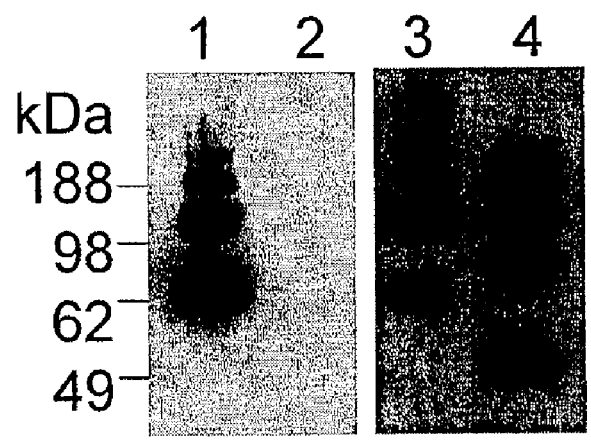
FIG. 5A shows a Western blot analysis of HE4Ig (lanes 1, 3) and Meso-Ig proteins (lanes 2, 4) loaded under native conditions, as described in Example 2.
Figure 5B:
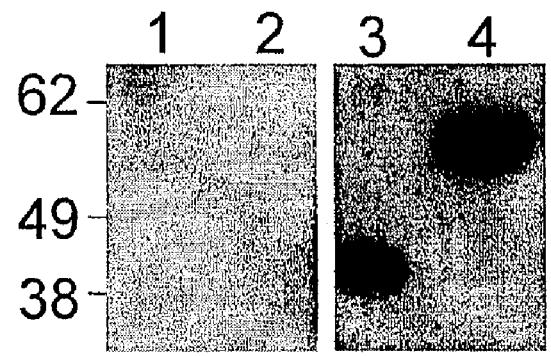
FIG. 5B shows a Western blot analysis of HE4Ig (lanes 1, 3) and Meso-Ig proteins (lanes 2, 4) loaded under reduced conditions, as described in Example 2.

Western Blot Analysis: FIGS. 5A and 5B show the results of biobodies used as probes for Western blots of HE4Ig (lanes 1, 3) and Meso-Ig proteins (lanes 2, 4) loaded in native (FIG. 5A), or reduced conditions (FIG. 5B). The Western blots were first probed with anti-HE4 pBb premixed with SA-HRP (lanes 1-2), stripped and reprobed with HRP anti-hIg (lanes 3-4). Results shown are representative of three independent experiments.

In native conditions several bands were detected by pBb (FIG. 5A, lane 1), or HRP anti-hIg (FIG. 5A, lanes 3-4), corresponding to multi-protein complexes. Anti-HE4 pBb premixed with SA-HRP detected HE4-Ig loaded in native condition only (compare lanes 1 of FIGS. 5A and 5B). This result confirms the specificity of anti-HE4 pBb and also suggests that anti-HE4 pBb epitopes may be dependent on the tertiary structure of the protein altered by reducing conditions.

Surface plasmon resonance (SPR) sensor Analysis: anti-HE4 pBb was immobilized on a SPR sensor surface after purification by nickel columns or directly from medium in which yeast had been induced to secrete Bb. The SPR system used was a custom-built four-channel instrument based on the Kretschmann configuration of the attenuated total reflection method (Homola, et al., *Int. J. Food Microbiol.* 75:61-9 (2002)). The glass side of the gold-coated substrate is index matched to the prism coupler while the functionalized surface is mechanically pressed against an acrylic flow cell with a Mylar gasket. A polychromatic light beam directed through the prism and the glass substrate excites surface plasma waves at the metal-dielectric interface. The reflected light was analyzed with a spectrograph. The reflectivity spectrum is dependent upon the refractive index of analytes in proximity to the surface, allowing the detection of binding events to the surface. SPR sensor chips, BK7 glass chips 32 mM×15 mM×1.5 mM (Schott), were coated with 2 nm of Cr and 55 nm of Au by electron beam evaporation. These chips were rinsed with copious amounts of absolute ethanol and water. Chips were dried by blowing with dry $N_2$, then cleaned by UV-ozone for 20 min, and finally exhaustively rinsed with water and absolute ethanol before surface functionalization. A mixture of oligo ethylene glycol (OEG) and biotinylated alkanethiols (BAT) was dissolved in absolute ethanol. The BAT, a $C_{15}$ alkanethiol chain linked to a biotin headgroup by three ethylene glycol groups, was used as the specific binding element of the SAM targeting streptavidin, while the OEG, a $C_{10}$ alkanethiol chain linked to a hydroxyl headgroup by four ethylene glycol groups, created a nonfouling background (Ladd, et al., *Langmuir* 20:8090-5 (2004)). The mixture had a total thiol concentration of 100 nM and consisted of a 1:9 ratio of BAT:OEG. The cleaned chips were immersed in the OEG/BAT solution overnight. Sensor chips were then removed from the OEG/BAT solution, rinsed with copious amounts of absolute ethanol, dried with dry $N_2$, and then mounted in the SPR instrument.

All experiments were carried out at 25° C. and began with flowing PBS (pH 7.4) at 50 microliters/min for 10 min. Following the establishment of a baseline, 10 micrograms/ml streptavidin was flowed over all four channels for 10 min at 50 microliters/min to prepare the surface for the binding of biobodies. After 10 min of PBS wash, either yeast supernatant or a 10 micrograms/ml purified biobody solution was directly flowed over the surface at 50 microliters/min for 5 min to immobilize the biobodies. Following 10 min of PBS wash, HE4-Ig was flowed for 10 min at 10 microliters/min, with one channel acting as a reference. PBS was flowed once again for up to 20 min to allow for the dissociation of HE4-Ig. HE4-Ig concentrations were varied from 10 ng/ml (0.2 nM) to 10 micrograms/ml (200 nM).

Results:

Surface Plasmon resonance (SPR) response curves were generated for the detection of HE4-Ig in a range of concentrations from 0.2 nM to 200 nM. Biobodies were immobilized either directly from yeast supernatant or from nickel column purified anti-HE4 pBb. Results representative of two independent experiments. SPR response curves for the binding of the anti-HE4 pBb to HE4-Ig were fit to a pseudo-first-order equation (i.e., 1:1 Langmuir isotherm) (Myszka and Morton, *Trends Biochem. Sci.* 23:149-50 (1998)). The dissociation equilibrium constants for anti-HE4 pBb directly from unpurified and purified biobodies were $K_d$=4.82×10$^{-9}$ M and $K_d$=5.13×10$^{-9}$ M, with the association rate constants ($k_a$) of $3.86×10^4 M^{-1s-1}$ and $3.25×10^4 M^{-1s-1}$, and the dissociation rate constants ($k_d$) of $1.86×10^{-4 s-1}$ and $1.67×10^{-4 s-1}$, respectively. These results are very similar, indicating that it is not necessary to purify the biobodies prior to use with SPR sensors.

Purification of Biobodies with Streptavidin-coated Fluorescent Beads

Streptavidin-coated fluorescent beads were coupled with in vivo biotinylated proteins (CA125, mesothelin "MSLN", or HE4) directed from yeast supernatant, or after nickel purification (purified). Protein binding was assessed in mean fluorescence (MFI) using a bead-based assay with specific antibodies detected with PE-labeled anti-mouse Ig mAb diluted 1:100. The results are shown below in TABLE 1:

TABLE 1

Antigen-Specific Affinity of Purified and Unpurified Biobodies

| Beads coated w/ | Detection with anti-HE4 mAb (2H5 0.1 ug/mL) (measured in MFI) | Detection with anti-MSLN mAb (4H3 1 ug/mL) (measured in MFI) | Detection with anti-CA125 mAb (X306 1 ug/mL) (measured in MFI) | No antigen-specific mAb (background control) (measured in MFI) |
|---|---|---|---|---|
| nothing (negative control) | 3 | 13.5 | 3 | 7 |
| bBSA (control specificity) | 4 | 62 | 3 | 4 |
| bCA125 supernatant | 2 | 6.5 | 3357.5 | 3 |

TABLE 1-continued

Antigen-Specific Affinity of Purified and Unpurified Biobodies

| Beads coated w/ | Detection with anti-HE4 mAb (2H5 0.1 ug/mL) (measured in MFI) | Detection with anti-MSLN mAb (4H3 1 ug/mL) (measured in MFI) | Detection with anti-CA125 mAb (X306 1 ug/mL) (measured in MFI) | No antigen-specific mAb (background control) (measured in MFI) |
|---|---|---|---|---|
| bCA125 purified | 3 | 19.5 | 2377 | 4 |
| bMSLN supernatant | 50 | 13114 | 39.5 | 3 |
| bMSLN purified | 98 | 14478.5 | 27 | 2 |
| bHE4 supernatant | 4030 | 9.5 | 4 | 3 |
| bHE4 purified | 4535.5 | 11 | 4 | 3 |

Results: As shown above in TABLE 1, secreted biobodies do not require purification from the yeast culture media, because purified and non-purified (supernatant) biobodies have the same antigen-specific affinity.

Discussion: The experiments described above demonstrate that mating of yeast carrying a cDNA encoding a recombinant antibody fused to a biotin acceptor site with yeast carrying a cDNA encoding an *E. coli* biotin ligase fused to yeast golgi-localization sequences from KEX2, results in diploid yeast able to secrete in vivo biotinylated recombinant antibodies of high affinity that we named biobodies.

Because in vivo biotinylation is highly specific for the BCCP lysine, it can be achieved without modification of critical lysine residues belonging to antibody recognition sequences and thus without functional loss of the recognition domains. The human IgA1 hinge between the recognition and the biotin accepting site sequences may also contribute to reduce scFv conformational changes due to biotinylation or to binding mediated by biotin/streptavidin interactions. Indeed, the overall affinity of the anti-HE4 scFv subtractive library displayed by yeast did not decrease after conversion into soluble in vivo biotinylated recombinant antibodies; the affinity of the anti-HE4 polyclonal biobody was found in the nanomolar range.

By ELISA assays, anti-HE4 biobody affinity appeared to be increased after preincubation with anti-V5, consistent with a previous report by Wang and colleagues (Wang, et al., *J. Immunol. Methods* 294:23-35 (2004)), but was dramatically improved after preincubation with streptavidin, consistent with previous reports of tetramerization of biotinylated recombinant antibodies in presence of streptavidin (Muhlrad, et al., *Yeast* 8:79-82 (1992); Saviranta, et al., *Bioconjug. Chem.* 9:725-35 (1998); Cloutier, et al., *Mol. Immunol.* 37:1067-77 (2000)). In addition, the affinity of five anti-HE4 monoclonal biobodies (mBb) increased when they were preincubated with streptavidin together instead of separately, which suggests a cooperative effect of the biobodies. Finally, five anti-HE4 mBb were successfully used as capture antibodies to complement an anti-HE4 mAb in a sandwich ELISA assay, which demonstrates that this method can be used to rapidly develop assays necessary for validation of serum biomarkers.

By Western blotting, anti-HE4 polyclonal biobodies (pBb) was able to specifically detect native but not reduced HE4 protein. This implies that anti-HE4 pBb may preferentially detect conformational epitopes. It may be due to the possible limited representation of recognition sequences of this particular reagent suggested by the sequencing of 15 anti-HE4 mBb showing scFv belonging to the same vH and vL subgroups (data not shown). Alternatively, it might be an intrinsic characteristic of the yeast-display scFv library to generate scFv with preferential affinity for conformational epitopes (Weaver-Feldhaus, et al., *Protein Eng. Des. Sel.* 18:527-36 (2005)). In either case, the ability of an affinity reagent to distinguish subtle conformational changes is a desirable characteristic for the accurate detection of biomarkers that often result from structural modifications of normal proteins through cleavage, aberrant transcriptions or post-translational modifications (Mahlknecht and Hoelzer, *Mol. Med.* 6:623-44 (2000); Brinkman, *Clin. Biochem.* 37:584-94 (2004); Venables, *Cancer Res.* 64:7647-54 (2004); Kalnina, et al., *Genes Chromosomes Cancer* 42:342-57 (2005); and Santos-Rosa and Caldas, *Eur. J. Cancer* 41:2381-402 (2005)).

By SPR, anti-HE4 pBb demonstrated a $K_d$ in the nanomolar range when immobilized on a streptavidin-coated surface either from purified biobodies or directly from yeast supernatant. The same order of magnitude of dissociation equilibrium constants of purified and non-purified biobodies indicates that purification is not required for high affinity. Thus yeast supernatant can be used to directly immobilize yeast secreted in vivo biotinylated recombinant antibodies on any streptavidin-coated surfaces, including a sensor surface. In vivo biotinylated proteins can also be produced with the same yeast-expression system. This greatly simplifies and reduces the cost of development of arrayed sensor platforms for large-scale biomarker discovery and detection.

It is conceivable that this method may also facilitate the conversion of mouse monoclonal antibodies into functional recombinant antibodies. Finally, this method may also be used to generate reagents for emerging technologies such as antibody-based proximity ligation (Fredriksson, et al., *Nat. Biotechnol.* 20:473-7 (2002)), antibody-based competition assays using "tadpoles" (as described in Burbulis, et al., *Nat. Methods* 2:31-7 (2005)), bead-based assays (Vignali, *J. Immunol. Methods* 243:243-55 (2000); Gorelik, et al., *Cancer Epidemiol. Biomarkers Prev.* 14:981-7 (2005); Scholler, N., et al., *Clin. Cancer Res.* 12:2117-2124 (2006)), and protein or antibody arrays (Chen, et al., PloS Med 2, e265 (2005); Gao, et al., *BMC Cancer* 5:110 (2005); Utz, *Immunol. Rev.* 204:264-82 (2005); Boozer, et al., *Anal. Chem.* 78:1515-9 (2006)).

In conclusion, the yeast expression system described here allows efficient generation of directly biotinylated high-affinity reagents that are needed for a large range of applications, including evaluation of the products of large scale proteomics discovery projects.

EXAMPLE 4

This Example demonstrates the use of the vector systems of the invention to generate biobodies that specifically bind to both membrane-bound and soluble forms of mesothelin and block CA125/mesothelin-dependent cell adhesion.

Background/Rationale: The interaction between mesothelin and CA125 proteins is thought to play an important functional role by mediating cell adhesion between CA125-expresser tumor cells and the peritoneal lining that expresses a membrane-bound form of mesothelin (Rump, A., et al., *J. Biol. Chem.* 279(10):9190-8 (2004); Scholler, N., et al., *Cancer Letters*, in press)). Mesothelin is a 40 kDa protein constitutively expressed at the surface of mesothelial cells (peritoneal cardiac and pleural linings) but also by mesotheliomas and ovarian carcinoma cells (Chang, K., et al., *Proc. Natl Acad. Sci. USA* 93(1):136-40 (1996)). Mesothelin is also found soluble in mesothelioma and ovarian carcinoma patient sera and urines (Scholler, N., et al., *Proc. Natl Acad. Sci. USA* 96(20):11531-6 (1999); Robinson, B. W., *Lancet* 362(9396): 1612-6 (2003); Hassan, R., *Clin. Cancer Res.* 12(2):447-53 (2006)); soluble mesothelin can arise through at least 2 mechanisms, the predominant one arises from the cleavage of a hydrophobic glycosylphosphatidylinositol (GPI) anchor (Hassan, R., *Clin. Cancer Res.* 12(2):447-53 (2006)), while the other one known is due to a reading frame shift that suppresses the GPI anchor motif (Scholler, N., et al., *Proc. Natl Acad. Sci. USA* 96(20):11531-6 (1999)). Both the GPI domain and the modified reading frame are located in C-terminal portion. Mesothelin results from the cleavage of a 69 kDa preprotein encoded by the human MSLN gene (Genbank reference number NC_000016, hereby incorporated by reference), that spans over 16 exons and occupies about 8 kb of human chromosome 16. The alternative splicing of MSLN gene results in at least two mesothelin transcript variants, variant 1 encoded by MSLN1 (Genbank reference number NM_005823, hereby incorporated by reference), and variant 2 encoded by MLSN2 (Genbank reference number NM_013404, hereby incorporated by reference).

CA125 is a mucin-like protein of high molecular mass, estimated from 200 to 20,000 kDA, although smaller subunits have been reported (O'Brien, T. J, et al., *Int. J. Biol. Markers* 13(4):188-95 (1998); Yin, B. W., et al., *J. Biol Chem* 276(29): 27371-5 (2001)). CA125 cell surface expression is upregulated when cells undergo metaplastic differentiation into a Müllerian-type epithelium (Feeley, K. M., *Histopathology* 38(2):87-95 (2001)). CA125 is the most extensively studied biomarker for possible use in the early detection of ovarian carcinoma (Kenemans, P., et al., *Eur. J. Obstet. Gynecol. Reprod. Biol.* 49(1-2):115-24 (1993); Tamakoshi, K., et al., *Gynecol. Obstet. Invest.* 39(2):125-9 (1995); Dorum, A., *Eur. J. Cancer* 32A(10):1645-51 (1996); Eagle, K, et al., *Oncologist* 2(5):324-329 (1997); Fures, R., et al., *Coll. Antropol.* 23(1):189-94 (1999); Jacobs, I. J., et al., *Mol. Cell Proteomics* 3(4):355-66 (2004)). However, although CA125 is conserved in mammals (Nouwen, E. J., et al., *Differentiation* 45(3): 192-8 (1990); McDonnel, A. C., et al., *Reproduction* 126(5): 615-20 (2003); Duraisamy, S., et al., *Gene* 373:28-34 (2006)), there is no available antibody against mouse CA125 which impairs ovarian cancer studies in vivo.

Therefore, blocking CA125/mesothelin-dependant cell attachment may prevent or delay peritoneal metastases that, in contrast with other cancers, are often present when the disease is first diagnosed. Combining early detection through a panel of serum biomarkers and preventive therapies could positively impact ovarian cancer toll.

An in vitro cell adhesion assay has been developed that involves combining cells expressing CA125 and mesothelin-transfected cells. Through the use of this assay it was demonstrated that CA125/mesothelin-dependant cell adhesion could be blocked with both mesothelin recombinant protein fused to Ig domain (meso-Ig) and cross-linked with anti-Ig antibodies, and with anti-CA125 mouse monoclonal antibodies (mAb) of group B (Scholler, N., et al., "Development of a CA125-mesothelin cell adhesion assay as a screening tool for biologics discovery," *Cancer Letters*, in press (2006)). These results suggest that new therapies based upon affinity agents able to compete and block CA125/mesothelin interaction could prevent or delay the development of peritoneal metastasis. However, mAbs are highly immunogenic in vivo (Khazaeli, M. B., et al., *J. Immunother* 15(1):42-52 (1994)), and need to be humanized for therapeutic use (Hwang, W. Y., et al., *Methods* 36(1):3-10 (2005); Clark, M., et al., *Immunol. Today* 21(8):397-402 (2000)), which is a costly and difficult process. Recombinant antibodies are emerging as being an attractive alternative to classical antibodies (Wu, A. M., et al., *Proc. Natl Acad. Sci. USA* 96(15):8495-500 (2000); Berndorff, D., et al., *J. Nucl. Med.* 47(10):1707-16 (2006)). Accordingly, the methods of the present invention may be used to generate recombinant, secreted, in vivo biotinylated antibodies that block CA125/mesothelin-dependant cell adhesion, as described below.

Methods:

Yeast-Expression of Soluble, In vivo Biotinylated Recombinant Proteins

Mesothelin cDNA encoding MSLN1 (Genbank reference number NM_005823, hereby incorporated by reference), was amplified from cDNA clone MGC: 10273 IMAGE: 3957372 (ATCC) using the forward 5'-gattataaagatgac-gataaaggtggtggtggttctgctagcgaagtggagaagacagcctg-3' (SEQ ID NO:25) and reverse 5'-gggttagggataggcttaccctgttgt-tctagaattccgagtgctaggacggtgagaac-3' (SEQ ID NO:26) primers to add the cloning sequences necessary for gap repair (Scholler, N, et al., *J. Immunol Methods* 317:132-143 (2006)). MUC16 repeat sequence, (Genbank reference number NP_078966, hereby incorporated by reference) was reverse-transcribed and amplified from OvCar3 RNA using the following primers: forward 5'-Gattataaagatgacgataaag-gtggtggtggttctgctagcggtcacacagagcctggtc-3' (SEQ ID NO:27) and reverse 5'-gggttagggataggcttaccctgttgt-tctagaattccaggcagggaggatggagtac-3'. (SEQ ID NO:28) primers.

PCR products were purified on a Qiaquick gel extraction column according to the manufacturer instructions (Qiagen, Valencia, Calif.) and cotransformed with linearized pTOR2 vector (SEQ ID NO:1) into the yeast strain YVH10 (described in Feldhaus, et al., *Nat. Biotechnol.* 21(2):163-70 (2003)), as described in Example 2 herein. Yeast colonies prototrophic for uracil secreted mesothelin (meso) or MUC16 repeat domain (muc) recombinant proteins were mated with yeast carrying pTOR-BIR (SEQ ID NO:9). Resulting uracil/tryptophan-prototrophic diploid colonies secreted HIS-, V5- and flag-tagged, in vivo biotinylated mesothelin (b-meso) or MUC16 repeat domain (b-muc16) recombinant proteins. The recombinant protein b-meso was used to isolate anti-mesothelin biobodies and b-muc16 was used as a control.

Generation of Anti-Mesothelin Yeast Display-scFv Pool and Conversion into Yeast-Secreted scFv A yeast display scFv library (Feldhaus, M. J., et al., *Nat. Biotechnol* 21:163-170 (2003)) was first enriched for scFv that bound to b-meso by two rounds of magnet enrichment and three rounds of flow sorting (Scholler, N., et al., *J. Immunol. Methods* 317:132-143 (2006); Feldhaus, M. J., et al., *Nat. Biotechnol.* 21(2):163-70 (2003)). The anti-mesothelin yeast-display scFv were then transformed into yeast-secreted scFv as described in Scholler, N., et al., *J. Immunol. Methods* 317:132-143 (2006). Briefly, described, scFv recognition sequences from sorted yeast were PCR-amplified with the following primers.

pTOR2 forward (5'-gattataaagatgacgataaaggtggtg-gtggttctgcta-3') (SEQ ID NO:23) and pNL9 reverse (3'-gggt-tagggataggcttaccctgttgttctagaattccg-3') (SEQ ID NO:24) for cloning by gap repair. PCR products were cotransformed with 100 ng of linearized pTOR2 vector into YVH10 cells. Resulting uracil-prototrophic yeast colonies were inoculated in growth medium in deep well 96-well plates (Fisher Scientific, Pittsburgh Pa.), grown until saturation and then were induced to secrete scFv in presence of galactose for 72 hours.

High throughput Purification of scFv

Induced yeast cultures were pelleted by centrifugation. Eight hundred µl of yeast supernatants were transferred into clean deep well 96-well plates and salt and pH were adjusted with 80 ul of 10× equilibration buffer (3M Sodium chlorate (Sigma-Aldrich) and 0.5 M Tris pH 9 (Sigma)). HIS-Select-Nickel Affinity Gel (Sigma) (10 ul per well) was washed once with water and once with wash buffer (50 mM sodium phosphate pH 8 (Sigma), 0.3 M sodium chlorate and 10 mM imidazole (Fisher)), resuspended in 5 ml/plate of wash buffer per plate and 50 ul were distributed into each well. Plates were sealed with plate covers (Varian Inc., Palo Alto, Calif.) and rotated on a Labquake® rotator (Bamstead Thermolyne Dubuque, Iowa) for 45 minutes at 4° C. Supernatants incubated with HIS-Select-Nickel Affinity Gel were then transferred to prewet Multiscreen®-HV filter plates (Millipore Corporation, Billerica, Mass.) and drained with a vacuum manifold (Millipore) so that only nickel-bound scFv were retained by the filters. Nickel-bound scFv were washed twice with 100 ul of wash buffer per well on a plate shaker at 300 rpm for 10 min at room temperature (RT). ScFv were eluted from the HIS-Select-Nickel Affinity Gel by competition with imidazole. Fifty ul of elution buffer (50 mM sodium phosphate pH 8, 0.3 M sodium chlorate and 250 mM imidazole) were distributed in each well; a plate adaptor and a polypropylene 96-well round bottom plate (Fisher) were placed under the filter plate and wrapped together with the filter plate in foil. Plates were shaken at 300 rpm for 15 min at RT and the eluates were vacuumed into polypropylene plates. The elution process was repeated once and the eluates were stored at 4° C. up to one week before being tested by immunoassays.

Immunoassays

ELISA immunoassays were performed in Nunc Amino™ or Streptavidin Immobilizer™ plates (Nunc, Rochester N.Y.) with gentle agitation at room temperature. All washes and incubations were done in phosphate buffer saline (PBS) (Invitrogen) supplemented with 0.05% Tween (Fisher) (PBST) except for amino plate coatings that were performed in bicarbonate buffer (carbonate-bicarbonate buffer capsules, Sigma-Aldrich). Colorimetric signals were generated with 50 µl TMB One Solution (Promega, Madison, Wis.), stopped with 1N $H_2SO_4$ (Acros Organics USA, Morris Planes N.J.) and read at 450 nm on a Spectra Max 250 (Molecular Devices, Sunnyvale, Calif.).

When used as capture reagents, 25 ul of high-throughput Ni-purified scFv or 5 ug/ml of Biobodies were coated in a final volume of 50 ul of, respectively, coating buffer on a Nunc Amino™ plate or of PBST on a Streptavidin Immobilizer™ plate, for 1 hour at RT. When used as detection reagents, Biobodies were preincubated at 0.5 µg/ml with poly-HRP80 streptavidin (SA-polyHRP80) (Research Diagnostics, Inc, Concord, Mass.) diluted 1:1000 in PBS for 30 minutes on ice. To detect the presence of recombinant proteins in yeast supernatants, double determinant "sandwich" ELISA assays were performed on Nunc Amino™ plates, using as anti-flag mAB diluted at 2 ug/ml in bicarbonate buffer as the capture antibody and HRP-anti-V5 mAb diluted at 1/1000 in PBST as the detection antibody.

Cell immunoassays were performed on tissue culture-treated 96 well plates (BD Falcon San Jose, Calif.). Plates were coated with 50 µl of 0.01% poly-L-lysine (Sigma) and incubated at 37° C. for 1 hour. Excess liquid was then removed and the plates were air dried. After one wash with RPMI-1640 (Invitrogen), 200 µl of $2 \times 10^5$ OVCAR-3 cells/ml were plated to obtain about 90% confluence and incubated at 37° C. overnight. The day of the experiment, adherent cells were gently washed one time with pre-warmed media and 50 µl of fresh media was added per well without disturbing the cell monolayer. At the same time 10 µg/ml of Biobodies were preincubated with 1/1000 SA-polyHRP80 for 30 minutes in PBS before being added to each well (50 µl/well, final concentration of 5 ug/ml of Biobodies). After an incubation of 30 minutes with gentle agitation at room temperature (RT), wells were washed three times with PBS supplemented with 0.5% of bovine serum albumin (BSA) (Sigma-Aldrich). Colorimetric signals were detected as previously described supra.

Results:

Purified and in vivo biotinylated mesothelin (b-meso) and MUC16 (b-MUC16) recombinant proteins were produced with the yeast expression system described in Examples 1 and 2 in order to isolate anti-mesothelin yeast-display scFv. B-meso was used to select yeast-display scFv that bind to mesothelin while b-MUC16 was used to eliminate the non-specific and/or cross-reactive scFv.

Figure 6A:
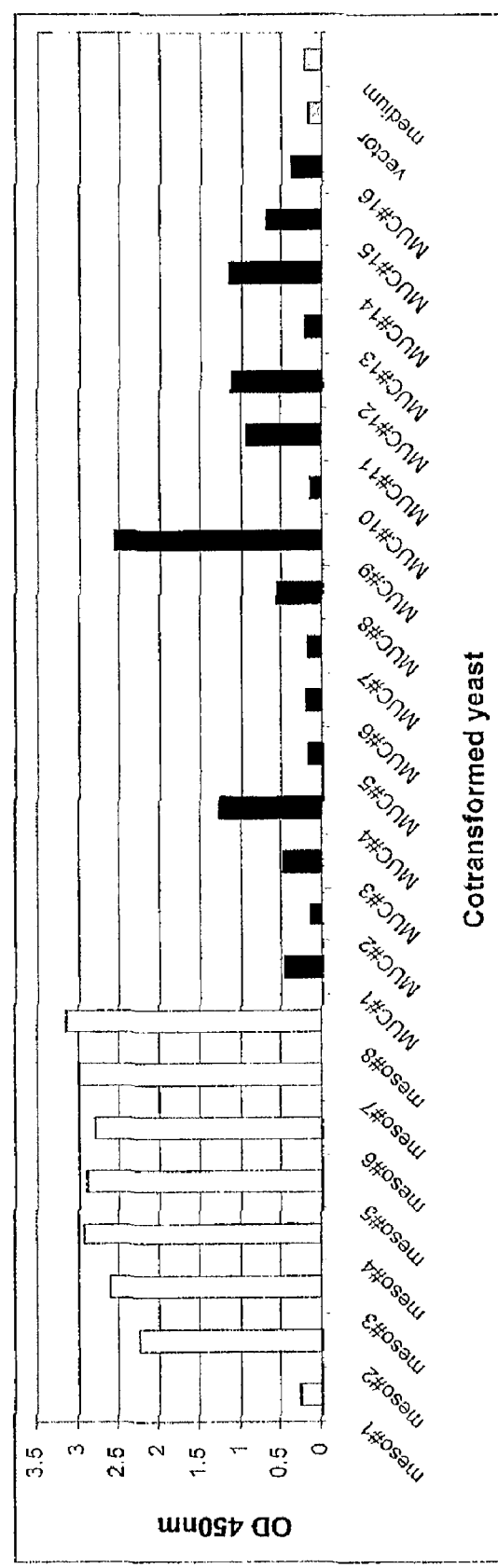
FIG. 6A graphically illustrates the results of an ELISA assay on yeast supernatants isolated from yeast co-transformed with mesothelin cDNA or MUC16 demonstrating that 7 of 8 yeast co-transformed with mesothelin cDNA and 9 of 16 yeast co-transformed with MUC16 repeat sequence secreted tagged proteins, as described in Example 4.
Figure 6B:
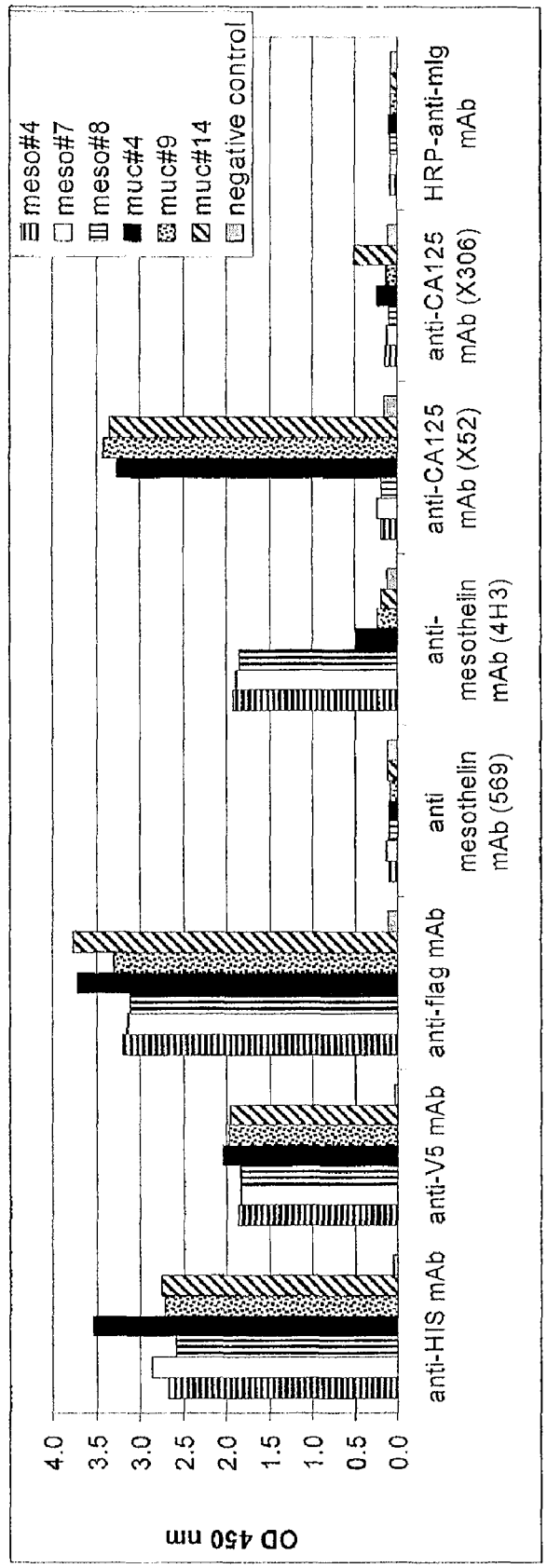
FIG. 6B graphically illustrates the results of an ELISA assay demonstrating the binding specificity of secreted scFv for mesothelin protein, as described in Example 4.
Figure 6C:
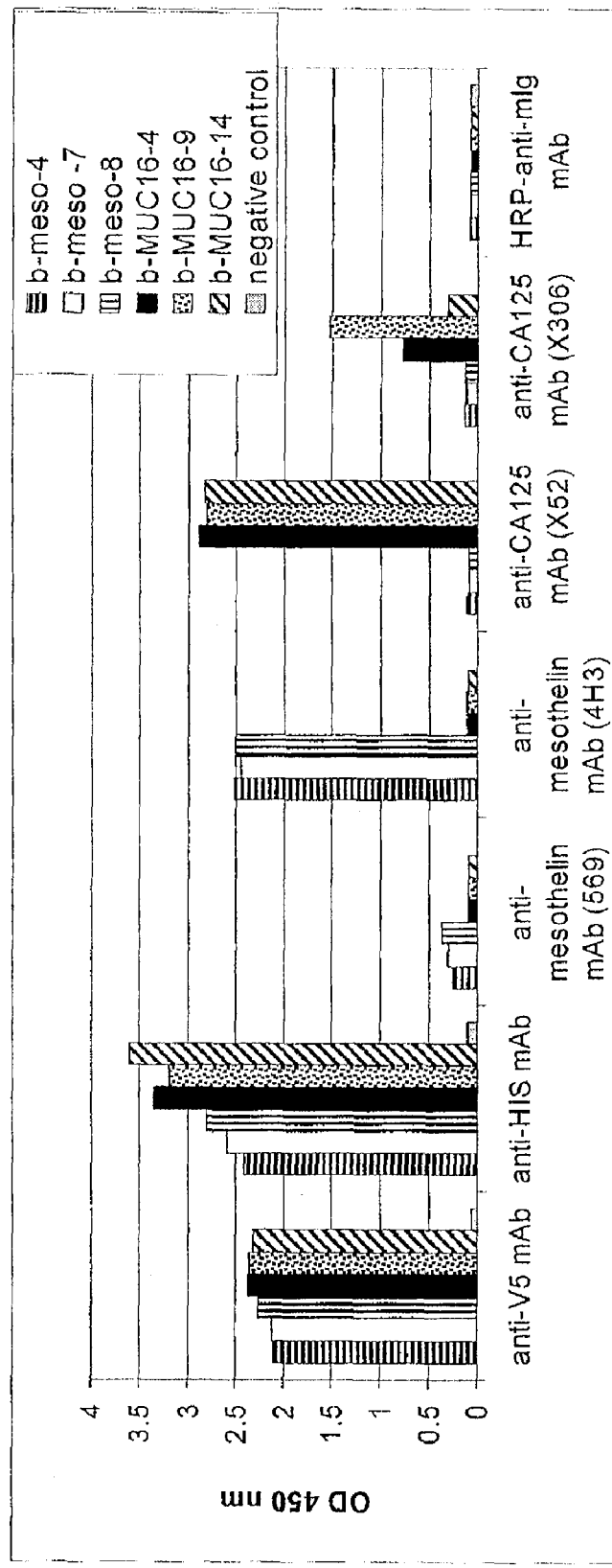
FIG. 6C graphically illustrates that scFv secreted by diploid yeast were in vivo biotinylated as demonstrated by binding to streptavidin-coated plastic, as described in Example 4.

The presence of recombinant proteins in yeast supernatants was demonstrated by sandwich ELISA assays. ScFv secreted in yeast supernatants were detected by sandwich ELISA assay using anti-flag mAb as capture and HRP anti-V5 mAbs. FIGS. 6A-C shows that mesothelin and MUC16 repeat domain were secreted as HIS, flag and V5-tagged recombinant proteins by uracil-prototrophic yeast and in vivo biotinylated by uracil/tryptophan-prototrophic diploid cells. FIG. 6A shows the results of 25 ul of supernatant from yeast cotransformed with mesothelin cDNA (white bars) or MUC16 repeat sequence (black bars) incubated in duplicate in 96-well Nunc Amino™ plates coated with anti-flag mAb and detected with HRP-anti-V5 mAb. Media only and supernatant from yeast transformed with pTOR2 only were used as negative controls (gray bars). As shown in FIG. 6A, 7 out of 8 yeast cotransformed with mesothelin cDNA and 9 out of 16 yeast cotransformed with MUC16 repeat sequence secreted tagged proteins.

Recombinant proteins secreted by yeast cotransformed with mesothelin cDNA (meso #4, #7 and #8) or MUC16 repeat sequence (muc #3, #9 and #14) were Ni-purified from yeast supernatants and the recombinant proteins were immobilized in duplicate on Nunc Amino™ plates and detected with mAbs followed by HRP-anti-mIg mAb, as shown in FIG. 6B. As shown in FIG. 6B, all the Ni-purified proteins were detected with anti-tag mAbs, but anti-mesothelin 4H3 mAb only bound to the proteins secreted by yeast co-transformed with mesothelin cDNA while anti-CA125 X52 mAb only bound to the proteins secreted by yeast co-transformed with MUC16 repeat sequence. These yeast were mated with pTOR-BIR (SEQ ID NO:9) carrying yeast to obtain diploids able to secrete in vivo biotinylated proteins. Proteins secreted by diploid yeast were Ni-purified, immobilized in duplicate on Streptavidin Immobilizer™ plates and detected with mAbs followed by HRP-anti-mIg as shown in FIG. 6C. As a negative control, HRP-anti mIg mAb was incubated with the immobilized recombinant proteins only. The results shown in FIG. 6C demonstrate that proteins secreted by diploid yeast were in vivo biotinylated because they bound to streptavidin-coated plastic, and tagged with V5 and HIS. As shown in FIG. 6B, in vivo biotinylated mesothelin and MUC16 repeat proteins were detected by anti-mesothelin 4H3 mAb or anti-CA125 U52 mAb, respectively. These proteins were also weakly detected by their respective mAbs, anti-mesothelin OV569 and anti-CA125 X306.

These results demonstrate that diploid yeast were able to secrete in vivo biotinylated recombinant proteins with tertiary structure comparable to native proteins. Diploid-secreted mesothelin clone #7 (b-meso-7) and MUC16 clone #9 (b-MUC16-9) were best detected by both specific mAbs and thus were used for all subsequent experiments. The results shown in FIGS. 6A-C are representative of three independent experiments.

Flow Cytometry Analysis

Five µg/ml of Biobodies were preincubated with 1.25 µg/ml of PE-labeled streptavidin-PE (SA-PE) (Becton Dickinson (BD) Pharmingen, San Diego, Calif.) in PBS for 15 minutes at RT. MSLN-tf HEK293F cells were lifted with Versene (Invitrogen) and washed twice with PBS supplemented with 1% BSA (PBS-BSA). Cells were pelleted and $10^6$ cells were resuspended with 100 µl of biobodies premixed with SA-PE (as described in Scholler, N., et al., *J. Immunol. Methods* 317:132-143 (2006)). After 30 minutes of incubation on ice, labeled cells were washed twice in cold PBS-BSA, resuspended in PBS-BSA, and analyzed on a BD FAC-Scan Cytometer. As positive control for mesothelin expression, cells were incubated with the anti-mesothelin mAb 4H3 at 5 ug/ml followed by PE-labeled anti-mouse Ig mAb diluted at 1:100.

Results:

The yeast display-scFv library was enriched for scFv binding to b-meso-7 by two magnetic and three flow sortings. Following the last enrichment, yeast were sorted in three gates, P2, P3 and P4 as a function of their apparent antigen affinity. Yeast-display scFv were analyzed after each sorting by flow cytometry (data not shown). Yeast were tested for scFv expression with anti-c-myc mAb followed by 488 anti-mIg mAb, and for antigen binding with b-meso-7 followed by SA-PE. As negative controls, yeast were labeled with secondary reagents only.

After two magnetic sortings, only 0.16% of the yeast display scFv bound to the antigen, but the percentage of yeast that bound to b-meso-7 increased after each flow sorting. During the third flow sorting, three distinct populations of yeast-display scFv were visible (P2, P3 and P4) and were separately sorted. The Y-geometric means of P2, P3, and P4 were of 158, 221 and 419 respectively, corresponding to three distinct populations of low, medium and high affinity (Weaver-Feldhaus, J. M., et al., *Protein Eng. Des. Sel.* 11:527-536 (2005)). The P2, P3 and P4 yeast-display scFv pools were cotransformed into yeast with pTOR2 (SEQ ID NO:1) to obtain yeast-secreted scFv and yeast colonies were selected on uracil-deficient agar plates.

Cell Adhesion Assays

Cell adhesion assays were performed as previously described (Scholler, N., et al., *J. Immunol. Methods* 317:132-143 (2006)). Briefly described, wild-type (WT) or MSLN-tf HEK293F cells were labeled with Calcein AM from the Vybrant® Cell Adhesion Assay Kit (Invitrogen-GIBCO) for 30 minutes at 37° C. Ten ug/ml of each Biobody were preincubated with 2.5 ug/ml of streptavidin (Molecular Probes Inc., Eugene, Oreg.) in DMEM (Invitrogen) for 15 minutes at RT. HEK293F cells were washed in DMEM, resuspended in quadruplicate in the Biobody/streptavidin mix and incubated for 30 minutes at RT. As controls, assays were performed in the presence of anti-CA125 mAB X52 or of anti-mesothelin mAb 4H3. After incubation, fluorescent cells were added to OvCar3 cells adherent to a tissue culture plate and incubated for 1 hour at 37° C. Cell fluorescence was measured before washing and after every two washes with FLx800™ Multi-Detection Microplate Reader (Bio-Tek Instruments, Inc., Winooski, Vt.). Normalized values (NV) after 4 washes were calculated as ratios of fluorescence percentages before (FBW) and after wash (FAW) between analyzed samples (sample) and MSLN-transfected HEK293F cells (MSLN), thus $NV=100 \times FAW/FBW_{sample}/100 \times FAW/FBW_{MSLN}$.

Results:

282 scFv-secretor yeast colonies (94 from each of the P2, P3 and P4 populations described above) were inoculated in growth medium and induced with galactose. HIS-tagged scFv were high-throughput Ni-purified from yeast supernatants and immobilized on Nunc Amino™ plates. ScFv specific binding to b-meso-7 was tested by capture ELISA and contrasted with the non-specific binding of the scFv to b-MUC16-9 as follows. The Ni-purified scFv were immobilized in two 96-well Nunc Amino™ plates. One plate was incubated with b-meso-7 and the other one with b-MUC16-9. Captured proteins were then detected with SA-HRP followed by TMB. Optical densities were measured at 450 nm and plotted as a ratio between the optical densities at 450 nM (OD) of scFv-binding signal to b-meso-7 versus b-MUC16-9. The results are shown below in TABLE 2.

TABLE 2

Characterization of Yeast-Secreted scFv Derived From Three Yeast-Display scFv Pools (P2, P3 and P4) Enriched for Mesothelin-Binders

|  | P2 | P3 | P4 |
|---|---|---|---|
| Number of yeast clones tested | 94 | 94 | 94 |
| Number of non-reactive yeast clones | 0 | 10 | 0 |
| Ratio of mesothelin/MUC16 binding > 2 | 15 | 1 | 31 |
| Ratio of mesothelin/MUC16 binding > 5 | 1 | 1 | 5 |

As shown above in TABLE 2, all the scFv derived from P2 and P4 groups bound to b-meso-7, while only one scFv derived from the P3 group bound to b-meso-7. A third of P4 scFv bound specifically to b-meso-7 (ratio >2), and 5 P4 scFv bound specifically and strongly to b-meso-7 (ratio >5). This demonstrates a correlation between the yeast-display and yeast-secreted scFv affinity for a specific target (biomarker).

Sequencing

Fifty µl of yeast from frozen stocks were inoculated in 4 ml of growth medium supplemented in tryptophan and grown to saturation at 30° C. DNA from yeast pellets were isolated (Hoffman, C. S., et al., *Gene* 57:(2-3):267-72 (1987)) and amplified with the primers Gal1 forward (5'-aatataccctctatactt-taacgtc-3') (SEQ ID NO:29) and Cyc1 reverse (gcgtgaatg-taagcgtgac) (SEQ ID NO:30). Amplification products were sequenced using either Seq forward 5'-cgagaaaagagaggct-gaag-3' (SEQ ID NO:31) or Seq reverse 5'-ggtcatcatcaccat-cacca-3' (SEQ ID NO:32) primers by the Fred Hutchinson Cancer Research Center sequencing facility and analyzed using Vector NTI® software (Invitrogen).

Results

Twenty yeast-secreted scFv were sequenced, eleven from the P4 group (#1,#5, #7, #8, #9, #10, #12, #13, #15, #16, #20), eight from the P2 group (#2, #4, #6, #11, #14, #17, #18, #19) and one from the P3 group (#3). Sequence homologies between the scFv from the same group were very high and most scFv differed from the consensus sequence by only one point mutation in the heavy or light chain. The only exception was P4 scFv #7, which differed from the consensus with two point mutations in the light chain. The point mutations observed may have arisen during the construction of the yeast-display scFv library or which a cDNA reamplification step was used to link heavy to light chains, or during the recognition sequence amplification for cotransformation with pTOR2 into yeast-secreted scFv, despite the use of a high fidelity polymerase.

FIG. 7 shows the consensus sequence of the P2 scFv and P4 scFv, provided as SEQ ID NO:33, and SEQ ID NO:36, respectively.

The P2 consensus sequence (SEQ ID NO:33) includes a 5' gap repair site, a variable region of the heavy chain (vH) (SEQ ID NO:34); a linker region, a variable region of the light chain (vL) (SEQ ID NO:35) and a 3' gap repair site.

The P4 consensus sequence (SEQ ID NO:36) includes a 5' gap repair site, a variable region of the heavy chain (vH) (SEQ ID NO:37); a linker region, a variable region of the light chain (vL) (SEQ ID NO:38) and a 3' gap repair site.

As shown in FIG. 7, the consensus sequence of the P2 (SEQ ID NO:33) and P4 (SEQ ID NO:36) scFv groups were 64% homologous. This result suggests that the scFv from the P2 and P4 groups derived from different recognition sequences and possibly directed against different epitopes. The P3 scFv sequence was truncated and did not include the linker.

Validation of Anti-mesothelin Biobodies

The twenty scFv clones that were sequenced were mated with the pTOR-BIR carrying yeast strain to generate biobodies, which were Ni-purified and validated for their specificity to mesothelin by immunoassays and flow cytometry analysis.

Figure 8A:
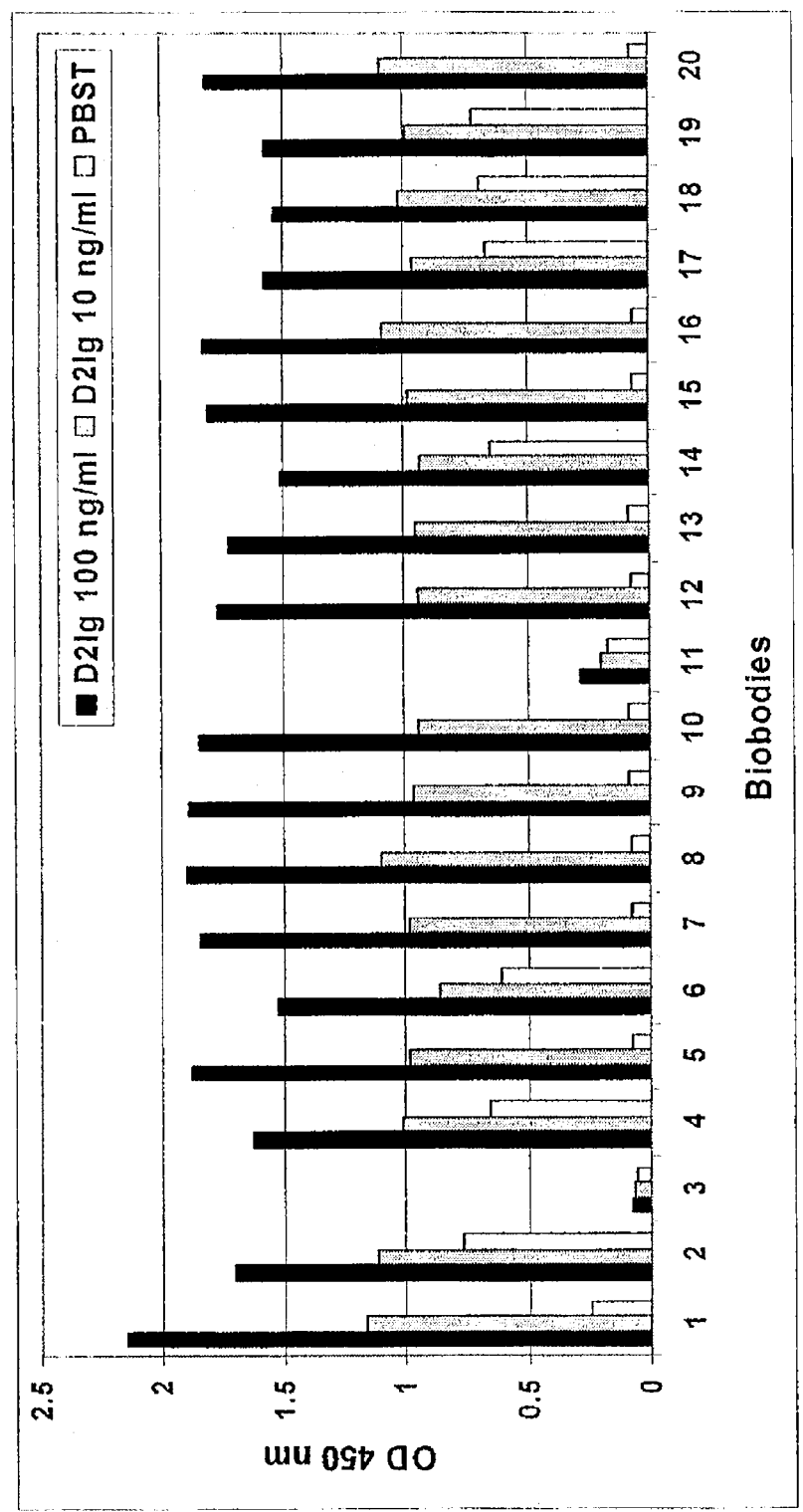
FIG. 8A shows the results of a capture ELISA in which biobodies secreted from the twenty diploid scFv pTOR-BIR clones were immobilized in a 96-well Streptavidin Immobilizer™ plate and incubated with either 100 (black bars), 10 (gray bars) or 0 (white bars) ng/ml of meso-Ig, as described in Example 4.

FIG. 8A shows the results of a capture ELISA in which biobodies secreted from the twenty diploid scFv pTOR-BIR clones were immobilized in a 96-well Streptavidin Immobilizer™ plate and incubated with either 100 (black bars), 10 (gray bars) or 0 (white bars) ng/ml of meso-Ig. Captured meso-Ig proteins were detected with HRP-anti-hIg followed by TMB. Optical densities were measured at 450 nm. The results shown are representative of two independent experiments. As shown in FIG. 8A, all biobodies but Bb#3 bound to meso-Ig by capture ELISA. Considering this result and its truncated sequence, Bb#3 was used only as a negative control during the rest of the study. As shown in FIG. 8A, P2 and P4 Bbs detected meso-Ig, yet P2 Bbs had higher background signals than P4 Bbs.

Figure 8B:
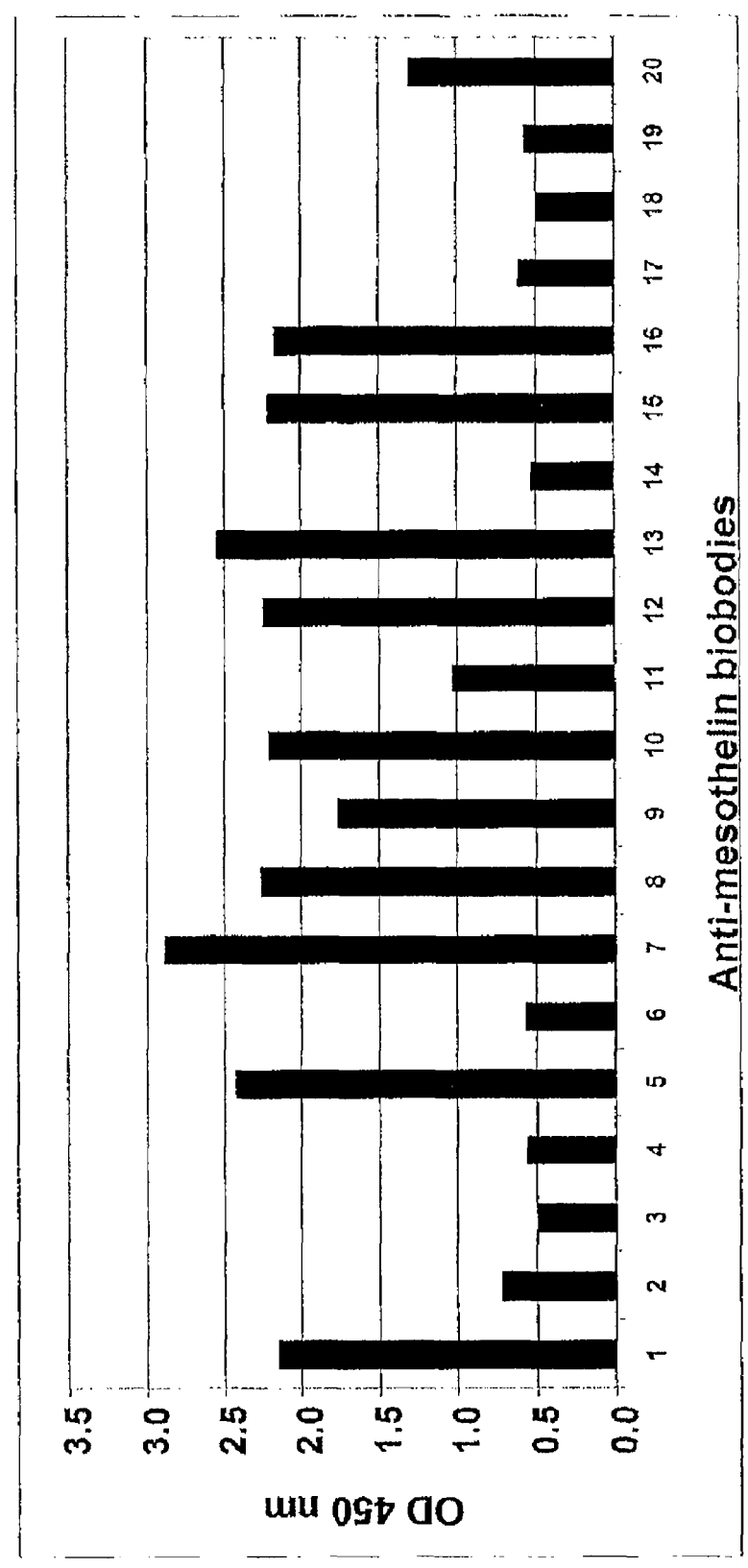
FIG. 8B shows the results of a cell ELISA in which OvCar3 cells were immobilized on poly-L-lysine coated wells and were detected with Bbs premixed with SA-polyHRP80 followed by TMB, as described in Example 4.

FIG. 8B shows the results of a cell ELISA in which OvCar3 cells were immobilized on poly-L-lysine coated wells and were detected with Bbs premixed with SA-polyHRP80 followed by TMB. Optical densities were measured at 450 nm. The results shown are representative of two independent experiments. As shown in FIG. 8B, all P4 Bbs (clone #1, #5, #7, #8, #9, #10, #12, #13, #15, #16 and #20) recognized constitutively expressed membrane-bound mesothelin as measured by cell ELISA assay. Finally, all P4 Bbs except for Bb#1 significantly bound to MSLN-transfected cells by flow cytometry analysis (data not shown).

These results demonstrate that yeast cotransformation of pools of yeast-display antigen-specific scFv recognition sequences with pTOR2 and high-throughput screening by immunoassays is an effective platform to time and cost efficiently generate antigen-specific recombinant antibodies. The capacity for in vivo biotinylation renders the reagents immediately useful in situations where biotinylated antibodies are needed.

These results also underline a positive association between high affinity mesothelin-specific yeast-display scFv and Bb specificity for membrane-bound native and soluble recombinant mesothelians.

EXAMPLE 5

This Example demonstrates that the anti-mesothelin biobodies (generated as described in Example 4) were able to block CA125/mesothelin-dependent cell attachment.

Methods: Anti-mesothelin yeast-secreted scFv and corresponding biobodies were tested for their ability to block CA125/mesothelin-dependant cell attachment in a cell adhesion assay. Ni-purified yeast-secreted scFv (FIG. 9A, black bars) or Bb/streptavidin complexes (FIG. 9B, black bars) were incubated with fluorescently labeled MSLN-transfected HEK293 cells or with WT HEK293F cells as a control. Washed Bb/streptavidin/cell complexes were then incubated with adherent OvCar3 cells (CA125-expressing cells). As controls, MSLN-tf HEK293F (positive control of binding, striped bars in FIGS. 9A, 9B), or WT HEK293F cells (negative control of binding, white bars in FIGS. 9A, 9B) were incubated with OvCar3 cells in medium only. In addition, MSLN-tfHEK293F cells were incubated in the presence of anti-mesothelin mAb 4H3 as a negative control of blocking (FIG. 9A, gray bar), or anti-CA125 mAb X52 as a positive control of blocking (FIG. 9B, gray bar). Cell fluorescence values were compared between non-treated and treated MSLN-tfHEK293F cells before and after 4 washes and the results were normalized to media only values. The results shown in FIGS. 9A and 9B are representative of three independent experiments.

Results: As previously described in Scholler, N., et al., *Cancer Letters* 2006, supra, anti-CA125 mAb X52 mAb blocked CA125/mesothelin-dependant cell attachment (see FIG. 9B), but anti-mesothelin 4H3 mAb 4H3 did not (see FIG. 9A). As shown in FIG. 9A, six yeast-secreted scFv of the P2 (#11) and P4 (#10; #12; #13; #15; #16) groups and nine biobodies (#5; #7; #8; #9; #12; #13; #15; #16; #20) all from P4 group (see FIG. 9B) decreased or blocked cell attachment.

Figure 9A:
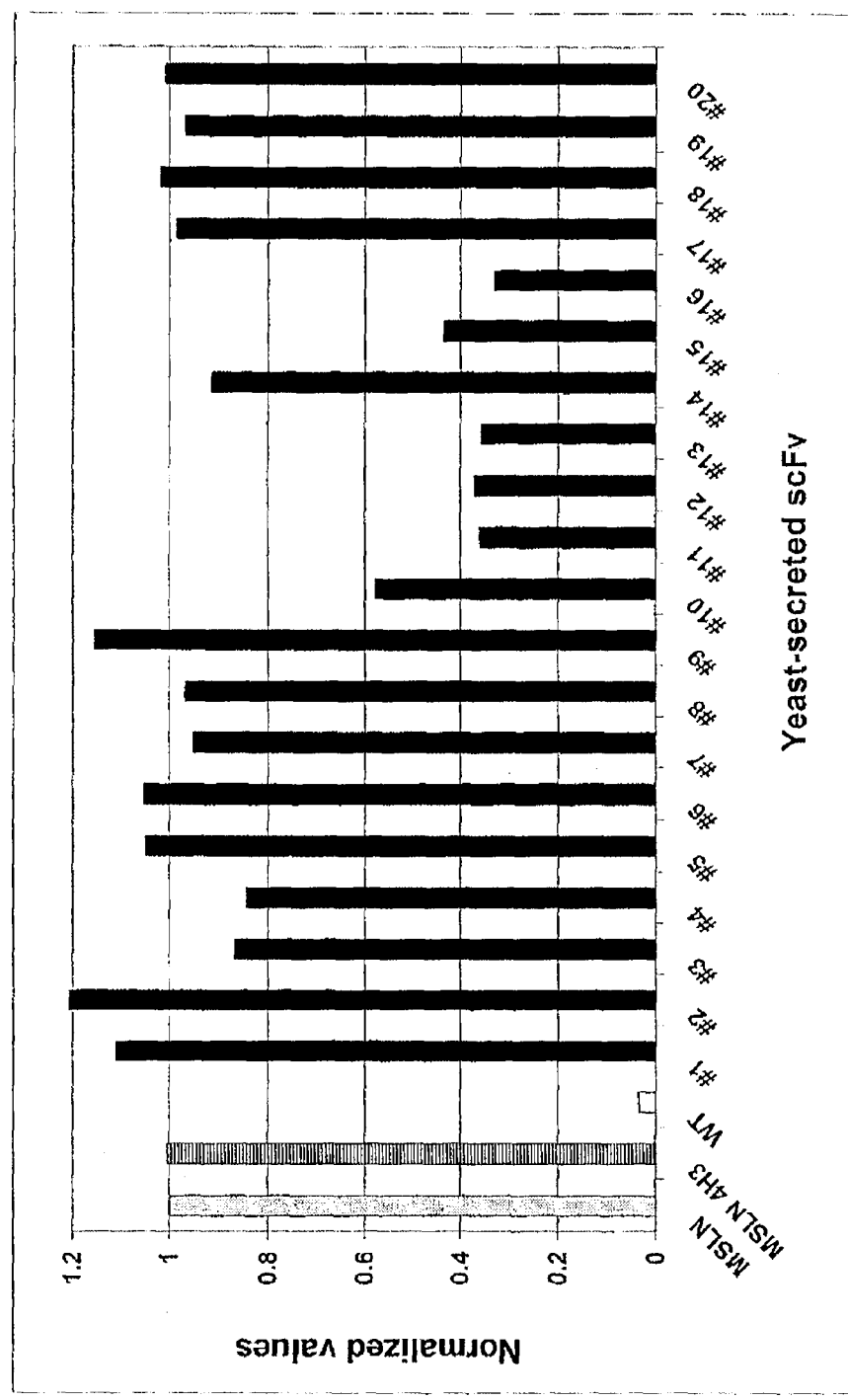
FIG. 9A graphically illustrates the results of an experiment in which Ni-purified yeast secreted scFv were tested for their ability to block CA125/mesothelin-dependant cell attachment in a cell adhesion assay, as described in Example 5.
Figure 9B:
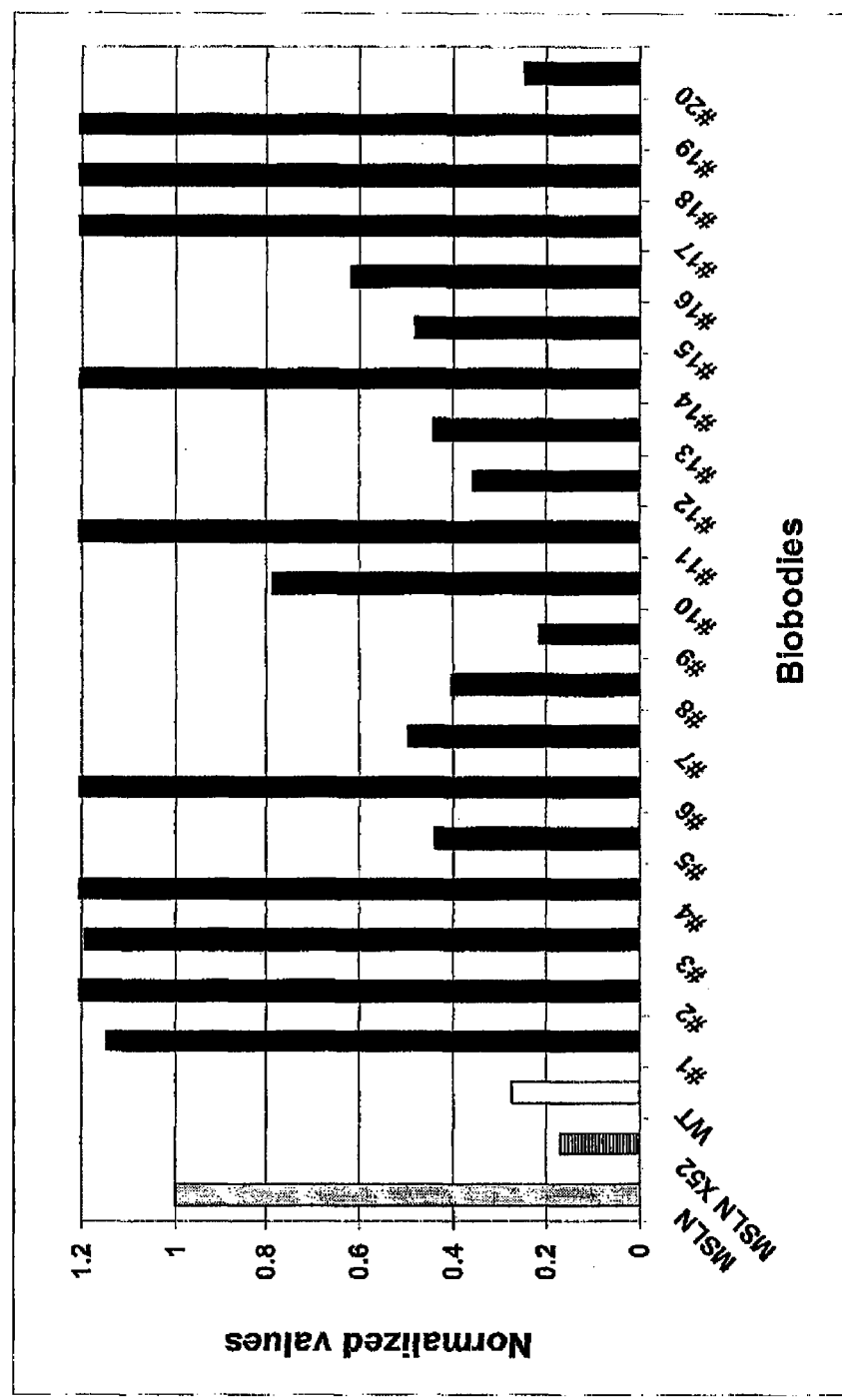
FIG. 9B graphically illustrates the results of an experiment in which Bb/streptavidin complexes were tested for their ability to block CA125/mesothelin-dependant cell attachment in a cell adhesion assay, as described in Example 5.

As shown in FIG. 9A, not all scFv binding to mesothelin were able to block the CA125/mesothelin interaction. Likewise, 4H3, a high affinity mAb raised against a native form of soluble mesothelin that recognizes all three mesothelin variants and meso-Ig (see Scholler, N., et al., *Cancer Letters* (2006); Scholler, N., et al., *Proc. Natl Acad. Sci. USA* 96:11531-11536 (1999); Hellston, I., et al., *Cancer Epidemiol Biomarkers Prev.* 15:1014-1020 (2006)), could not block CA125/mesothelin-dependent cell attachment. Although antibody affinity probably contributes to the discrepancy between antibody binding and blocking abilities, specific epitope binding is the highest determining factor.

Interestingly, it was observed that more Bbs than scFv could decrease or block cell attachment, and all the blocking Bbs belonged to the P4 group. This result suggests that 4H3 mAb and P4 Bbs are directed against different epitopes on mesothelin. These results also show that complexing Bbs with streptavidin modifies their blocking abilities, as compared with scFv. In addition, a trend is observed in which the blocking ability of the Bb increases in a manner that is consistent with Bb affinity for mesothelin. Consistent with this observation, all the Bbs that significantly interfered with CA125/mesothelin-dependent cell attachment belong to the P4 group. These results suggest that most P4 Bbs may be able to block or decrease CA125/mesothelin-dependent cell attachment in vivo, and thus could be used as therapeutic agents to prevent or reduce the peritoneal implantation of tumor cells.

Generation of anti-mesothelin Bbs that recognized native mesothelin using yeast-expressed mesothelin also validated the quality of the yeast-expressed proteins. Yeast-secreted mesothelin was detected by 4H3 mAb but was not detected by OV569 mAb, a monoclonal antibody raised against cancer ovarian cells (Scholler, N., et al., Proc. Natl Acad. Sci. USA 96:11531-11536 (1999)) that binds to native mesothelins but not to meso-Ig (data not shown). However, OV569 mAb bound weakly but significantly to in vivo biotinylated mesothelin, which implies that OV569 binding epitope became available after in vivo biotinylation. Taken together, these results suggest that OV569 mAb binds to a conformational epitope that appears after mesothelin modifications in the C-terminus, such as in vivo biotinylation or GPI-linkage. These results also suggest that antibodies specific for membrane-bound or soluble forms of mesothelin may be generated against conformational changes triggered by the GPI-anchor before and after cleavage (Butikofer, P., et al., FASEB J. 15:545-548 (2001)). Membrane-bound-specific anti-mesothelin affinity reagents would be particularly useful for targeted therapies and in vivo imaging.

In conclusion, the results of this study suggest that generating recombinant antibodies against mesothelin using the techniques described herein may be useful as therapeutic agents to prevent peritoneal implantation of ovarian carcinoma cells and thus prevent recurrent metastatic disease.

EXAMPLE 6

This Example describes a subtractive approach to identify Biobodies (Bbs) specific for E. histolytica antigens that are differentially expressed in a complex sample containing E. histolytica Ags and E. dispar.

Methods:

I. Generation of a Yeast-display scFv (YD scFv) Sublibrary Enriched for YD scFv that Bind to E. histolytica Ags 1. Cell lysates are prepared from E. histolytica and from E. dispar at 100 ug/ml and are dialyzed against phosphate buffered saline (PBS) overnight (ON) at 4° C. The cell lysates are biotinylated with EZ-link sulfo-NHS LC biotin kit (Fisher/Pierce) and dialyzed against PBS ON at 4° C. The lysates are aliquotted and stored at −80° C.

2. A yeast surface display scFv library is prepared as described in Feldhaus, M. J., et al., Nat. Biotechnol. 21:163-70 (2003). Briefly described, $10^{10}$ YD scFv are grown to saturation in 1 liter of SD-CAA yeast medium. scFv expression is induced at the yeast-cell surface by inoculating grown yeast in 1 liter of medium supplemented with galactose (SGR-CAA) at an OD of 0.5 at 600 nm. When the optical density of the culture reaches 1.0 the culture is resuspended in 10 ml of PBS supplemented with 0.5% BSA and 10 mM EDTA (PBE).

3. First Magnetic Sorting: 10 ml of the induced yeast are incubated with 100 ug/ml of biotinylated E. histolytica cell lysate for 30 min at 4° C., to form yeast display (YD) scFv/biotinylated E. histolytica cell lysate complexes which are then washed 3 times in PBE. The YD scFv/biotinylated E. histolytica cell lysate complexes are then incubated with 200 ul of streptavidin-coated magnetic beads (Miltenyi) for 15 min at 4° C. and washed 3 times in PBE. The YD scFv/biotinylated E. histolytica cell lysate/streptavidin-coated magnetic bead complexes are retrieved with a magnetic column (LS. Miltenyi) in 7 ml of PBE and the retrieved yeast are resuspended in 200 ml SD-CAA. 1 ul and 10 ul of the retrieved yeast are plated on a SD-CAA agar plate and incubated for 2 days at 30° C. in order to evaluate the library enrichment (expected to be ×100 to ×500; in other words, $10^7$ to $5 \times 10^7$ yeast should be selected by the first magnetic sorting).

The retrieved yeast are grown at 30° C. until saturation, an aliquot is frozen, and another aliquot is used to inoculate a 200 ml culture of SGR-CAA is as previously described to induce scFv expression at the yeast surface.

4. Second magnetic sorting and first flow sorting: The yeast from the 200 ml culture inoculated and induced from the first magnetic sorting are resuspended in 3 ml, incubated with 100 ug/ml of biotinylated E. histolytica cell lysate for 30 min at 4° C., and washed 3 times in PBE to generate YD scFv/biotinylated E. histolytica cell lysate complexes. The YD scFv/biotinylated E. histolytica cell lysate complexes are then incubated with 100 ul of anti-biotin-coated magnetic beads (Miltenyi) for 15 min at 4° C. and washed 3 times in PBE.

The YD scFv/biotinylated E. histolytica cell lysate/anti-biotin-coated magnetic bead complexes are retrieved with a magnetic column (LS. Miltenyi) in 7 ml of PBE. The retrieved yeast are then centrifuged, and resuspended in 0.6 ml of PBE. 0.55 ml of the magnetic sorted yeast are incubated with 5 ul of anti-c-myc mouse monoclonal antibody (sc-40, Santa Cruz) to label cmyc-tagged scFv-expresser yeast, 30 min at 4° C., then washed 3 times with PBE and resuspended in 550 ul of PBE.

500 ul of the c-myc labeled yeast are incubated with 2 ul of 488 labeled anti-mouse Ig (#A11017 INVITROGEN) to detect anti-c-myc mAb bound to the scFv tag and 1 ul of streptavidin PE to detect biotinylated cell lysate bound to YD scFv, for 30 min at 4° C. As a control to measure scFv expression, 50 ul of c-myc labeled YD scFv is incubated with 0.2 ul of 488 labeled anti-mouse Ig. As a negative control, 50 ul of the left-over retrieved yeast is incubated with 488 labeled anti-mouse Ig only. The double-labeled yeast are flow sorted into 100 ul of complete medium YEPD and resuspended in 50 ml of SD-CAA and grown until saturation at 30° C.

5. Second and last flow sorting: All incubations are carried out for 30 min at 4° C. The double-labeled yeast grown as described above are centrifuged, an aliquot is saved at −80° C. the rest are induced as previously described. The induced yeast are resuspended in 1 ml of PBE. 0.1 ml of yeast are incubated with 5 ul of anti-cmyc mouse monoclonal antibody and with 100 ug/ml of biotinylated E. histolytica cell lysate in a final volume of 500 ul in PBE. As an expression control, 10 ul of yeast is incubated with 0.5 ul of anti-c myc mAb in a final volume of 50 ul in PBE. The yeast are washed 3 times with PBE and resuspended in 500 ul and 50 ul of PBE respectively.

The c-myc/biotinylated *E. histolytica* cell lysate-labeled yeast is incubated with 2 ul of 488 labeled anti-mouse Ig and 1 ul of streptavidin PE. For the expression control and the negative control, 10 ul of the c-myc labeled yeast and 10 ul of the left-over induced yeast are incubated with 0.2 ul of 488 labeled anti-mouse Ig and 0.1 ul of streptavidin PE, respectively, in a final volume of 50 ul of PBE. The double-labeled yeast are flow sorted in 100 ul of complete medium YEPD, resuspended in 50 ml of SD-CAA and grown until saturation at 30° C.

6. Validation by flow cytometry analysis: All incubations are carried for 30 minutes at 4° C. The yeast are centrifuged, an aliquot is stored at −80° C., and the rest is induced as previously described. The induced yeast are resuspended in 1 ml of PBE. 10 ul of the yeast is incubated with 0.5 ul of anti-cmyc mAb and with 100 ug/ml of biotinylated *E. histolytica* cell lysate in a final volume of 50 ul in PBE. As expression control, 10 ul of yeast is incubated with 0.5 ul of anti-c-myc mouse monoclonal antibody in a final volume of 50 ul in PBE. The yeast samples are washed 3 times with PBE and resuspended in 50 ul of PBE.

The c-myc/biotinylated *E. histolytica* cell lysate-labeled yeast are incubated with 0.2 ul of 488 labeled anti-mouse Ig and 0.1 ul of streptavidin PE. For the expression control and the negative control, 10 ul of the c-myc labeled yeast and 10 ul of the left-over induced yeast are incubated with 0.2 ul of 488 labeled anti-mouse Ig and 0.1 ul of streptavidin PE, respectively, in a final volume of 50 ul of PBE.

The three samples are analyzed by flow cytometry. It is expected that all negative control yeast will be in the lower left quadrant; about half of the expression control yeast will be in the lower left quadrant and the other half in the lower right quadrant. It is expected that less than half of the c-myc/biotinylated *E. histolytica* cell lysate-labeled yeast should be in the lower left quadrant while at least 40% of them should be in the upper right quadrant, demonstrating that most of the selected YD scFv bind to *E. histolytica*. If less than 20% of yeast express scFv, the YD scFv will be sorted using c-myc magnetic beads. If less than 70% of yeast that express scFv bind to *E. histolytica*, the yeast will be sorted again to obtain a sublibrary strongly enriched for YD scFv that bind to *E. histolytica*. Assuming the selected YD scFv meet the above criteria, then the protocol proceeds to the depletion for scFv that bind to *E. dispar*, as described in detail below.

II. Generation of *E. Histolytica* Ags-specific YD scFv Sublibrary

All incubations are carried for 30 min at 4° C.

1. Magnetic Depletion of the YD scFv that bind to *E. Dispar*

$10^8$ of induced YD scFv that have been enriched for binding to *E. histolytica* cell lysate are resuspended in 1 ml of PBE, incubated with 100 ug/ml of biotinylated *E. dispar* cell lysate, washed 3 times and resuspended in 1 ml of PBE. The yeast are then incubated with 50 ul of streptavidin-coated beads and washed 3 times. The YD scFv that bind to biotinylated *E. dispar* cell lysate are removed using a magnetic depletion column (Miltenyi), and only the yeast in the effluent are saved.

2. Magnetic Enrichment for scFv Expressers

The yeast saved from effluent are centrifuged, resuspended in 0.5 ml of PBE, incubated with 50 ul of c-myc-coated magnetic beads (Miltenyi), and washed 3 times. The c-myc bead-bound YD scFv are retrieved with a magnetic column in 7 ml of PBE. The retrieved yeast are resuspended in 50 ml SD-CAA and grown until saturation. An aliquot is frozen and another aliquot is used to inoculate 20 ml of SGR-CAA as previously described to induce scFv expression at the yeast surface.

3. Validation by Flow Cytometry Analysis

All incubations are carried for 30 min at 4° C. The induced yeast are resuspended in 1 ml of PBE. Ten ul of yeast is incubated with 0.5 ul of anti-c-myc mouse monoclonal antibody and with 100 ug/ml of biotinylated *E. histolytica* cell lysate in a final volume of 50 ul in PBE. As a control for specificity, 10 ul of yeast is incubated with 0.5 ul of anti-cmyc mouse monoclonal antibody and with 100 ug/ml of biotinylated *E. dispar* cell lysate in a final volume of 50 ul in PBE. As an expression control 10 ul of yeast is incubated with 0.5 ul of anti-c-myc mouse monoclonal antibody in a final volume of 50 ul in PBE. The yeast are washed 3 times with PBE and resuspended in 50 ul of PBE.

The c-myc/cell lysate-labeled yeast are incubated with 0.2 ul of 488 labeled anti-mouse Ig and 0.1 ul of streptavidin PE. For the expression control and the negative control, 10 ul of c-myc labeled yeast and 10 ul of the left-over induced yeast are incubated with 0.2 ul of 488 labeled anti-mouse Ig and 0.1 ul of streptavidin PE, respectively, in a final volume of 50 ul of PBE. The yeast are washed 3 times with PBE and resuspended in 50 ul of PBE.

The four samples are analyzed by flow cytometry. Positive, negative and expression controls are expected to behave as previously described above. In addition, about half of the yeast of the c-myc/biotinylated *E. dispar* cell lysate-labeled yeast are expected to be in the lower left quadrant while the other half should be mostly in the lower right quadrant. It is expected that only 5% or less of the yeast should be in the upper right quadrant, demonstrating that most of the selected YD scFv bind to *E. histolytic* but not to *E. dispar*. If it is not the case, the YDscFv are resorted to more completely deplete the non-specific binders.

Assuming the YDscFv meet the criteria described above, then the *E. histolytica* Ags-specific YD scFv sublibrary is transformed into biobodies as described below.

III. Generation and Validation of *E. Histolytica* Ags-Specific Biobodies

1. Yeast-cotransformation with pTOR2 and *E. Histolytica* Ags-specific scFv Recognition Sequences The *E. histolytica* Ags-specific scFv recognition sequences are PCR amplified with vector specific primers, as described in Example 2. The PCR fragments are gel purified and yeast are cotransformed with the PCR fragments and Sfi1-Not1 linearized pTOR2 (SEQ ID NO:1). Transformed yeast colonies are then arrayed in 96 well plates in liquid medium and grown to saturation.

2. Mating of Cotransformed Yeast with pTORBIR Bearing Yeast

Uracil-prototroph cotransformed yeast obtained as described above are mated with tryptophan-prototroph pTOR-BIR (SEQ ID NO:9) bearing yeast in rich medium. Diploids are selected as uracil/tryptophan-prototrophs on agar plates. The diploids are then grown in liquid medium to saturation in 2 ml-96 well plates. Aliquots are frozen and an aliquot is used to inoculate 1 ml of culture in a 2 ml-96 well plates of SGR-CAA as previously described to induce the biobody secretion.

3. Validation of *E. Histolytica* Specific Biobodies

All incubations are carried for 30 min at 4° C. 96 well plates of *E. histolytica* and *E. dispar* live cells are prepared at $5 \times 10^5$ cells/well. 4 wells of each cell type per Biobody to validate is prepared with 2 wells of non-permeabilized cells and 2 wells of permeabilized cells.

The inducted yeast diploids are centrifuged in the 2 ml-96 well plates. Supernatants are taken off the diploids that contain biobodies and saved in clean plates. Yeast supernatants do not contain proteases and thus can be kept up to 2 weeks at 4° C. without noticeable protein degradation. 220 ul of diploid supernatant is incubated with 1/100 of PE-labeled streptavidin in U-bottom 96 well plates as described in Scholler, N., et al., *J. Immunol. Methods* 317:132-143 (2006). *E. histolytica* and *E. dispar* live cells are centrifuged, cell medium is removed and the cells are resuspended in 25 ul of PBE. 25 ul of diploid supernatant premixed with PE-labeled streptavidin is added per well, in 8 wells (2 of *E. histolytica* and 2 of *E. dispar* non-permeabilized cells and 2 of *E. histolytica* and 2 of *E. dispar* permeabilized cells) and incubated. The cells are washed 3 times with PBE and analyzed by flow cytometry analysis.

It is expected that diploid supernatants containing *E. histolytica*-specific biobodies will label *E. histolytica* but not *E. dispar*. Biobodies will label permeabilized cells if the bound epitopes are intracellular, and both permeabilized and non-permeabilized cells if bound epitopes are at the cell surface.

4. Purification of *E. Histolytica*-Specific Biobodies

Validated biobodies are grown and induced in 200 ml and purified by nickel column as described in Scholler, N., et al., *J. Immunol. Methods* 317:132-143 (2006). The average yield of biobodies is expected to be between 1 to 10 mg/L.

IV. Follow-Up Studies to Characterize Novel *E. Histolytica*-Specific Antigens

The purified biobodies may be used to characterize novel *E. histolytica*-specific antigens using binding affinity analysis as described in Examples 2-5, immunoprecipitation analysis and ELISA assay as described below.

1. Immunoprecipitation Analysis

Two immunoprecipitations (IP)s are prepared as follows. 8 ug of purified anti-*E. histolytica* Biobody is mixed with 800 ug of *E. histolytica* cell lysate and incubated ON at 4° C. with rotation. 8 ug of purified anti-*E. histolytica* Biobody is mixed with 800 ug of *E. dispar* cell lysate and incubated ON at 4° C. with rotation. 100 ul of streptavidin-magnetic beads is added per immunoprecipitation and incubated for 1 hour at 4° C. with rotation. Each captured antigen pool is eluted with a MACS separation micro column (Miltenyi) in 50 ul. The eluates are loaded on a protein gel and separated by electrophoresis. The protein gel is then silver stained and the eluates are cut in identical ¼ inches slices and analyzed by mass spectroscopy. The mass spectroscopy data for the immunoprecipitations of *E. histolytica* vs. *E. dispar* is then compared using the Computational Proteomics Analysis System (CPAS) site, as described in Rauch, A., et al., *J. Proteome Res.* 5:112-21 (2006).

2. Sandwich ELISA Assay with *E. Histolytica*-specific Biobodies

A pool of validated, Ni-purified *E. histolytica*-specific biobodies are prepared as described above by mixing all the validated biobodies in PBS at 10 ug/ml. The pool is then screened for the identification of biobody pairs as described below.

First Orientation:

Streptavidin plates are prewashed 3 times with 200 ul of PBST. 5 ug/ml of validated, Ni-purified *E. histolytica*-specific biobodies are immobilized on 2 streptavidin plates in 100 ul of PBST (2 wells per Biobody per plate), incubated for one hour at RT with gentle rotation, and washed 3 times with PBST.

*E. histolytica* vs. *E. dispar* cell lysates diluted 2 times in PBST in duplicate (1 plate with *E. histolytica* and 1 plate with *E. dispar*) are incubated for one hour RT with gentle rotation and washed 3 times with PBST.

Detection is carried out with 5 ug/ml of the pool of *E. histolytica*-specific biobodies that was premixed with 1 ug/ml of polyHRP-labeled streptavidin (RDI).

Second Orientation:

This protocol is similar to the First Orientation with the difference that the *E. histolytica*-specific Biobody pool is immobilized on streptavidin plates and the antigens are detected with *E. histolytica*-specific biobodies premixed with polyHRP-labeled streptavidin.

Optional Random Mutagenesis Step:

If clones are not identified that generate a desired signal intensity, such as an optical density ratio of *E. histolytica* versus *E. dispar*>10, then the best candidate biobodies may be matured by random mutagenesis as described below.

The scFv recognition sequences of the highest affinity biobodies identified in the ELISA assay protocol described above are PCR amplified using Genemorph II EZClone Domain Mutagenesis kit (Stratagene). The mutagenized scFv recognition sequences are then used to generate and validate matured biobodies as described above, which are then screened for the identification of biobody pairs for use in an ELISA assay as described above in section IV.2.

While illustrative embodiments have been illustrated and described, it will be appreciated that various changes can be made therein without departing from the scope of the invention.

---

The embodiments of the invention in which an exclusive property or privilege is claimed are defined as follows:

1. A vector for expressing a secreted biotinylated polypeptide in yeast, comprising:
   an insertion site for inserting a nucleic acid sequence encoding a polypeptide to be expressed;
   (ii) a nucleic acid sequence encoding a yeast secretory leader amino acid sequence located adjacent to the 5' end of the insertion site;
   (iii) a nucleic acid sequence encoding a biotin acceptor site comprising SEQ ID NO:7 for golgi-localized biotin ligase fused to the 3' or 5' end of the insertion site; and
   (iv) nucleic acid sequences allowing for autonomous replication and selection in yeast.

2. The vector of claim 1, further comprising a nucleic acid sequence encoding a flexible linker fused in frame between the insertion site and the biotin acceptor site.

3. The vector of claim 1, further comprising a nucleic acid sequence encoding a biotin ligase and a nucleic acid sequence encoding at least one golgi localization domain of a golgi-targeted protein, wherein the nucleic acid sequence encoding at least one golgi localization domain is operatively linked to the nucleic acid sequence encoding the biotin ligase.

4. The vector of claim 2, wherein the flexible linker comprises the human IgA1 hinge comprising SEQ ID NO:5.

5. The vector of claim 1 comprising SEQ ID NO:1.

6. The vector of claim 1, further comprising a nucleic acid sequence encoding a polypeptide to be expressed inserted into the insertion site.

7. The vector of claim 6 wherein the polypeptide to be expressed is selected from the group consisting of a recombinant protein, an antibody, an antibody fragment antigen binding region (Fab), an antibody fragment variable region (Fv), nanobody and a single chain fragment variable (scFv) recognition sequence.

8. A yeast cell comprising the vector of claim 6.

9. A vector for expressing recombinant golgi-localized biotin ligase in yeast, comprising:
   (i) a nucleic acid sequence encoding a biotin ligase;
   (ii) a nucleic acid sequence comprising at least one of SEQ ID NO:15 and SEQ ID NO:18, wherein the nucleic acid encodes at least one golgi localization domain of a yeast protease KEX2p protein, wherein the nucleic acid sequence encoding the at least one golgi localization domain is operatively linked to the nucleic acid sequence encoding the biotin ligase; and
   (iii) nucleic acid sequences allowing for autonomous replication and selection in yeast.

10. The vector of claim 9, wherein the biotin ligase is *E. Coli* biotin ligase (BirA).

11. The vector of claim 10, wherein the nucleic acid encoding the biotin ligase comprises SEQ ID NO:10.

12. The vector of claim 9, wherein the vector comprises SEQ ID NO:9.

13. A yeast cell comprising the vector of claim 9.

14. A kit for expressing a secreted biotinylated polypeptide in yeast, the kit comprising:

(1) a first vector for expressing a secreted polypeptide comprising a biotin acceptor site, the first vector comprising:
   (i) an insertion site for inserting a nucleic acid sequence encoding a polypeptide to be expressed;
   (ii) a nucleic acid sequence encoding a yeast secretory leader amino acid sequence located adjacent to the 5' end of the insertion site;
   (iii) a nucleic acid sequence encoding a biotin acceptor site comprising SEQ ID NO:7 for a golgi-localized biotin ligase fused to the 3' or 5' end of the insertion site; and
   (iv) nucleic acid sequences allowing for autonomous replication and selection in yeast; and
(2) a second vector for expressing the golgi-localized biotin ligase in yeast, the second vector comprising:
   (i) a nucleic acid sequence encoding the biotin ligase;
   (ii) a nucleic acid sequence encoding at least one golgi localization domain of a golgi-targeted protein, wherein the nucleic acid sequence encoding at least one golgi localization domain is operatively linked to the nucleic acid sequence encoding the biotin ligase; and
   (iii) nucleic acid sequences allowing for autonomous replication and selection in yeast.

15. A vector comprising a nucleic acid sequence encoding a recombinant polypeptide comprising a human IgA1 hinge set forth as SEQ ID NO:5 fused in frame to a biotin acceptor site set forth as SEQ ID NO:7.

* * * * *

UNITED STATES PATENT AND TRADEMARK OFFICE
CERTIFICATE OF CORRECTION

| | | |
|---|---|---|
| PATENT NO. | : 7,795,411 B2 | |
| APPLICATION NO. | : 11/669811 | |
| DATED | : September 14, 2010 | |
| INVENTOR(S) | : N. Scholler et al. | |

It is certified that error appears in the above-identified patent and that said Letters Patent is hereby corrected as shown below:

| COLUMN | LINES | |
|---|---|---|
| 1 | 17-18 | "The Government may have certain rights in the invention." should read<br>--The Government has certain rights in the invention.-- |

Signed and Sealed this
Twenty-first Day of February, 2012

David J. Kappos
*Director of the United States Patent and Trademark Office*

SEQUENCE LISTING

<160> NUMBER OF SEQ ID NOS: 38

<210> SEQ ID NO 1
<211> LENGTH: 4977
<212> TYPE: DNA
<213> ORGANISM: Artificial Sequence
<220> FEATURE:
<223> OTHER INFORMATION: Synthetic

<400> SEQUENCE: 1

```
ctagtacgga ttagaagccg ccgagcgggt gacagccctc cgaaggaaga ctctcctccg      60
tgcgtcctcg tcttcaccgg tcgcgttcct gaaacgcaga tgtgcctcgc gccgcactgc     120
tccgaacaat aaagattcta caatactagc ttttatggtt atgaagagga aaaattggca     180
```

-continued

```
gtaacctggc cccacaaacc ttcaaatgaa cgaatcaaat taacaaccat aggatgataa    240
tgcgattagt ttttagcct tatttctggg gtaattaatc agcgaagcga tgattttga     300 tctattaaca gatatataaa tgcaaaaact gcataaccac tttaactaat actttcaaca   360
ttttcggttt gtattacttc ttattcaaat gtaataaaag tatcaacaaa aaattgttaa   420
tatacctcta tactttaacg tcaaggagaa aaaccccggg atcggactac tagcagctgt   480
aatacgactc actataggga atattaagct tatgagattt ccttcaattt ttactgctgt   540
tttattcgca gcatcctccg cattagctgc tccagtcaac actacaacag aagatgaaac   600
ggcacaaatt ccggctgaag ctgtcatcgg ttactcagat ttagaagggg atttcgatgt   660
tgctgttttg ccattttcca acagcacaaa taacgggtta ttgtttataa atactactat   720
tgccagcatt gctgctaaag aagaagggt atctctcgag aaaagagagg ctgaagctga   780
ttataaagat gacgataaag gtggtggtgg ttctgctagc gcggccgcgg cctcaggggc   840
ctccggaatt ctagaacaac agggtaagcc tatccctaac cctctcctcg gtctcgattc   900
tacgcgtacc ggtcatcatc accatcacca tccatcaaca ccaccaactc caagtccttc   960
tactcctcct acaccttcac catcaggttt gaatgatatt tttgaagctc aaaaaattga   1020
atggcatgaa tgagttttaaa cccgctgatc ctagagggcc gcatcatgta attagttatg   1080
tcacgcttac attcacgccc tccccccaca tccgctctaa ccgaaaagga aggagttaga   1140
caacctgaag tctaggtccc tatttatttt tttatagtta tgttagtatt aagaacgtta   1200
tttatatttc aaattttct tttttttctg tacagacgcg tgtacgcatg taacattata   1260
ctgaaaacct tgcttgagaa ggttttggga cgctcgaagg ctttaatttg caagctgcgg   1320
ccctgcatta atgaatcggc caacgcgcgg ggagaggcgg tttgcgtatt gggcgctctt   1380
ccgcttcctc gctcactgac tcgctgcgct cggtcgttcg gctgcggcga gcggtatcag   1440
ctcactcaaa ggcggtaata cggttatcca cagaatcagg ggataacgca ggaaagaaca   1500
tgtgagcaaa aggccagcaa aagcccagga accgtaaaaa ggccgcgttg ctggcgtttt   1560
tccataggct ccgccccct gacgagcatc acaaaaatcg acgctcaagt cagaggtggc   1620
gaaacccgac aggactataa agataccagg cgtttccccc tggaagctcc ctcgtgcgct   1680
ctcctgttcc gaccctgccg cttaccggat acctgtccgc ctttctccct tcgggaagcg   1740
tggcgctttc tcatagctca cgctgtaggt atctcagttc ggtgtaggtc gttcgctcca   1800
agctgggctg tgtgcacgaa ccccccgttc agcccgaccg ctgcgcctta tccggtaact   1860
atcgtcttga gtccaacccg gtaagacacg acttatcgcc actggcagca gccactggta   1920
acaggattag cagagcgagg tatgtaggcg gtgctacaga gttcttgaag tggtggccta   1980
actacggcta cactagaagg acagtatttg gtatctgcgc tctgctgaag ccagttacct   2040
tcggaaaaag agttggtagc tcttgatccg gcaaacaaac caccgctggt agcggtggtt   2100
tttttgtttg caagcagcag attacgcgca gaaaaaaagg atctcaagaa gatcctttga   2160
tcttttctac ggggtctgac gctcagtgga acgaaaactc acgttaaggg attttggtca   2220
tgagattatc aaaaaggatc ttcacctaga tccttttaaa ttaaaaatga agttttaaat   2280
caatctaaag tatatatgag taaacttggt ctgacagtta ccaatgctta atcagtgagg   2340
cacctatctc agcgatctgt ctatttcgtt catccatagt tgcctgactc cccgtcgtgt   2400
agataactac gatacgggag cgcttaccat ctggccccag tgctgcaatg ataccgcgag   2460
acccacgctc accggctcca gatttatcag caataaacca gccagccgga agggccgagc   2520
```

```
gcagaagtgg tcctgcaact ttatccgcct ccatccagtc tattaattgt tgccgggaag    2580
ctagagtaag tagttcgcca gttaatagtt tgcgcaacgt tgttggcatt gctacaggca    2640
tcgtggtgtc actctcgtcg tttggtatgg cttcattcag ctccggttcc caacgatcaa    2700
ggcgagttac atgatccccc atgttgtgca aaaaagcggt tagctccttc ggtcctccga    2760
tcgttgtcag aagtaagttg gccgcagtgt tatcactcat ggttatggca gcactgcata    2820
attctcttac tgtcatgcca tccgtaagat gcttttctgt gactggtgag tactcaacca    2880
agtcattctg agaatagtgt atgcggcgac cgagttgctc ttgcccggcg tcaatacggg    2940
ataatagtgt atcacatagc agaactttaa aagtgctcat cattggaaaa cgttcttcgg    3000
ggcgaaaact ctcaaggatc ttaccgctgt tgagatccag ttcgatgtaa cccactcgtg    3060
cacccaactg atcttcagca tcttttactt tcaccagcgt ttctgggtga gcaaaaacag    3120
gaaggcaaaa tgccgcaaaa aagggaataa gggcgacacg gaaatgttga atactcatac    3180
tcttcctttt tcaatgggta ataactgata taattaaatt gaagctctaa tttgtgagtt    3240
tagtatacat gcatttactt ataatacagt tttttagttt tgctggccgc atcttctcaa    3300
atatgcttcc cagcctgctt ttctgtaacg ttcaccctct accttagcat cccttcccct    3360
tgcaaatagt cctcttccaa caataataat gtcagatcct gtagagacca catcatccac    3420
ggttctatac tgttgaccca atgcgtctcc cttgtcatct aaaccacac cgggtgtcat    3480 aatcaaccaa tcgtaacctt catctcttcc acccatgtct ctttgagcaa taaagccgat    3540
aacaaaatct ttgtcgctct tcgcaatgtc aacagtaccc ttagtatatt ctccagtaga    3600
tagggagccc ttgcatgaca attctgctaa catcaaaagg cctctaggtt cctttgttac    3660
ttcttctgcc gcctgcttca aaccgctaac aatacctggg cccaccacac cgtgtgcatt    3720
cgtaatgtct gcccattctg ctattctgta tacacccgca gagtactgca atttgactgt    3780
attaccaatg tcagcaaatt ttctgtcttc gaagagtaaa aaattgtact tggcggataa    3840
tgcctttagc ggcttaactg tgccctccat ggaaaaatca gtcaagatat ccacatgtgt    3900
ttttagtaaa caaatttttgg gacctaatgc ttcaactaac tccagtaatt ccttggtggt    3960
acgaacatcc aatgaagcac acaagtttgt ttgcttttcg tgcatgatat taaatagctt    4020
ggcagcaaca ggactaggat gagtagcagc acgttcctta tatgtagctt tcgacatgat    4080
ttatcttcgt ttcctgcagg ttttttgttct gtgcagttgg gttaagaata ctgggcaatt    4140 tcatgttttct tcaacactac atatgcgtat atataccaat ctaagtctgt gctccttcct    4200
tcgttcttcc ttctgttcgg agattaccga atcaaaaaaa tttcaaagaa accgaaatca    4260 aaaaaagaa taaaaaaaaa atgatgaatt gaattgaaaa gctagcttat cgatgggtcc    4320
ttttcatcac gtgctataaa aataattata atttaaattt tttaatataa atatataaat    4380
taaaaataga agtaaaaaa agaaattaaa gaaaaatag tttttgtttt ccgaagatgt    4440
aaaagactct aggggatcg ccaacaaata ctacctttta tcttgctctt cctgctctca    4500
ggtattaatg ccgaattgtt tcatcttgtc tgtgtagaag accacacacg aaaatcctgt    4560 gatttttacat tttacttatc gttaatcgaa tgtatatcta tttaatctgc ttttcttgtc    4620
taataaatat atatgtaaag tacgcttttt gttgaaattt tttaaacctt tgttttatttt    4680 tttttcttca ttccgtaact cttctacctt ctttatttac tttctaaaat ccaaatacaa    4740
aacataaaaa taaataaaca cagagtaaat tcccaaatta ttccatcatt aaaagatacg    4800
aggcgcgtgt aagttacagg caagcgatcc gtccgccggc gaacgtggcg agaaaggaag    4860
ggaagaaagc gaaaggagcg ggggctaggg cggtgggaag tgtagggtc acgctgggcg    4920
```

```
taaccaccac acccgccgcg cttaatgggg cgctacaggg cgcgtgggga tgatcca       4977

<210> SEQ ID NO 2
<211> LENGTH: 4884
<212> TYPE: DNA
<213> ORGANISM: Artificial Sequence
<220> FEATURE:
<223> OTHER INFORMATION: Synthetic

<400> SEQUENCE: 2
ctagtacgga ttagaagccg ccgagcgggt gacagccctc cgaaggaaga ctctcctccg     60
tgcgtcctcg tcttcaccgg tcgcgttcct gaaacgcaga tgtgcctcgc gccgcactgc   120
tccgaacaat aaagattcta caatactagc ttttatggtt atgaagagga aaaattggca   180
gtaacctggc cccacaaacc ttcaaatgaa cgaatcaaat taacaaccat aggatgataa   240
tgcgattagt tttttagcct tatttctggg gtaattaatc agcgaagcga tgattttga   300 tctattaaca gatatataaa tgcaaaaact gcataaccac tttaactaat actttcaaca   360
ttttcggttt gtattacttc ttattcaaat gtaataaaag tatcaacaaa aaattgttaa   420
tatacctcta tactttaacg tcaaggagaa aaaccccggg atcggactac tagcagctgt   480
aatacgactc actataggga atattaagct tatgagattt ccttcaattt ttactgctgt   540
tttattcgca gcatcctccg cattagctgc tccagtcaac actacaacag aagatgaaac   600
ggcacaaatt ccggctgaag ctgtcatcgg ttactcagat ttagaagggg atttcgatgt   660
tgctgttttg ccattttcca acagcacaaa taacgggtta ttgtttataa atactactat   720
tgccagcatt gctgctaaag aagaggggt atctctcgag aaaagagagg ctgaagctta   780
cccatacgac gttccagact acgctggtgg tggtggttct gctagcgcgg ccgcggcctc   840
aggggcctcc ggaattctag aacaacaggg taagcctatc cctaaccctc tcctcggtct   900
cgattctacg cgtaccggtc atcatcacca tcaccattga gtttaaaccc gctgatccta   960
gagggccgca tcatgtaatt agttatgtca gcttacatt cacgccctcc ccccacatcc  1020
gctctaaccg aaaaggaagg agttagacaa cctgaagtct aggtccctat ttatttttt   1080 atagttatgt tagtattaag aacgttattt atatttcaaa ttttttcttt ttttctgtac  1140
agacgcgtgt acgcatgtaa cattatactg aaaaccttgc ttgagaaggt tttgggacgc  1200
tcgaaggctt taatttgcaa gctgcggccc tgcattaatg aatcggccaa cgcgcgggga  1260
gaggcggttt gcgtattggg cgctcttccg cttcctcgct cactgactcg ctgcgctcgg  1320
tcgttcggct gcggcgagcg gtatcagctc actcaaaggc ggtaatacgg ttatccacag  1380
aatcagggga taacgcagga agaacatgt gagcaaaagg ccagcaaaag cccaggaacc  1440
gtaaaaaggc cgcgttgctg gcgttttttcc ataggctccg ccccctgac gagcatcaca  1500 aaaatcgacg ctcaagtcag aggtggcgaa acccgacagg actataaaga taccaggcgt  1560
ttccccctgg aagctccctc gtgcgctctc ctgttccgac cctgccgctt accggatacc  1620
tgtccgcctt tctcccttcg ggaagcgtgg cgctttctca tagctcacgc tgtaggtatc  1680
tcagttcggt gtaggtcgtt cgctccaagc tgggctgtgt gcacgaaccc cccgttcagc  1740
ccgaccgctg cgccttatcc ggtaactatc gtcttgagtc aacccggta agacacgact  1800 tatcgccact ggcagcagcc actggtaaca ggattagcag agcgaggtat gtaggcggtg  1860
ctacagagtt cttgaagtgg tggcctaact acgctacac tagaaggaca gtatttggta  1920
tctgcgctct gctgaagcca gttaccttcg gaaaaagagt tggtagctct tgatccggca  1980
```

```
aacaaaccac cgctggtagc ggtggttttt ttgtttgcaa gcagcagatt acgcgcagaa   2040
aaaaaggatc tcaagaagat cctttgatct tttctacggg gtctgacgct cagtggaacg   2100
aaaactcacg ttaagggatt ttggtcatga gattatcaaa aaggatcttc acctagatcc   2160
tttaaaatta aaaatgaagt tttaaatcaa tctaaagtat atatgagtaa acttggtctg   2220
acagttacca atgcttaatc agtgaggcac ctatctcagc gatctgtcta tttcgttcat   2280
ccatagttgc ctgactcccc gtcgtgtaga taactacgat acgggagcgc ttaccatctg   2340
gccccagtgc tgcaatgata ccgcgagacc cacgctcacc ggctccagat ttatcagcaa   2400
taaaccagcc agccggaagg gccgagcgca gaagtggtcc tgcaacttta tccgcctcca   2460
tccagtctat taattgttgc cgggaagcta gagtaagtag ttcgccagtt aatagtttgc   2520
gcaacgttgt tggcattgct acaggcatcg tggtgtcact ctcgtcgttt ggtatggctt   2580
cattcagctc cggttcccaa cgatcaaggc gagttacatg atccccatg ttgtgcaaaa   2640 aagcggttag ctccttcggt cctccgatcg ttgtcagaag taagttggcc gcagtgttat   2700
cactcatggt tatggcagca ctgcataatt ctcttactgt catgccatcc gtaagatgct   2760
tttctgtgac tggtgagtac tcaaccaagt cattctgaga atagtgtatg cggcgaccga   2820
gttgctcttg cccggcgtca atacgggata atagtgtatc acatagcaga actttaaaag   2880
tgctcatcat tggaaaacgt tcttcggggc gaaaactctc aaggatctta ccgctgttga   2940
gatccagttc gatgtaaccc actcgtgcac ccaactgatc ttcagcatct tttactttca   3000
ccagcgtttc tgggtgagca aaaacaggaa ggcaaaatgc cgcaaaaaag gaataagggg   3060
cgacacggaa atgttgaata ctcatactct tcctttttca atgggtaata actgatataa   3120
ttaaattgaa gctctaatttt gtgagtttag tatacatgca tttacttata atacagtttt   3180
ttagttttgc tggccgcatc ttctcaaata tgcttcccag cctgcttttc tgtaacgttc   3240
accctctacc ttagcatccc ttcccttttgc aaatagtcct cttccaacaa taataatgtc   3300
agatcctgta gagaccacat catccacggt tctatactgt tgacccaatg cgtctccctt   3360
gtcatctaaa cccacaccgg gtgtcataat caaccaatcg taaccttcat ctcttccacc   3420
catgtctctt tgagcaataa agccgataac aaaatctttg tcgctcttcg caatgtcaac   3480
agtaccctta gtatattctc cagtagatag ggagcccttg catgacaatt ctgctaacat   3540
caaaaggcct ctaggttcct tgttacttc ttctgccgcc tgcttcaaac cgctaacaat   3600
acctgggccc accacaccgt gtgcattcgt aatgtctgcc cattctgcta ttctgtatac   3660
acccgcagag tactgcaatt tgactgtatt accaatgtca gcaaattttc tgtcttcgaa   3720
gagtaaaaaa ttgtacttgg cggataatgc ctttagcggc ttaactgtgc cctccatgga   3780
aaaatcagtc aagatatcca catgtgtttt tagtaaacaa attttgggac ctaatgcttc   3840
aactaactcc agtaattcct tggtggtacg aacatccaat gaagcacaca agtttgtttg   3900
cttttcgtgc atgatattaa atagcttggc agcaacagga ctaggatgag tagcagcacg   3960
ttccttatat gtagctttcg acatgattta tcttcgtttc ctgcaggttt ttgttctgtg   4020
cagttgggtt aagaatactg ggcaatttca tgtttcttca acactacata tgcgtatata   4080
taccaatcta agtctgtgct ccttccttcg ttcttccttc tgttcggaga ttaccgaatc   4140
aaaaaaattt caaagaaacc gaaatcaaaa aaagaataaa aaaaaaatg atgaattgaa   4200 ttgaaaagct agcttatcga tgggtccttt tcatcacgtg ctataaaaat aattataatt   4260 taaattttt aatataaaata tataaattaa aaatagaaag taaaaaaaga aattaaagaa   4320
aaaatagttt ttgttttccg aagatgtaaa agactctagg gggatcgcca acaaatacta   4380
```

```
cctttatct tgctcttcct gctctcaggt attaatgccg aattgtttca tcttgtctgt    4440
gtagaagacc acacacgaaa atcctgtgat tttacatttt acttatcgtt aatcgaatgt    4500
atatctattt aatctgcttt tcttgtctaa taaatatata tgtaaagtac gcttttgtt     4560 gaaatttttt aaacctttgt ttatttttt ttcttcattc cgtaactctt ctaccttctt     4620
tatttacttt ctaaaatcca aatacaaaac ataaaaataa ataaacacag agtaaattcc    4680
caaattattc catcattaaa agatacgagg cgcgtgtaag ttacaggcaa gcgatccgtc    4740
cgccggcgaa cgtggcgaga aaggaaggga agaaagcgaa aggagcgggg gctagggcgg    4800
tgggaagtgt aggggtcacg ctgggcgtaa ccaccacacc cgccgcgctt aatgggggcgc   4860 tacagggcgc gtggggatga tcca                                          4884
```

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Asp Tyr Lys Asp Asp Asp Lys
1               5

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gattataaag atgacgataa a                                              21

<210> SEQ ID NO 5
<211> LENGTH: 18
<212> TYPE: PRT
<213> ORGANISM: Homo sapiens I

<400> SEQUENCE: 5

Pro Ser Thr Pro Pro Thr Pro Ser Pro Ser Thr Pro Pro Thr Pro Ser
1               5                   10                  15

Pro Ser

<210> SEQ ID NO 6
<211> LENGTH: 54
<212> TYPE: DNA
<213> ORGANISM: Homo sapiens

<400> SEQUENCE: 6
ccatcaacac caccaactcc aagtccttct actcctccta caccttcacc atca           54

<210> SEQ ID NO 7
<211> LENGTH: 14
<212> TYPE: PRT
<213> ORGANISM: E. Coli

<400> SEQUENCE: 7

Gly Leu Asn Asp Ile Phe Glu Ala Gln Lys Glu Trp His Glu
1               5                   10

```
<210> SEQ ID NO 8
<211> LENGTH: 48
<212> TYPE: DNA
<213> ORGANISM: E. Coli

<400> SEQUENCE: 8
ggtttgaatg atattttga agctcaaaaa attgaatggc atgaawas                48

<210> SEQ ID NO 9
<211> LENGTH: 7100
<212> TYPE: DNA
<213> ORGANISM: Artificial Sequence
<220> FEATURE:
<223> OTHER INFORMATION: Synthetic

<400> SEQUENCE: 9
gacggacgaa agggcctcgt gatacgccta tttttatagg ttaatgtcat gataataatg     60
gtttcttagg acgatcgct tgcctgtaac ttacacgcgc ctcgtatctt ttaatgatgg     120 ataatttgg gaatttactc tgtgtttatt tattttatg ttttgtattt ggattttaga     180
aagtaaataa agaaggtaga agagttacgg aatgaagaaa aaaaaataaa caaaggttta    240
aaaaatttca acaaaaagcg tactttacat atatatttat tagacaagaa aagcagatta    300
aatagatata cattcgatta acgataagta aaatgtaaaa tcacaggatt ttcgtgtgtg    360
gtcttctaca cagacaagat gaaacaattc ggcattaata cctgagagca ggaagagcaa    420 gataaaggt agtatttgtt ggcgatcccc ctagagtctt ttacatcttc ggaaaacaaa    480 aactatttt tctttaattt cttttttac tttctatttt taatttatat atttatatta     540 aaaatttaa attataatta tttttatagc acgtgatgaa aaggacccag gtggcactttt   600 tcggggaaat gtgcgcggaa cccctatttg tttattttttc taaatacatt caaatatgta    660
tccgctcatg agacaataac cctgataaat gcttcaataa tattgaaaaa ggaagagtat    720
gagtattcaa catttccgtg tcgcccttat tccctttttt gcggcatttt gccttcctgt    780
ttttgctcac ccagaaacgc tggtgaaagt aaaagatgct gaagatcagt tgggtgcacg    840
agtgggttac atcgaactgg atctcaacag cggtaagatc cttgagagtt ttcgccccga    900
agaacgtttt ccaatgatga gcacttttaa agttctgcta tgtggcgcgg tattatcccg    960
tattgacgcc gggcaagagc aactcggtcg ccgcatacac tattctcaga atgacttggt   1020
tgagtactca ccagtcacag aaaagcatct tacggatggc atgacagtaa gagaattatg   1080
cagtgctgcc ataaccatga gtgataacac tgcggccaac ttacttctga acgatcgg    1140 aggaccgaag gagctaaccg ctttttttgca caacatgggg gatcatgtaa ctcgccttga   1200
tcgttgggaa ccggagctga atgaagccat accaaacgac gagcgtgaca ccacgatgcc   1260
tgtagcaatg gcaacaacgt tgcgcaaact attaactggc gaactactta ctctagcttc   1320
ccggcaacaa ttaatagact ggatggaggc ggataaagtt gcaggaccac ttctgcgctc   1380
ggcccttccg gctggctggt ttattgctga taaatctgga gccggtgagc gtgggtctcg   1440
cggtatcatt gcagcactgg ggccagatgg taagccctcc cgtatcgtag ttatctacac   1500
gacggggagt caggcaacta tggatgaacg aaatagacag atcgctgaga taggtgcctc   1560
actgattaag cattggtaac tgtcagacca agtttactca tatatacttt agattgattt   1620
aaaacttcat ttttaattta aaaggatcta ggtgaagatc cttttttgata atctcatgac   1680 caaaatccct taacgtgagt tttcgttcca ctgagcgtca gaccccgtag aaaagatcaa   1740
aggatcttct tgagatcctt ttttttctgcg cgtaatctgc tgcttgcaaa caaaaaaacc   1800
```

```
accgctacca gcggtggttt gtttgccgga tcaagagcta ccaactcttt ttccgaaggt    1860
aactggcttc agcagagcgc agataccaaa tactgtcctt ctagtgtagc cgtagttagg    1920
ccaccacttc aagaactctg tagcaccgcc tacatacctc gctctgctaa tcctgttacc    1980
agtggctgct gccagtggcg ataagtcgtg tcttaccggg ttggactcaa gacgatagtt    2040
accggataag cgcagcggt cgggctgaac gggggttcg tgcacacagc ccagcttgga    2100
gcgaacgacc tacaccgaac tgagatacct acagcgtgag ctatgagaaa gcgccacgct    2160
tcccgaaggg agaaaggcgg acaggtatcc ggtaagcggc agggtcggaa caggagagcg    2220
cacgaggag cttccagggg gaaacgcctg gtatctttat agtcctgtcg ggtttcgcca    2280
cctctgactt gagcgtcgat ttttgtgatg ctcgtcaggg gggcggagcc tatggaaaaa    2340
cgccagcaac gcggccttt tacgttcct ggccttttgc tggccttttg ctcacatgtt    2400
ctttcctgcg ttatccctg attctgtgga taaccgtatt accgcctttg agtgagctga    2460
taccgctcgc cgcagccgaa cgaccgagcg cagcgagtca gtgagcgagg aagcggaaga    2520
gcgcccaata cgcaaaccgc ctctccccgc gcgttggccg attcattaat gcagctggca    2580
cgacaggttt cccgactgga aagcgggcag tgagcgcaac gcaattaatg tgagttacct    2640
cactcattag gcaccccagg ctttacactt tatgcttccg gctcctatgt tgtgtggaat    2700
tgtgagcgga taacaatttc acacaggaaa cagctatgac catgattacg ccaagcgcgc    2760
aattaacct cactaaaggg aacaaaagct ggagctctga agtacggatt agaagccgcc    2820
gagcgggtga cagccctccg aaggaagact ctcctccgtg cgtcctcgtc ttcaccggtc    2880
gcgttcctga acgcagatg tgcctcgcgc cgcactgctc cgaacaataa agattctaca    2940
atactagctt ttatggttat gaagaggaaa aattggcagt aacctggccc cacaaacctt    3000
caaatgaacg aatcaaatta caaccatag gatgataatg cgattagttt tttagcctta    3060
tttctgggt aattaatcag cgaagcgatg atttttgatc tattaacaga tatataaatg    3120
caaaaactgc ataaccactt taactaatac tttcaacatt ttcggtttgt attacttctt    3180
attcaaatgt aataaaagta tcaacaaaaa attgttaata tacctctata ctttaacgtc    3240
aaggagaaaa aactatatct agaactagta tgaaagtgag gaaatatatt actttatgct    3300
tttggtgggc ctttttcaaca tccgctcttg tatcatcaca acaaattcca ttgaaggacc    3360
atacgtcacg acagtatttt gctgtagaaa gcaatgaaac attatcccgc ttggaggaaa    3420
tgcatccaaa ttggaaatat gaacatgatg ttcgagggct accaaaccat tatgtttttt    3480
caaaagagtt gctaaaattg gcaaaagat catcattaga agagttacag ggggataaca    3540
acgaccacat attatctgtc catgatttat tcccgcgtaa cgacctattt aagagactac    3600
cggtgcctgc tccaccaatg gactcaagct tgttaccggt aaaagaagct gagggatcca    3660
tgaaggataa caccgtgcca ctgaaattga ttgccctgtt agcgaacggt gaatttcact    3720
ctggcgagca gttgggtgaa acgctgggaa tgagccgggc ggctattaat aaacacattc    3780
agacactgcg tgactggggc gttgatgtct ttaccgttcc gggtaaagga tacagcctgc    3840
ctgagcctat ccagttactt aatgctaaac agatattggg tcagtggat ggcggtagtg    3900
tagccgtgct gccagtgatt gactccacga atcagtacct tcttgatcgt atcggagagc    3960
ttaaatcggg cgatgcttgc attgcagaat accagcaggc tggccgtggt cgccggggtc    4020
ggaaatggtt ttcgcctttt ggcgcaaact tatatttgtc gatgttctgg cgtctggaac    4080
aaggcccggc ggcggcgatt ggtttaagtc tggttatcgg tatcgtgatg gcggaagtat    4140
tacgcaagct gggtgcagat aaagttcgtg ttaaatggcc taatgacctc tatctgcagg    4200
```

```
atcgcaagct ggcaggcatt ctggtggagc tgactggcaa aactggcgat gcggcgcaaa    4260
tagtcattgg agccgggatc aacatggcaa tgcgccgtgt tgaagagagt gtcgttaatc    4320
aggggtggat cacgctgcag gaagcgggga tcaatctcga tcgtaatacg ttggcggcca    4380
tgctaatacg tgaattacgt gctgcgttgg aactcttcga acaagaagga ttggcacctt    4440
atctgtcgcg ctgggaaaag ctggataatt ttattaatcg cccagtgaaa cttatcattg    4500
gtgataaaga aatatttggc atttcacgcg gaatagacaa cagggggct ttattacttg    4560 agcaggatgg aataataaaa ccctggatgg gcggtgaaat atccctgcgt agtgcagaaa    4620
aagaattcga acaaaaactc atctcagaag aggatctgtc tgagtacgat tctactttgg    4680
acaatggaac ttccggaatt actgagcccg aagaggttga ggacttcgat tttgatttgt    4740
ccgatgaaga ccatcttgca agtttgtctt catcagaaaa cggtgatgct gaacatacaa    4800
ttgatagtgt actaacaaac gaaaatccat ttagtgaccc tataaagcaa aagttcccaa    4860
atgacgccaa cgcagaatct gcttccaata aattacaaga attacagcct gatgttcctc    4920
catcttccgg acgatcgtga taactcgagt catgtaatta gttatgtcac gcttacattc    4980
acgccctccc cccacatccg ctctaaccga aaaggaagga gttagacaac ctgaagtcta    5040
ggtccctatt tattttttta tagttatgtt agtattaaga acgttattta tatttcaaat    5100
ttttcttttt tttctgtaca gacgcgtgta cgcatgtaac attatactga aaaccttgct    5160
tgagaaggtt ttgggacgct cgaaggcttt aatttgcggc cggtacccaa ttcgccctat    5220
agtgagtcgt attacgcgcg ctcactggcc gtcgttttac aacgtcgtga ctgggaaaac    5280
cctggcgtta cccaacttaa tcgccttgca gcacatcccc ctttcgccag ctggcgtaat    5340
agcgaagagg cccgcaccga tcgcccttcc caacagttgc gcagcctgaa tggcgaatgg    5400
cgcgacgcgc cctgtagcgg cgcattaagc gcggcgggtg tggtggttac gcgcagcgtg    5460
accgctacac ttgccagcgc cctagcgccc gctcctttcg ctttcttccc ttcctttctc    5520
gccacgttcg ccggctttcc ccgtcaagct ctaaatcggg ggctcccttt agggttccga    5580
tttagtgctt tacggcacct cgaccccaaa aaacttgatt agggtgatgg ttcacgtagt    5640
gggccatcgc cctgatagac ggttttttcgc cctttgacgt tggagtccac gttctttaat    5700
agtggactct tgttccaaac tggaacaaca ctcaaccta tctcggtcta ttcttttgat    5760
ttataaggga ttttgccgat ttcggcctat tggttaaaaa atgagctgat ttaacaaaaa    5820
tttaacgcga ttttaacaa atattaacg tttacaattt cctgatgcgg tattttctcc    5880
ttacgcatct gtgcggtatt tcacaccgca taggcaagtg cacaaacaat acttaaataa    5940
atactactca gtaataacct atttcttagc atttttgacg aaatttgcta ttttgttaga    6000
gtcttttaca ccatttgtct ccacacctcc gcttacatca acaccaataa cgccatttaa    6060
tctaagcgca tcaccaacat tttctggcgt cagtccacca gctaacataa aatgtaagct    6120
ttcggggctc tcttgccttc caacccagtc agaaatcgag ttccaatcca aagttcacc    6180 tgtcccacct gcttctgaat caaacaaggg aataaacgaa tgaggtttct gtgaagctgc    6240
actgagtagt atgttgcagt cttttggaaa tacgagtctt ttaataactg gcaaaccgag    6300
gaactcttgg tattcttgcc acgactcatc tccatgcagt tggacgatat caatgccgta    6360
atcattgacc agagccaaaa catcctcctt aggttgatta cgaaacacgc caaccaagta    6420
tttcggagtg cctgaactat tttatatgc ttttacaaga cttgaaattt tccttgcaat    6480
aaccgggtca attgttctct ttctattggg cacacatata atacccagca agtcagcatc    6540
```

```
ggaatctaga gcacattctg cggcctctgt gctctgcaag ccgcaaactt tcaccaatgg      6600
accagaacta cctgtgaaat taataacaga catactccaa gctgcctttg tgtgcttaat      6660
cacgtatact cacgtgctca atagtcacca atgccctccc tcttggccct ctccttttct      6720
tttttcgacc gaattaattc ttaatcggca aaaaagaaa agctccggat caagattgta       6780
cgtaaggtga caagctattt ttcaataaag aatatcttcc actactgcca tctggcgtca      6840
taactgcaaa gtacacatat attacgatgc tgtctattaa atgcttccta tattatatat     6900
atagtaatgt cgtttatggt gcactctcag tacaatctgc tctgatgccg catagttaag      6960
ccagccccga caccgccaa cacccgctga cgcgccctga cgggcttgtc tgctcccggc       7020
atccgcttac agacaagctg tgaccgtctc cgggagctgc atgtgtcaga ggttttcacc      7080
gtcatcaccg aaacgcgcga                                                  7100
```

<210> SEQ ID NO 10
<211> LENGTH: 963
<212> TYPE: DNA
<213> ORGANISM: E. Coli

<400> SEQUENCE: 10

```
atgaaggata acaccgtgcc actgaaattg attgccctgt agcgaacgg tgaatttcac       60 tctggcgagc agttgggtga aacgctggga atgagccggg cggctattaa taaacacatt     120
cagacactgc gtgactgggg cgttgatgtc tttaccgttc cgggtaaagg atacagcctg     180
cctgagccta tccagttact taatgctaaa cagatattgg gtcagctgga tggcggtagt     240
gtagccgtgc tgccagtgat tgactccacg aatcagtacc ttcttgatcg tatcggagag     300
cttaaatcgg gcgatgcttg cattgcagaa taccagcagg ctggccgtgg tcgccggggt    360
cggaaatggt tttcgccttt tggcgcaaac ttatatttgt cgatgttctg gcgtctggaa     420
caaggcccgg cggcggcgat tggtttaagt ctggttatcg gtatcgtgat ggcggaagta     480
ttacgcaagc tgggtgcaga taaagttcgt gttaaatggc ctaatgacct ctatctgcag     540
gatcgcaagc tggcaggcat tctggtggag ctgactggca aaactggcga tgcggcgcaa     600
atagtcattg gagccgggat caacatggca atgcgccgtg ttgaagagag tgtcgttaat     660 cagggtgga tcacgctgca ggaagcgggg atcaatctcg atcgtaatac gttggcggcc      720
atgctaatac gtgaattacg tgctgcgttg gaactcttcg aacaagaagg attggcacct     780
tatctgtcgc gctgggaaaa gctggataat tttattaatc gcccagtgaa acttatcatt     840
ggtgataaag aaatatttgg catttcacgc ggaatagaca aacagggggc tttattactt     900
gagcaggatg gaataataaa accctggatg ggcggtgaaa tatccctgcg tagtgcagaa     960
aaa                                                                    963
```

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11

```
ctagaagctt gccgccatga aggataacac cgtgcc                                36
```

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
gatgagtttt tgttcgaatt cttttctgc actacgcagg g        41

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
ctagggatcc atgaaggata acaccgtgcc        30

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
atatctcgag ttattacaga tcctcttctg atgagatg        38

<210> SEQ ID NO 15
<211> LENGTH: 396
<212> TYPE: DNA
<213> ORGANISM: Saccharomyces cerevisiae

<400> SEQUENCE: 15
actagtatga aagtgaggaa atatattact ttatgctttt ggtgggcctt ttcaacatcc        60
gctcttgtat catcacaaca aattccattg aaggaccata cgtcacgaca gtattttgct       120
gtagaaagca atgaaacatt atcccgcttg gaggaaatgc atccaaattg gaaatatgaa       180
catgatgttc gagggctacc aaaccattat gttttttcaa aagagttgct aaaattgggc       240
aaaagatcat cattagaaga gttacagggg gataacaacg accacatatt atctgtccat       300
gatttattcc cgcgtaacga cctatttaag agactaccgg tgcctgctcc accaatggac       360
tcaagcttgt taccggtaaa agaagctgag ggatcc                                 396

<210> SEQ ID NO 16
<211> LENGTH: 43
<212> TYPE: DNA
<213> ORGANISM: Artificial Sequence
<220> FEATURE:
<223> OTHER INFORMATION: Synthetic

<400> SEQUENCE: 16
catgactagt atgaaagtga ggaaatatat tactttatgc ttt        43

<210> SEQ ID NO 17
<211> LENGTH: 46
<212> TYPE: DNA
<213> ORGANISM: Artificial Sequence
<220> FEATURE:
<223> OTHER INFORMATION: Synthetic

<400> SEQUENCE: 17
attactcgag ttatcacgat cgtccggaag atggaggaac atcagg        46

<210> SEQ ID NO 18

<211> LENGTH: 327
<212> TYPE: DNA
<213> ORGANISM: Artificial Sequence
<220> FEATURE:
<223> OTHER INFORMATION: Synthetic

<400> SEQUENCE: 18

```
gaattcgaac aaaaactcat ctcagaagag gatctgtctg agtacgattc tactttggac    60
aatggaactt ccggaattac tgagcccgaa gaggttgagg acttcgattt tgatttgtcc   120
gatgaagacc atcttgcaag tttgtcttca tcagaaaacg gtgatgctga acatacaatt   180
gatagtgtac taacaaacga aaatccattt agtgaccctca taaagcaaaa gttcccaaat   240
gacgccaacg cagaatctgc ttccaataaa ttacaagaat tacagcctga tgttcctcca   300
tcttccggac gatcgtgata actcgag                                      327
```

<210> SEQ ID NO 19
<211> LENGTH: 68
<212> TYPE: DNA
<213> ORGANISM: Artificial Sequence
<220> FEATURE:
<223> OTHER INFORMATION: Synthetic

<400> SEQUENCE: 19

```
ctgagaattc gaacaaaaac tcatctcaga agaggatctg tctgagtacg attctacttt    60
ggacaatg                                                           68
```

<210> SEQ ID NO 20
<211> LENGTH: 46
<212> TYPE: DNA
<213> ORGANISM: Artificial Sequence
<220> FEATURE:
<223> OTHER INFORMATION: Synthetic

<400> SEQUENCE: 20

```
attactcgag ttatcacgat cgtccggaag atggaggaac atcagg                  46
```

<210> SEQ ID NO 21
<211> LENGTH: 31
<212> TYPE: DNA
<213> ORGANISM: Artificial Sequence
<220> FEATURE:
<223> OTHER INFORMATION: Synthetic

<400> SEQUENCE: 21

```
ctagagatct atggccttgc caacggctcg a                                  31
```

<210> SEQ ID NO 22
<211> LENGTH: 31
<212> TYPE: DNA
<213> ORGANISM: Artificial Sequence
<220> FEATURE:
<223> OTHER INFORMATION: Synthetic

<400> SEQUENCE: 22

```
catgccgccg gaggatggtc cgttcaggct g                                  31
```

<210> SEQ ID NO 23
<211> LENGTH: 40
<212> TYPE: DNA
<213> ORGANISM: Artificial Sequence
<220> FEATURE:
<223> OTHER INFORMATION: Synthetic

<400> SEQUENCE: 23
gattataaag atgacgataa aggtggtggt ggttctgcta                    40

<210> SEQ ID NO 24
<211> LENGTH: 39
<212> TYPE: DNA
<213> ORGANISM: Artificial Sequence
<220> FEATURE:
<223> OTHER INFORMATION: Synthetic

<400> SEQUENCE: 24
gggttaggga taggcttacc ctgttgttct agaattccg                     39

<210> SEQ ID NO 25
<211> LENGTH: 62
<212> TYPE: DNA
<213> ORGANISM: Artificial Sequence
<220> FEATURE:
<223> OTHER INFORMATION: Synthetic

<400> SEQUENCE: 25
gattataaag atgacgataa aggtggtggt ggttctgcta gcgaagtgga gaagacagcc    60
tg                                                             62

<210> SEQ ID NO 26
<211> LENGTH: 59
<212> TYPE: DNA
<213> ORGANISM: Artificial Sequence
<220> FEATURE:
<223> OTHER INFORMATION: Synthetic

<400> SEQUENCE: 26
gggttaggga taggcttacc ctgttgttct agaattccga gtgctaggac ggtgagaac     59

<210> SEQ ID NO 27
<211> LENGTH: 61
<212> TYPE: DNA
<213> ORGANISM: Artificial Sequence
<220> FEATURE:
<223> OTHER INFORMATION: Synthetic

<400> SEQUENCE: 27
gattataaag atgacgataa aggtggtggt ggttctgcta gcggtcacac agagcctggt    60
c                                                              61

<210> SEQ ID NO 28
<211> LENGTH: 58
<212> TYPE: DNA
<213> ORGANISM: Artificial Sequence
<220> FEATURE:
<223> OTHER INFORMATION: Synthetic

<400> SEQUENCE: 28
gggttaggga taggcttacc ctgttgttct agaattccag gcagggagga tggagtac      58

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
aatatacctc tatactttaa cgtc                                     24

```
<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
gcgtgaatgt aagcgtgac                                                      19

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
cgagaaaaga gaggctgaag                                                     20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ggtcatcatc accatcacca                                                     20

<210> SEQ ID NO 33
<211> LENGTH: 284
<212> TYPE: PRT
<213> ORGANISM: Artificial Sequence
<220> FEATURE:
<223> OTHER INFORMATION: Synthetic

<400> SEQUENCE: 33
```

Asp Tyr Lys Asp Asp Asp Lys Gly Gly Gly Gly Ser Ala Ser Gln Val
1               5                   10                  15

Gln Leu Val Gln Ser Gly Ala Glu Val Lys Lys Pro Gly Ala Ser Val
            20                  25                  30

Lys Val Ser Cys Gln Ala Ser Gly Tyr Thr Phe Thr Ser Asn Tyr Met
        35                  40                  45

His Trp Val Arg Gln Ala Pro Gly Gln Gly Leu Glu Trp Met Gly Ile
    50                  55                  60

Ile Asn Pro Ser Asp Gly Ser Thr Thr Tyr Ala Gln Arg Phe Gln Gly
65                  70                  75                  80

Arg Val Thr Met Thr Arg Asp Thr Ser Thr Ser Arg Val Tyr Met Glu
                85                  90                  95

Leu Ser Ser Leu Arg Ser Glu Asp Thr Ala Val Tyr Tyr Cys Ala Arg
            100                 105                 110

Glu Gly Ala Gly Phe Gly Pro Ala Ser Tyr Val Ser Pro Tyr Tyr Ala
        115                 120                 125

Met Asp Val Trp Gly Gln Gly Thr Thr Val Thr Val Ser Ser Gly Ile
    130                 135                 140

Leu Gly Ser Gly Gly Gly Gly Ser Gly Gly Gly Gly Ser Gly Gly Gly
145                 150                 155                 160

Gly Ser Glu Thr Thr Leu Thr Gln Ser Pro Gly Thr Leu Ser Leu Ser
                165                 170                 175

```
Pro Gly Glu Arg Ala Thr Leu Ser Cys Arg Ala Ser Gln Ser Val Ser
            180                 185                 190

Ser Tyr Phe Leu Ala Trp Tyr Gln Gln Lys Pro Gly Gln Ala Pro Arg
        195                 200                 205

Leu Leu Ile Tyr Gly Ala Ser Ser Arg Ala Ser Gly Ile Pro Asp Arg
    210                 215                 220

Phe Ser Gly Ser Gly Ser Gly Thr Asp Phe Thr Leu Thr Ile Ser Arg
225                 230                 235                 240

Leu Glu Pro Glu Asp Phe Ala Val Tyr Tyr Cys Gln Glu Tyr Gly Gly
                245                 250                 255

Ser Thr Leu Ala Thr Phe Gly Pro Gly Thr Lys Val Asp Ile Lys Ser
            260                 265                 270

Gly Ile Leu Glu Gln Gln Gly Lys Pro Ile Pro Asn
        275                 280

<210> SEQ ID NO 34
<211> LENGTH: 132
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Ser Asn
            20                  25                  30

Tyr Met His Trp Val Arg Gln Ala Pro Gly Gln Gly Leu Glu Trp Met
        35                  40                  45

Gly Ile Ile Asn Pro Ser Asp Gly Ser Thr Thr Tyr Ala Gln Arg Phe
    50                  55                  60

Gln Gly Arg Val Thr Met Thr Arg Asp Thr Ser Thr Ser Arg Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Gly Pro Ala Ser Tyr Val Ser Pro Tyr
            100                 105                 110

Tyr Ala Met Asp Val Trp Gly Gln Gly Thr Thr Val Thr Val Ser Ser
        115                 120                 125

Gly Ile Leu Gly
    130

<210> SEQ ID NO 35
<211> LENGTH: 109
<212> TYPE: PRT
<213> ORGANISM: Artificial Sequence
<220> FEATURE:
<223> OTHER INFORMATION: Synthetic

<400> SEQUENCE: 35

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Glu Tyr Gly Ser Thr
                 85                  90                  95

Leu Ala Thr Phe Gly Pro Gly Thr Lys Val Asp Ile Lys
            100                 105

<210> SEQ ID NO 36
<211> LENGTH: 284
<212> TYPE: PRT
<213> ORGANISM: Artificial Sequence
<220> FEATURE:
<223> OTHER INFORMATION: Synthetic

<400> SEQUENCE: 36

Asp Tyr Lys Asp Asp Asp Lys Gly Gly Gly Ser Ala Ser Gln Val
 1               5                  10                  15

Gln Leu Gln Gln Ser Gly Pro Gly Leu Val Thr Pro Ser Gln Thr Leu
                 20                  25                  30

Ser Leu Thr Cys Ala Ile Ser Gly Asp Ser Val Ser Ser Asn Ser Ala
             35                  40                  45

Thr Trp Asn Trp Ile Arg Gln Ser Pro Ser Arg Gly Leu Glu Trp Leu
 50                  55                  60

Gly Arg Thr Tyr Tyr Arg Ser Lys Trp Tyr Asn Asp Tyr Ala Val Ser
 65                  70                  75                  80

Val Lys Ser Arg Met Ser Ile Asn Pro Asp Thr Ser Lys Asn Gln Phe
                 85                  90                  95

Ser Leu Gln Leu Asn Ser Val Thr Pro Glu Asp Thr Ala Val Tyr Tyr
            100                 105                 110

Cys Ala Arg Gly Met Met Thr Tyr Tyr Tyr Gly Met Asp Val Trp Gly
            115                 120                 125

Gln Gly Thr Thr Val Thr Val Ser Ser Gly Ile Leu Ser Gly Gly
            130                 135                 140

Gly Gly Ser Gly Gly Gly Ser Gly Gly Gly Ser Gln Pro Val
145                 150                 155                 160

Leu Thr Gln Ser Ser Leu Ser Ala Ser Pro Gly Ala Ser Ala Ser
                165                 170                 175

Leu Thr Cys Thr Leu Arg Ser Gly Ile Asn Val Gly Pro Arg Ile Tyr
            180                 185                 190

Trp Tyr Gln Gln Lys Pro Gly Ser Pro Pro Gln Tyr Leu Leu Asn Tyr
            195                 200                 205

Lys Ser Asp Ser Asp Lys Gln Gln Gly Ser Val Pro Ser Arg Phe
210                 215                 220

Ser Gly Ser Lys Asp Ala Ser Ala Asn Ala Gly Val Leu Leu Ile Ser
225                 230                 235                 240

Gly Leu Arg Ser Glu Asp Glu Ala Asp Tyr Tyr Cys Met Ile Trp His
                245                 250                 255

Ser Ser Ala Ala Val Phe Gly Gly Gly Thr Gln Leu Thr Val Leu Ser
                260                 265                 270

Gly Ile Leu Glu Gln Gln Gly Lys Pro Ile Pro Asn
            275                 280

<210> SEQ ID NO 37
<211> LENGTH: 127
<212> TYPE: PRT
<213> ORGANISM: Artificial Sequence
```

-continued

```
<220> FEATURE:
<223> OTHER INFORMATION: Synthetic

<400> SEQUENCE: 37

Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Gly Met Asp Val
            100                 105                 110

Trp Gly Gln Gly Thr Thr Val Thr Val Ser Ser Gly Ile Leu Leu
        115                 120                 125

<210> SEQ ID NO 38
<211> LENGTH: 114
<212> TYPE: PRT
<213> ORGANISM: Artificial Sequence
<220> FEATURE:
<223> OTHER INFORMATION: Synthetic

<400> SEQUENCE: 38

Gln Pro Val Leu Thr Gln Ser Ser Ser Leu Ser Ala Ser Pro Gly Ala
1               5                   10                  15

Ser Ala Ser Leu Thr Cys Thr Leu Arg Ser Gly Ile Asn Val Gly Pro
            20                  25                  30

Arg Ile Tyr Trp Tyr Gln Gln Lys Pro Gly Ser Pro Pro Gln Tyr Leu
        35                  40                  45

Leu Asn Tyr Lys Ser Asp Ser Asp Lys Gln Gln Gly Ser Gly Val Pro
    50                  55                  60

Ser Arg Phe Ser Gly Ser Lys Asp Ala Ser Ala Asn Ala Gly Val Leu
65                  70                  75                  80

Leu Ile Ser Gly Leu Arg Ser Glu Asp Glu Ala Asp Tyr Tyr Cys Met
                85                  90                  95

Ile Trp His Ser Ser Ala Ala Val Phe Gly Gly Gly Thr Gln Leu Thr
            100                 105                 110

Val Leu
```